(12) United States Patent
Sung

(10) Patent No.: US 7,695,947 B2
(45) Date of Patent: Apr. 13, 2010

(54) MODIFIED XYLANASES EXHIBITING INCREASED THERMOPHILICITY AND ALKALOPHILICITY

(75) Inventor: Wing L. Sung, Ontario (CA)

(73) Assignee: National Research Council of Canada, Ottawa, Ontario (CA)

( * ) Notice: Subject to any disclaimer, the term of this patent is extended or adjusted under 35 U.S.C. 154(b) by 1062 days.

(21) Appl. No.: 11/377,644

(22) Filed: Mar. 17, 2006

(65) Prior Publication Data

US 2009/0325267 A1    Dec. 31, 2009

Related U.S. Application Data

(62) Division of application No. 10/307,441, filed as application No. PCT/CA01/00769 on May 31, 2001, now abandoned.

(60) Provisional application No. 60/213,803, filed on May 31, 2000.

(51) Int. Cl.
    *C12N 9/26* (2006.01)
(52) U.S. Cl. ........................ 435/201; 435/278; 536/23.2
(58) Field of Classification Search .................. 435/201, 435/278; 536/23.2
    See application file for complete search history.

(56) References Cited

U.S. PATENT DOCUMENTS

| | | | |
|---|---|---|---|
| 5,078,802 A | 1/1992 | Imanaka et al. | 134/42 |
| 5,405,769 A | 4/1995 | Campbell et al. | 435/200 |
| 5,759,840 A | 6/1998 | Sung et al. | 435/200 |
| 5,866,408 A | 2/1999 | Sung et al. | 43/278 |
| 5,916,795 A | 6/1999 | Fukunaga et al. | |
| 6,682,923 B1 | 1/2004 | Bentzien et al. | 435/209 |
| 7,510,860 B1 | 3/2009 | Sung | |

FOREIGN PATENT DOCUMENTS

| | | |
|---|---|---|
| EP | 0 473 545 A2 | 3/1992 |
| EP | 0 828 002 A2 | 3/1998 |
| WO | 94/24270 | 10/1994 |
| WO | 95/12668 | 5/1995 |
| WO | WO 00/29587 A1 | 5/2000 |

OTHER PUBLICATIONS

Perez-Gonzalez et al., "Molecular Cloning and Expression in *Saccharomyces cerevisiae* of Two *Aspergillus nidulans* Xylanase Genes," Appl. Environ. Microbiol. 62(6):2179-2182 (1996).
Foreign Examination Report of Canadian Patent Application No. 2,410,917 mailed on Jul. 7, 2009.
Foreign Examination Report of Canadian Patent Application No. 2,410,917 mailed on Jul. 31, 2009.
Torronen et al., "Structural Comparison of Two Major *endo*-1,4-Xylanases from *Trichoderma reesei*", Biochemistry, 1995, pp. 847-856, vol. 34, No. 3.

Muilu et al., "Functional Conformational Changes of Endo-1,4-xylanase II From *Trichoderma reesei*: A Molecular Dynamics Study", Proteins: Structure, Function, and Genetics, Jun. 1, 1998, pp. 434-444, vol. 31, No. 4.
Georis et al., "An additional aromatic interaction improves the thermostability and thermophilicity of a mesophilic family 11 xylanase: Structural basis and molecular study", Protein Science, Mar. 2000, pp. 466-475, vol. 9, No. 3.
Torronen et al., "Three-dimensional structure of endo-1,4-β-xylanase II from *Trichoderma reesei*: two conformational states in the active site", The EMBO Journal, 1994, pp. 2493-2501, vol. 13, No. 11.
Moore, Jeffrey C. et al., "Strategies for the in vitro Evolution of Protein Function: Enzyme Evolution by Random Recombination of Improved Sequences", 272, p. 336-337, 1997.
Winterhalter, Christoph, et al, "Two Extremely Thermostable Xylanases of the Hyperthermophilic Bacterium *Thermotoga maritima* MSB8", Applied and Environmental Microbiology, May 1995, p. 1810-1815.
Wakarchuk, Warren, et al, "Thermostabilization of the *Bacillus circulans* xylanase by the introduction of disulfide bonds", Protein Engineering, vol. 7, No. 11, pp. 1379-1386, 1994.
Sung, Wing L., et al, "Expression of *Trichoderma reesei* and *Trichoderma viride* xylanases in *Escherichia coli*", Biochem. Cell Biol. 73: 253-259, 1995.
Sung, Wing L., et al, "Overexpression of the *Bacillus subtilis* and *circulans* Xylanases in *Escherichia coli*", Protein Expression and Purification 4, 200-206, 1993.
Sung, Wing L. et al, "Short synthetic oligodeoxyribonucleotide leader sequences enhance accumulation of human proinsulin synthesized in *Escherichia coli*", Proc. Natl. Acad. Sci. USA, vol. 83, pp. 561-565, Feb. 1986, Biochemistry.
Simpson, Helen D., et al, "An extremely thermostable xylanase from the thermophilic eubacterium Thermotoga", Biochem. J., vol. 277, 413-417, 1991.
Sakka, Kazuo, et al., "Nucleotide Sequence of the Clostridium stercorarium xynA Gene Encoding Xylanase A: Identification of Catalytic and Cellulose Binding Domains", Department of Bioscience, Faculty of Bioresources and Center for Molecular Biology and Genetics, Mic University, Tsu 514, Japan, Biosci. Biotech. Biochem. vol. 57, (2), 273-277, 1993.

(Continued)

*Primary Examiner*—Tekchand Saidha
(74) *Attorney, Agent, or Firm*—Cooley Godward Kronish LLP

(57) ABSTRACT

The present invention pertains to modified xylanase enzymes that exhibit increased thermostability and alkalophilicity, when compared with their native counterparts. Several modified xylanases exhibiting these properties are disclosed including xylanases with at least one modification at amino acid position 10, 27, 29, 75, 104, 105, 125, 129, 132, 135, 144, 157, 161, 162 or 165, or a combination thereof. Also included within the present invention is a modified xylanase that comprises at least one substituted amino acid residue and that may be characterized as having a maximum effective temperature (MET) between about 69° C. and about 78° C., wherein the modified xylanase is a Family 11 xylanase obtained from a Trichoderma sp. The present invention also includes a modified Family 11 xylanase obtained from a Trichoderma sp. characterized as having a maximum effective pH (MEP) between 5.8 and about 7.6. Modified xylanases characterized as having a MET between about 69° C. and about 78° C. and a MET between about 5.8 and 7.6 are also disclosed.

25 Claims, 23 Drawing Sheets

OTHER PUBLICATIONS

Nissen, Anne Mette, et al., "Xylanases for the Pulp and Paper Industry", Xylans and Xylanases, 1992 Elsevier Science Publishers B.V. pp. 325-337.

Van den Tweel, W.J.J., editor et al., "Stability and Stabilization of Enzymes", Proceedings of an International Symposium held in Maastricht, The Netherlands. 22-25, Nov. 1992; pp. 111-131.

Mathrani, Indra Madan, et al., "Thermophilic and alkalophilic xylanases from several Dictyoglomus isolates", Appl Microbiol Biotechnol, 1992, vol. 38, pp. 23-27.

Luthi, Ernst, "Xylanase from the Extremely Thermophilic Bacterium "*Caldocellum saccharolyticum*": Overexpression of the Gene in *Escherichia coli* and Characterization of the Gene Product", Applied and Environmental Microbiology, Sep. 1990. pp. 2677-2683.

Irwin, Diana, et al, "Characterization and Sequence of a *Thermomonospora fusca* Xylanase", Applied and Environmental Microbiology, Mar. 1994, p. 763-770.

Gruber, Karl, et al., "Thermophilic Xylanase from Thermomyces lanuginosus: High-Resolution X-ray Structure and Modeling Studies", Biochemistry 1998, vol. 37, pp. 13475-13485.

Fisk, Spencer R. et al., "Development of A Method for the Stabilization and Formulation of Xylanase from Trichoderma Using Experimental Design", Van den Tweel, W.J.J., editor et al., "Stability and Stabilization of Enzymes", Proceedings of an International Symposium held in Maastricht, The Netherlands., Nov. 22-25, 1992, pp. 323-328.

Arase, Akemi, et al., "Stabilization of xylanase by random mutagenesis", Federation of European Biochemical Societies, vol. 316, No. 2, pp. 123-127, Jan. 1993.

Tolan, J.S. et al., "The use of Enzymes to decrease the $Cl_2$ requirements in pulp bleaching", Pulp & Paper Canada 93:5, 1992, pp. 39-42.

Lee, Song F. et al., "Purification and Characterization of Two Endoxylanases from *Clostridium acetobutylicum* ATCC 824", Applied and Environmental Microbiology, Apr. 1987, p. 644-650.

Zappe, Harold et al., "Nucleotide sequence of a *Clostridium acetobutylicum* P262 xylanase gene (xynB)", Nucleic Acids Research, vol. 18, No. 8, pp. 2179, Mar. 13, 1990.

Zappe, Harold, et al., "Cloning and expression of a xylanase gene from *Clostridium acetobutylicum* P262 in *Escherichia coli*", Appl Microbiol Biotechnol, 1987, vol. 27, p. 57-63.

```
Ca    23                                                                S AFNTQAAP  31
Cs     1                                                                G           1

Tr2#                    10          20           30          40
                         |           |            |           |
Bp     1   RTITNNEMGN HSGYDYELWK DYGNT-SMTL NNGGAFSAGW N--NIGNA   45
Ca    32   KTITSNEIGV NGGYDYELWK DYGNT-SMTL KNGGAFSCQW S--NIGNA   76
Fs     1   NSSVTGNVG  SSPYHYEIWY QGG-NNSMTF YDNGTYKASW N--GTNDF   44
Cs     2   RIIYDNETGT HGGYDYELWK DYGNT-IMEL NDGGTFSCQW S--NIGNA   46
Rf     1   SAADQQTRGN VGGYDYEMWN QNGQGQASMN PGAGSFTCSW S--NIENF   46
Tr2    1   QTIQPGTGY  NNGYFYSYWN DGHGGVTYTN GPGGQFSVNW S--NSGNF   45
Tv     1   QTIQPGTGF  NNGYFYSYWN DGHGGVTYTN GPGGQFSVNW S--NSGNF   45
Th     1   QTIGPGTGY  SNGYYYSYWN DGHAGVTYTN GGGGSFTVNW S--NSGNF   45
Sc     1   SGTPSSTGT  DGGYYYSWWT DGAGDATYQN NGGGSYTLTW SG-NNGNL   46
An     1            S AGINYVQNYN GNLGDFTY-D ESAGTFSMYW EDGVSSDF   38
AT     1            S AGINYVQNYN QNLGDFTY-D ESAGTFSMYW EDGVSSDF   38
Tr1    1              ASINYDQNYQ TGG-QVSYS- PSNTGFSVNW N--TQDDF   34
Aa     1   RSTPSSTGE  NNGYYYSFWT DGGGDVTYTN GNAGSYSVEW S--NVGNF   45
Ss     1   ATTIT-NETGY D-GMYYSFWT DGGGSVSMTL NGGGSYSTRW T--NCGNF   45
S1B    1   DTVVTTNQEGT NNGYYYSFWT DSQGTVSMNM GSGGQYSTSW R--NTGNF   47
S1C    1   ATTITTNQTGT D-GMYYSFWT DGGGSVSMTL NGGGSYSTQW T--NCGNF   46
T1     1   QTTPNSEGW  HDGYYYSWWS DGGAQATYTN LEGGTYEISW G--DGGNL   45
Tf     1   AVTSNETGY  HDGYFYSFWT DAPGTVSMEL GPGGNYSTSW R--NTGNF   45
Bc     1              ASTDYWQNWT DGGGIVNAVN GSGGNYSVNW S--NTGNF   36
Bs     1              ASTDYWQNWT DGGGIVNAVN GSGGNYSVNW S--NTGNF   36

Tr2#                    50          60           70          80
                         |           |            | *         |
Bp    46   LFRK-GKKFD ST-RTHHQLG NISINYNASF N-PSGNSYLC VYGWTQSP   90
Ca    77   LFRK-GKKFN DT-QTYKQLG NISVNYNCNY Q-PYGNSYLC VYGWTSSP  121
FS    45   LARV-GFKYD EK-HTYEELGPIDAYYKWSKQ GSAGGYNYIG IYGWTVDP   91
Cs    47   LFRK-GRKFN SD-KTYQELG DIVVEYGCDY N-PNGNSYLC VYGWTRNF   91
Rf    47   LARM-GKNYD SQKKNYKAFG NIVLTYDVEY T-PRGNSYMC VYGWTRNP   92
Tr2   46   VGGK-GWQPG TKNKV----- ---INFS-GS YNPNGNSYLS VYGWSRNP   83
Tv    46   VGGK-GWQPG TKNKV----- ---INFS-GS YNPNGNSYLS VYGWSRNP   83
Th    46   VGGK-GWQPG TKNKV----- ---INFS-GS YNPNGNSYLS IYGWSRNP   83
Sc    47   VGGK-GWNPG AASRS----- ---ISYS-GT YQPNGNSYLS VYGWTRSS   84
An    39   VVGL-GWTTG SSNA------ ---ITYSAEY SASGSSSYLA VYGWVNYP   76
At    39   VVGLGGWTTG SSNA------ ---ITYSAEY SASGSASYLA VYGWVNYP   77
Tr1   35   VVGV-GWTTG SSAP------ ---INFGGSF SVNSGTGLLS VYGWSTNP   72
Aa    46   VGGK-GWNPG SAKD------ ---ITYSGNF T-PSGNGYLS VYGWTTDP   82
Ss    46   VAGK-GWANG GR-RT----- ---VRYT-GW FNPSGNGYGC LYGWTSNP   82
S1B   48   VAGK-GWANG GR-RT----- ---VQYS-GS FNPSGNAYLA LYGWTSNP   84
S1C   47   VAGK-GWSTG DGN------- ---VRYN-GY FNPVGNGYGC LYGWTSNP   82
T1    46   VGGK-GWNPG LNARA----- ---IHFE-GV YQPNGNSYLA VYGWTRNP   83
Tf    46   VAGK-GWATG GR-RT----- ---VTYS-AS FNPSGNAYLT LYGWTRNP   82
Bc    37   VVGK-GWTTG SPFRT----- ---INYNAGV WAPNGNGYLT LYGWTRSP   75
Bs    37   VVGK-GWTTG SPFRT----- ---INYNAGV WAPNGNGYLT LYGWTRSP   75
```

FIGURE 1

```
Tr2#              90         100          110         120         130
                   |           |       *    |           |           |
Bp    91  LAEYYIVDSW GTYR-PT--G AYKGSFYADG GTYDIYETTR VNQPSIIG 135
Ca   122  LVEYYIVDSW GSWRPP--GG TSKGTITVDG GIYDIYETTR INQPSIQG 167
Fs    92  LVEYYIVDDW FNKPGANLLG QRKGEFTVDG DTYEIWQNTR VQQPSIKG 139
Cs    92  LVEYYIVESW GSWRPP--GA TPKGTITQWMAGTYEIYETTR VNQPSIDG 138
Rf    93  LMEYYIVEGW GDWRPPGNDG EVKGTVSANG NTYDIRKTMR YNQPSLDG 140
Tr2   84  LIEYYIVENF GTYN-PSTGA TKLGEVTSDG SVYDIYRTQR VNQPSIIG 130
Tv    84  LIEYYIVENF GTYN-PSTGA TKLGEVTSDG SVYDIYRTQR VNQPSIIG 130
Th    84  LIEYYIVENF GTYN-PSTGA TKLGEVTSDG SVYDIYRTQR VNQPSIIG 130
Sc    85  LIEYYIVESY GSYD-PSSAA SHKGSVTCNG ATYDILSTWR YNAPSIDG 131
An    77  GAEYYIVEDY GDYN-PCSSA TSLGTVYSDG STYQVCTDTR INEPSITG 123
At    78  QAEYYIVEDY GDYN-PCSSA TSLGTVYSDG STYQVCTDTR INEPSITG 124
Tr1   73  LVEYYIMEDN HNY--PAQ-G TVKGTVTSDG ATYTIWENTR VNEPSIQG 117
Aa    83  LIEYYIVESY GDYN-PGSGG TTRGNVSSDG SVYDIYTATR TNAPSIDG 129
Ss    83  LVEYYIVDNW GSYR-PT--G ETRGTVHSDG GTYDIYKTTR YNAPSVEA 127
S1B   85  LVEYYIVDNW GTYR-PT--G EYKGTVTSDG GTYDIYKTTR VNKPSVEG 129
S1C   83  LVEYYIVDNW GSYR-PT--G TYKGTVSSDG GTYDIYQTTR YNAPSVEG 127
Tl    84  LVEYYIVENF GTYD-PSSGA TDLGTVECDG SIYRLGKTTR VNAPSIDG 130
Tf    83  LVEYYIVESW GTYR-PT--G TYMGTVTTDG GTYDIYKTTR YNAPSIEG 127
Bc    76  LIEYYVVDSW GTYR-PT--G TYKGTVKSDG GTYDIYTTTR YNAPSIDG 120
Bs    76  LIEYYVVDSW GTYR-PT--G TYKGTVKSDG GTYDIYTTTR YNAPSIDG 120

Tr2#             140         150         160
                   |           |           |
Bp   136  -IATFKQYWS VRQTKRTS-- ------GTVS VSAHFRKWES LGMPM-GK 174
Ca   168  -NTTFKQYWS VRRTKRTS-- ------GTIS VSKHFAAWES KGMPL-GK 206
Fs   140  -TQTFPQYFS VRKSARSC-- ------GHID ITAHMKKWEE LGMKM-GK 177
Cs   139  -TATFQQYWS VRTSKRTS-- ------GTIS VTEHFKQWER MGMRM-GK 177
Rf   141  -TATFPQYWS VRQTSGSANN QTNYMKGTID VSKHFDAWSA AGLDMSGT 187
Tr2  131  -TATFYQYWS VRRNHR-S-S ------GSVN TANHFNAWAQ QGLTL-GT 168
Tv   131  -TATFYQYWS VRRTHR-S-S ------GSVN TANHFNAWAQ QGLTL-GT 168
Th   131  -TATFYQYWS VRRNHR-S-S ------GSVN TANHFNAWAS HGLTL-GT 168
Sc   132  -TQTFEQFWS VRNPKKAPGG SIS---GTVD VQCHFDAWKG LGMNLGSE 175
An   124  -TSTFTQYFS VRESTRTS-- ------GTVT VANHFNFWAQ HGFGN-SD 162
At   125  -TSTFTQYFS VRESTRTS-- ------GTVT VANHFNFWAH HGFHN-SD 163
Tr1  118  -TATFNQYIS VRNSPR-T-S ------GTVT VQNHFN-WAS LGLHLGQM 155
Aa   130  -TQTFSQYWS VRQNKR-VG- ------GTVT TSNHFNAWAK LGMNL-GT 167
Ss   128  -PAAFDQYWS VRQSKVT--S ------GTIT TGNHFDAWAR AGMNMGNF 168
S1B  130  TR-TFDQYWS VRQSKR-TG- ------GTIT TGNHFDAWAR AGMPLGNF 168
S1C  128  TK-TFQQYWS VRQSKVTSGS ------GTIT TGNHFDAWAR AGMNMGQF 168
Tl   131  TQ-TFDQYWS VRQDKR-T-S ------GTVQ TGCHFDAWAR AGLNVNGD 169
Tf   128  TR-TFDQYWS VRQSKRTS-- ------GTIT AGNHFDAWAR HGMHLGTH 166
Bc   121  DRTTFTQYWS VRQSKRPTGS N-----ATIT FTNHVNAWKS HGMNLGSN 163
Bs   121  DRTTFTQYWS VRQSKRPTGS N-----ATIT FSNHVNAWKS HGMNLGSN 163
```

FIGURE 1 CONT'D

```
Tr2#          170         180         190
               |           |           |
Bp    175   MYETAFTVEG  YQSSGSANVM  TNQLFIGN           201
Ca    207   MHETAFNIEG  YQSSGKADVN  SMSINIGK           233
Fs    178   MYEAKVLVEA  GGGSGSFDV-  TYFKMT             202
Cs    178   MYEVALTVEG  YQSSGYANVY  KNEIRIGANP....
Rf    188   LYEVSLNIEG  YRSNGSANVK  SVSV               211
Tr2   169   MDYQIVAVEG  YFSSGSASI-  TVS                190
Tv    169   MDYQIVAVEG  YFSSGSASI-  TVS                190
Th    169   MDYQIVAVEG  YFSSGSASI-  TVS                190
Sc    176   HNYQIVATEG  YQSSGTATI-  TVT                197
An    163   FNYQVMAVEA  WSGAGSASV-  TISS               184
At    164   FNYQVVAVEA  WSGAGSAAV-  TISS               185
Tr1   157   MNYQVVAVEG  WGGSGSASQ-  SVSN               178
Aa    168   HNYQILATEG  YQSSGSSSI-  TIQ                189
Ss    167   RYYMINATEG  YQSSGSSTI-  TVSG               189
S1B   169   SYYMINATEG  YQSSGTSSI-  NVGG..........
S1C   169   RYYMINATEG  YQSSGSSNI-  TVSG               191
Tl    170   HYYQIVATEG  YFSSGYARI-  TVADVG             194
Tf    167   D-YMIMATEG  YQSSGSSNVT  LGTS..........
Bc    164   WAYQVMATEG  YQSSGSSNV-  TVW                185
Bs    164   WAYQVMATEG  YQSSGSSNV-  TVW                185
```

Bp   *Bacillus pumilus* (SEQ ID NO:4)
Ca   *Clostridium acetobutylicum* P262 XynB (SEQ ID NO:6)
Cs   *Clostridium stercorarium* xynA (SEQ ID NO:7)
Rf   *Ruminococcus flavefaciens* (SEQ ID NO:8)
Tr2  *Trichoderma reesei* XYN II (SEQ ID NO:16)
Tv   *Trichoderma viride* (SEQ ID NO:17)
Th   *Trichoderma harzianum* (SEQ ID NO:14)
Sc   *Schizophyllum commune* Xylanase A (SEQ ID NO:9)
An   *Aspergillus niger*, var. *awamori* (SEQ ID NO:1)
At   *Aspergillus tubigensis* (SEQ ID NO:2)
Tr1  *Trichoderma reesei* XYN I (SEQ ID NO:15)
Aa   *Aspargillus awamori* var. *kawachi* Xyn B (SEQ ID NO:19)
Fs   *Fibrobacter succinogenes* XYN II (SEQ ID NO:18)
Ss   *Streptomyces* sp. 36a (SEQ ID NO:12)
S1B  *Streptomyces lividans* Xln B (SEQ ID NO:10)
S1C  *Streptomyces lividans* Xln C (SEQ ID NO:11)
Tl   *Thermomyces lanuginosus* Xyn (SEQ ID NO:20)
Tf   *Thermomonospora fusca* TfxA (SEQ ID NO:13)
Bc   *Bacillus circulans* (SEQ ID NO:3)
Bs   *Bacillus subtilis* (SEQ ID NO:5)

FIGURE 1 CONT'D

```
                                                                    st
                        (SEQ ID NO:54) 5'-CT AGC TAA GGA GG CTG CAG ATG
                        (SEQ ID NO:55)      G ATT CCT CC GAC GTC TAC
                                              NheI  |         PstI
```

```
                                              TrX-1
        1    2    3    4    5    6    7    8    9   10   11   12   13   14   15   16
        Q    T    I    Q    P    G    T    G    Y    N    N    G    Y    F    Y    S
       CAA  ACA  ATA  CAA  CCA  GGA  ACC  GGT  TAC  AAC  AAC  GGT  TAC  TTT  TAC  AGC
       GTT  TGT  TAT  GTT  GGT  CCT  TGG  CCA  ATG  TTG  TTG  CCA  ATG  AAA  ATG  TCG
              TrX-8                AgeI                            |

|               XyTv-2
       17   18   19   20   21   22   23   24   25   26   27   28   29   30   31   32
        Y    W    N    D    G    H    G    G    V    T    Y    T    N    G    P    G
       TAT  TGG  AAC  GAT  GGC  CAT  GGT  GGT  GTT  ACC  TAT  ACA  AAC  GGG  CCC  GGA
       ATA  ACC  TTG  CTA  CCG  GTA  CCA  CCA  CAA  TGG  ATA  TGT  TTG  CCC  GGG  CCT
                                 NcoI                          XyTv-7     ApaI

|
       33   34   35   36   37   38   39   40   41   42   43   44   45   46   47   48
        G    Q    F    S    V    N    W    S    N    S    G    N    F    V    G    G
       GGC  CAA  TTT  AGC  GTC  AAT  TGG  TCT  AAC  TCC  GGA  AAC  TTC  GTA  GGT  GGA
       CCG  GTT  AAA  TCG  CAG  TTA  ACC  AGA  TTG  AGG  CCT  TTG  AAG  CAT  CCA  CCT
                             MunI    |          BspEI

TrX-3
       49   50   51   52   53   54   55   56   57   58   59   60   61   62   63   64
        K    G    W    Q    P    G    T    K    N    K    V    I    N    F    S    G
       AAA  GGT  TGG  CAA  CCC  GGG  ACC  AAA  AAT  AAG  GTG  ATC  AAC  TTC  TCT  GGA
       TTT  CCA  ACC  GTT  GGG  CCC  TGG  TTT  TTA  TTC  CAC  TAG  TTG  AAG  AGA  CCT
                             XmaI                          TrX-6

|
       65   66   67   68   69   70   71   72   73   74   75   76   77   78   79   80
        S    Y    N    P    N    G    N    S    Y    L    S    V    Y    G    W    S
       TCT  TAT  AAT  CCG  AAT  GGG  AAT  TCA  TAC  TTA  AGC  GTC  TAT  GGC  TGG  TCT
       AGA  ATA  TTA  GGC  TTA  CCC  TTA  AGT  ATG  AAT  TCG  CAG  ATA  CCG  ACC  AGA
         |                      EcoRI    AflII

XyTv-4                                                                |
       81   82   83   84   85   86   87   88   89   90   91   92   93   94   95
        R    N    P    L    I    E    Y    Y    I    V    E    N    F    G    T
       AGA  AAC  CCA  CTG  ATT  GAA  TAT  TAC  ATT  GTC  GAA  AAT  TTC  GGT  AC
       TCT  TTG  GGT  GAC  TAA  CTT  ATA  ATG  TAA  CAG  CTT  TTA  AAG  C
       Xba I          XyTv-5                                              |  KpnI
```

FIGURE 2

```
                                    XyTv-101
            92  93  94  95  96  97  98  99 100 101 102 103 104 105
         V   D   N   F   G   T   Y   N   P   S   T   G   A   T   K   L
        TC GAC AAT TTC GGT ACC TAC AAT CCG AGT ACC GGC GCC ACA AAA TTA
         3'- G  TTA AAG CCA TGG ATG TTA GGC TCA TGG CCG CGG TGT TTT AAT
        SalI |         KpnI           XyTv-110    KasI/NarI
```

```
                                                          XyTv-102
       106 107 108 109 110 111 112 113 114 115 116 117 118 119 120 121
        G   E   V   T   S   D   G   S   V   Y   D   I   Y   R   T   Q
       GGC GAA GTC ACT AGT GAT GGA TCC GTA TAT GAT ATC TAC CGT ACC CAA
       CCG CTT CAG TGA TCA CTA CCT AGG CAT ATA CTA TAG ATG GCA TGG GTT
                      SpeI        BamHI         |             XyTv-109
                              |                 TrX-103
       122 123 124 125 126 127 128 129 130 131 132 133 134 135 136 137
        R   V   N   Q   P   S   I   I   G   T   A   T   F   Y   Q   Y
       CGC GTT AAT CAG CCA TCG ATC ATT GGA ACC GCC ACC TTT TAT CAG TAC
       GCG CAA TTA GTC GGT AGC TAG TAA CCT TGG CGG TGG AAA ATA GTC ATG
       MluI            ClaI                                      |
```

```
                                            |
       138 139 140 141 142 143 144 145 146 147 148 149 150 151 152 153
        W   S   V   R   R   N   H   R   S   S   G   S   V   N   T   A
       TGG AGT GTT AGA CGT AAT CAT CGG AGC TCC GGT TCG GTT AAT ACT GCG
       ACC TCA CAA TCT GCA TTA GTA GCC TCG AGG CCA AGC CAA TTA TGA CGC
          TrX-108                            SacI                      |
```

```
              XyTv-104                                                   |
       154 155 156 157 158 159 160 161 162 163 164 165 166 167 168 169
        N   H   F   N   A   W   A   Q   Q   G   L   T   L   G   T   M
       AAT CAC TTT AAT GCA TGG GCA CAG CAA GGG TTA ACC CTA GGT ACA ATG
       TTA GTG AAA TTA CGT ACC CGT GTC GTT CCC AAT TGG GAT CCA TGT TAC
                        NsiI       XyTv-107                AvrII
```

```
                        XyTv-105
       170 171 172 173 174 175 176 177 178 179 180 181 182 183 184 185
        D   Y   Q   I   V   A   V   E   G   Y   F   S   S   G   S   A
       GAT TAT CAA ATC GTA GCG GTG GAA GGC TAC TTC TCG AGT GGT TCC GCT
       CTA ATA GTT TAG CAT CGC CAC CTT CCG ATG AAG AGC TCA CCA AGG CGA
                               |   XyTv-106           XhoI
```

```
                    |
       186 187 188 189 190
        S   I   T   V   S    (SEQ ID NO:39)
       AGT ATT ACA GTG AGC TAA A  (SEQ ID NO:56)
       TCA TAA TGT CAC TCG ATT TCT AG-5' (SEQ ID NO:57)
                               BglII |
```

FIGURE 2 CONT'D

MODIFIED XYLANASES EXHIBITING INCREASED THERMOPHILICITY AND ALKALOPHILICITY

This application is a divisional application of application Ser. No. 10/307,441 filed Dec. 2, 2002 now abandoned, which is a U.S. national phase of PCT International application No. PCT/CA01/00769 filed May 31, 2001, which claims the benefit of U.S. provisional application No. 60/213,803 filed May 31, 2000. The contents of these applications are incorporated herein by reference in their entireties.

The present invention relates to modified xylanases. More specifically, the invention relates to modified xylanases with improved performance at conditions of high temperature and pH.

BACKGROUND OF THE INVENTION

Xylanases are a group of enzymes with wide commercial utility. A major application of xylanases is for pulp biobleaching in the production of paper. In addition, xylanases have been used as clarifying agents in juices and wines, as enzymatic agents in the washing of precision devices and semiconductors (e.g. U.S. Pat. No. 5,078,802), and they are also used for improving digestibility of poultry and swine feed.

In the manufacturing of pulp for the production of paper, fibrous material is subjected to high temperatures and pressures in the presence of chemicals. This treatment converts the fibers to pulp and is known as pulping. Following pulping, the pulp is bleached. Xylanase enzymes are used to enhance the bleaching of the pulp. The xylanase treatment allows subsequent bleaching chemicals such as chlorine, chlorine dioxide, hydrogen peroxide, or combinations of these chemicals to bleach pulp more efficiently. Pretreatment of pulp with xylanase increases the whiteness and quality of the final paper product and reduces the amount of chlorine-based chemicals which must be used to bleach the pulp. This in turn decreases the chlorinated effluent produced by such processes.

The most important chemical pulping process is kraft pulp. For kraft pulp, following pulping, and prior to the treatment of pulp with xylanase, the pulp is at about a temperature of 55-70° C. and at a highly alkaline pH (e.g. Nissen et al., 1992). A drawback of many commercially available wild-type xylanases, is that these enzymes exhibit an acidic pH optimum and a temperature optimum of about 55° C. Therefore, in order to effectively utilize xylanases for bleaching applications, the pulp must be acidified to a pH approximating the optimal pH for the specific xylanase used. In addition, the hot pulp must be cooled to a temperature close to the optimal temperature for enzymatic activity of the selected xylanase. Decreasing pulp temperatures for xylanase treatment decreases the efficiency of the subsequent chemical bleaching. Acidification of pulp requires the use of large quantities of acids. Further, the addition of acids leads to corrosion, which lessens the lifetime of process equipment. Thus, xylanases optimally active at temperatures and pH conditions approximating the conditions of the pulp would be useful and beneficial in pulp manufacturing.

Xylanases which exhibit greater activity at higher temperatures could be used to treat pulp immediately following the pulping process, without the need to cool the pulp. Similarly, xylanases which exhibit greater activity at higher pH conditions would require less or no acid to neutralize the pulp. The isolation of, or the genetic manipulation of, xylanases with such properties would provide several advantages and substantial economic benefits within a variety of industrial processes.

Several approaches directed towards improving xylanase for use in pulp-bleaching within the prior art include the isolation of thermostable xylanases from extreme thermophiles that grow at 80-100° C., such as *Caldocellum saccharolyticum, Thermatoga maritima* and *Thermatoga* sp. Strain FJSS-B.1 (Lüthi et al. 1990; Winterhalter et al. 1995; Simpson et al. 1991). However, these thermostable xylanase enzymes are large, with molecular masses ranging from 35-120 kDa (320-1100 residues), and exhibit a reduced ability to penetrate the pulp mass compared with other smaller xylanases which exhibit better accessibility to pulp fibers. In addition, some of the extremely thermophilic xylanases, such as *Caldocellum saccharolyticum* xylanase A, exhibit both xylanase and cellulase activities (Lüthi et al. 1990). This additional cellulolytic activity is undesirable for pulp bleaching, due to its detrimental effect on cellulose, the bulk material in paper. Furthermore, hyper-thermostable xylanase enzymes which function normally at extremely high temperatures have low specific activities at temperatures in the range for optimal pulp bleaching (Simpson et al. 1991).

A number of xylanases have been modified by protein engineering to improve their properties for industrial applications. For instance, U.S. Pat. No. 5,759,840 (Sung et al.), and U.S. Pat. No. 5,866,408 (Sung et al.) disclose mutations in the N-terminal region (residues 1-29) of *Trichoderma reesei* xylanase II (TrX). Three mutations, at residues 10, 27 and 29 of TrX, were found to increase the enzymatic activity of the xylanase enzyme at elevated temperatures and alkaline pH conditions.

U.S. Pat. No. 5,405,769 (Campbell et al.) discloses the modification of *Bacillus circulans* xylanase (BcX) using site-directed mutagenesis to improve the thermostability of the enzyme. The site specific mutations include replacing two amino acids with Cys residues to create intramolecular disulfide bonds. In addition, specific residues in the N-terminus of the enzyme were mutated which were also found to further improve the thermostability of the enzyme. In in vitro assays, the disulfide mutants showed thermostability at 62° C., an improvement of 7° C. over the native BcX xylanase enzyme. However, these thermostable disulfide mutants showed no gain in thermophilicity in laboratory assays in subsequent studies (Wakarchuck et al., 1994). Mutations T3G (i.e. threonine at position 3 replaced with Gly; BcX xylanase amino acid numbering), D4Y(F) and N8Y(F) near the N-terminus of the BcX xylanase enzyme provided thermostability to 57° C., an increase of 2° C. over the native BcX (U.S. Pat. No. 5,405,769). However, the use of these enzymes within industrial applications still requires cooling and acidification of pulp following pretreatment, prior to enzyme addition. Therefore, further increases in thermostability, thermophilicity and pH optima are still required.

There is a need in the prior art to obtain novel xylanases which exhibit increased enzymatic activity at elevated temperatures and pH conditions, suitable for industrial use. It is an object of the invention to overcome drawbacks in the prior art.

The above object is met by the combination of features of the main claim, the sub-claims disclose further advantageous embodiments of the invention.

SUMMARY OF THE INVENTION

The present invention relates to modified xylanases. More specifically, the invention relates to modified xylanases with improved performance at conditions of high temperature and pH.

This invention relates to a modified xylanase comprising at least one substituted amino acid residue at a position selected from the group consisting of amino acid 75, 104, 105, 125, 129, 132, 135, 144, 157, 161, 162, and 165 the position determined from sequence alignment of the modified xylanase with *Trichoderma reesei* xylanase II amino acid sequence defined in SEQ ID NO:16. Preferably, the modified xylanase exhibits improved thermophilicity, alkalophilicity, or a combination thereof, in comparison to a corresponding native xylanase.

The present invention also provides for the modified xylanase as defined above wherein the at least one substituted amino acid residue is at position 75. Preferably the substituted amino acid is selected from the group consisting of Ala, Cys, Gly, and Thr.

The present invention also embraces the modified xylanase as defined above and further comprising a His at position 10, Met at position 27 and Leu at position 29.

According to the present invention there is also provided a modified xylanase comprising a substituted amino acid residue at position 105, the position determined from sequence alignment with *Trichoderma reesei* xylanase II amino acid sequence defined in SEQ ID NO:16. Preferably, the substituted amino acid is selected from the group consisting of His, Lys, and Arg. The present invention also pertains to the modified xylanase just defined further comprising a His at position 10, Met at position 27 and Leu at position 29. The invention also includes the modified xylanase just defined further comprising a substituted amino acid residue at position 75.

This invention also includes a modified xylanase comprising a His at position 10, a Met at position 27, a Leu at position 29, a non-polar amino acid at positions 75 and 125, a non-polar amino acid at position 104, a polar amino acid at position 105, and an acidic amino acid at position 129. Preferably, the amino acid at position 75 is Ala, the amino acid at position 125 is selected from the group consisting of Ala, Cys, Gly, and Thr, the amino acid at position 125 is Glu. The amino acid at position 105 is selected from the group consisting of His, Lys, and Arg, and the amino acid residue at position 104 is Pro.

This invention further relates to a modified xylanase comprising a His at position 10, a Met at position 27, a Leu at position 29, a non-polar amino acid at positions 75 and 125, a polar amino acid at positions 105, 132 and 135, and an acidic amino acid at position 129. Furthermore, the modified xylanase as just defined may include a polar amino acid at position 144.

This invention includes a modified xylanase comprising a His at position 10, a Met at position 27, a Leu at position 29, a non-polar amino acid at positions 75 and 125, a polar amino acid at positions 105, 132, 135, 144, 157, 161, 162 and 165, and an acidic amino acid at position 129.

This invention embraces a modified xylanase comprising a His at position 10, a Met at position 27, a Leu at position 29, a non-polar amino acid at positions 75 and 125, a polar amino acid at positions 105, 132, 135, 157, 161, 162 and 165, and an acidic amino acid at position 129.

This invention also pertains to a modified xylanase comprising a His at position 10, a Met at position 27, a Leu at position 29, a non-polar amino acid at positions 75 and 125, and a polar amino acid at positions 105, 135, 144, 157, 161, 162 and 165.

The present invention is also directed to the modified xylanases, as defined above, wherein the modified xylanases are derived from a Family 11 xylanase, preferably a *Trichoderma reesei* xylanase.

The present invention pertains to a modified xylanase comprising at least one substituted amino acid residue, wherein the modified xylanase is characterized as having a maximum effective temperature (MET) between about 69° C. to about 78° C., and wherein the modified xylanase is a Family 11 xylanase obtained from a *Trichoderma* sp. Preferably, the MET is between about 70° to about 75° C.

This invention also includes a modified xylanase comprising at least one substituted amino acid residue, wherein the modified xylanase is characterized as having a maximum effective pH (MEP) between about pH 5.8 to about pH 7.6, and wherein the modified xylanase is a Family 11 xylanase obtained from a *Trichoderma* sp. Preferably, the MEP is between about pH 6.5 to about pH 7.4.

The present invention is directed to a modified xylanase comprising at least one substituted amino acid residue, wherein the modified xylanase is characterized as having a maximum effective temperature (MET) between about 69° C. to about 78° C., and a maximum effective pH (MEP) between about pH 5.8 to about pH 7.6. Preferably, the MET is between about 70° to about 75° C., and the MEP is between about pH 6.5 to about pH 7.4.

The present invention also relates to a modified xylanase selected from the group consisting of:

TrX-75A
TrX-157D-161R-162H-165H;
TrX-75A;
TrX-HML-105H;
TrX-HML-105R;
TrX-HML-105K;
TrX-HML-75A-105H;
TrX-HML-75A-105R;
TrX-HML-75C-105R;
TrX-HML-75G-105R;
TrX-HML-75T-105R
TrX-HML-125A;
TrX-HML-125A-129E;
TrX-HML-75G-105R-125A-129E (TrX-HML-GRAE);
TrX-HML-75A-105H-125A-129E (TrX-HML-AHAE);
TrX-HML-75G-105H-125A-129E (TrX-HML-GHAE);
TrX-HML-75A-105R-125A-129E (TrX-HML-ARAE);
TrX-HML-75G-104P-105R-125A-129E (TrX-HML-GPRAE);
TrX-HML-75G-104P-105H-125A-129E (TrX-HML-GPHAE);
TrX-HML-AHAE-RR;
TrX-HML-AHAE-RRR;
TrX-HML-AHAE-RRR-DRHH;
TrX-HML-AHA-RR-DRHH; and
TrX-HML-AHAE-RR-DRHH.

According to the present invention, there is provided a modified xylanase comprising at least one substituted amino acid residue, and characterized as having a maximum effective temperature (MET) between about 69° C. to about 78° C., wherein the modified xylanase is a Family 11 xylanase obtained from a *Trichoderma* sp. Furthermore the present invention relates to a modified Family 11 xylanase obtained from a *Trichoderma* sp. characterized as having a MET between about 70° to about 75° C. The present invention also includes the modified Family 11 xylanase obtained from a *Trichoderma* sp. characterized as having a MET between about 69° C. to about 78° C. and a maximum effective pH (MEP) between about 5.8 to about 7.6. This invention also pertains to the modified xylanase as just defined, wherein the MEP is between about 6.5 to about 7.4.

The present invention is directed to the use of the modified xylanase as defined above in an industrial process. Also included is an industrial process, wherein the industrial process comprises bleaching of pulp, processing of precision devices, or improving digestibility of poultry and swine feed.

This summary of the invention does not necessarily describe all necessary features of the invention but that the invention may also reside in a subcombination of the described features.

BRIEF DESCRIPTION OF THE DRAWINGS

These and other features of the invention will become more apparent from the following description in which reference is made to the appended drawings wherein:

FIG. 1 shows an amino acid sequence alignment among Family 11 xylanases, where Bp—*Bacillus pumilus* (SEQ ID NO:4); Ca—*Clostridium acetobutylicum* P262 XynB (SEQ ID NO:6); Cs—*Clostridium stercorarium* xynA (SEQ ID NO:7); Rf—*Ruminococcus flavefaciens* (SEQ ID NO:8); Tr2—*Trichoderma reesei* xyn2 (SEQ ID NO:16); Tv—*Trichoderma viride* (SEQ ID NO:17); Th—*Trichoderma harzianum* (SEQ ID NO:14); Sc—*Schizophyllum commune* xynA (SEQ ID NO:9); An—*Aspergillus niger*, var. *awamori* (SEQ ID NO:1); At—*Aspergillus tubigensis* (SEQ ID NO:2); Tr1—*Trichoderma reesei* xyn1 (SEQ ID NO:15); Aa—*Aspergillus awamori* var. *kawachi* xyn B (SEQ ID NO:19); Fs—*Fibrobacter succinogenes* xyn II (SEQ ID NO:18); Ss—*Streptomyces* sp. 36a (SEQ ID NO:12); S1B—*Streptomyces lividans* xynB (SEQ ID NO:10); S1C—*Streptomyces lividans* xynC (SEQ ID NO:11); T1—*Thermomyces lanuginosus* xyn (SEQ ID NO:20); Tf—*Thermomonospora fusca* TfxA (SEQ ID NO:13); Bc—*Bacillus circulans* (SEQ ID NO:3); and Bs—*Bacillus subtilis* (SEQ ID NO:5). The amino acid numbering is compared with *Trichoderma reesei* xylanase II (Tr2) as indicated at the top of the sequences. The residues at position 75 and 105 (relative to Tr2) are in italics and indicated with an asterisk. The amino acids common to at least 75% of the listed Family 11 xylanases are indicated in bold. The residues common to all Family 11 xylanases are underlined. For xylanases with a cellulose-binding domain, only the catalytic core sequences are presented.

FIG. 2 shows the nucleotide sequence of TrX xylanase (SEQ ID NO:39), and the synthetic oligonucleotides TrX(1-91) and TrX (92-190) (SEQ ID NOs:54 to 57) used to construct the sequence encoding the *Trichoderma reesei* xylanase II enzyme (TrX) in the plasmid pTrX.

at pH 5.5 during 30 min incubations. The data are normalized to the activity observed at 40° C.

Figure 9:
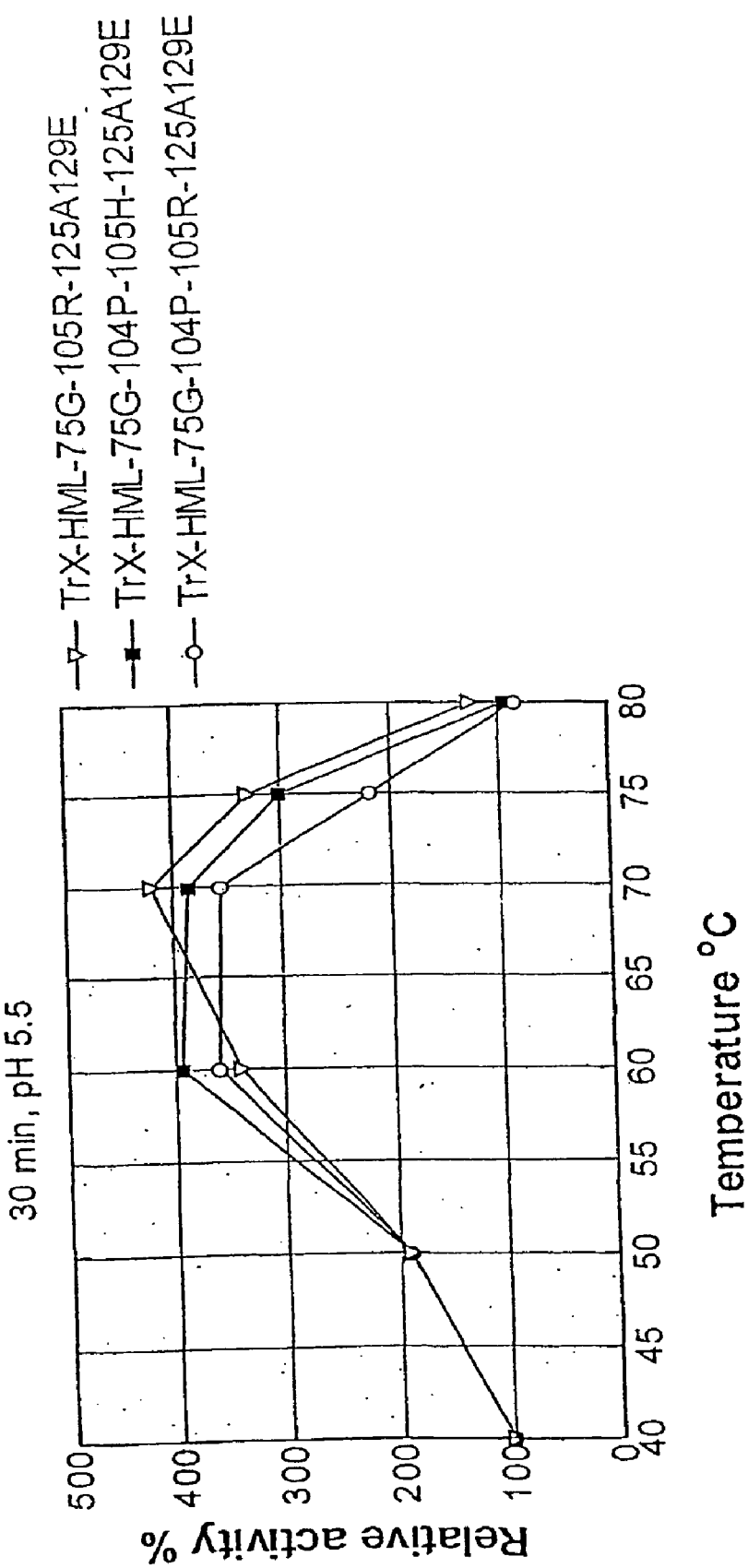

FIG. 9 shows the effect of temperature on the enzymatic activity of modified xylanase enzymes:
TrX-HML-75G-104P-105R-125A129E (TrX-HML-GPRAE);
TrX-HML-75G-104P-105H-125A129E (TrX-HML-GPHARE); and
TrX-HML-75G-105R-125A129E (TrX-HML-GRAE)

at pH 5.5 during 30 min incubations. The data are normalized to the activity observed at 40° C.

Figure 10:
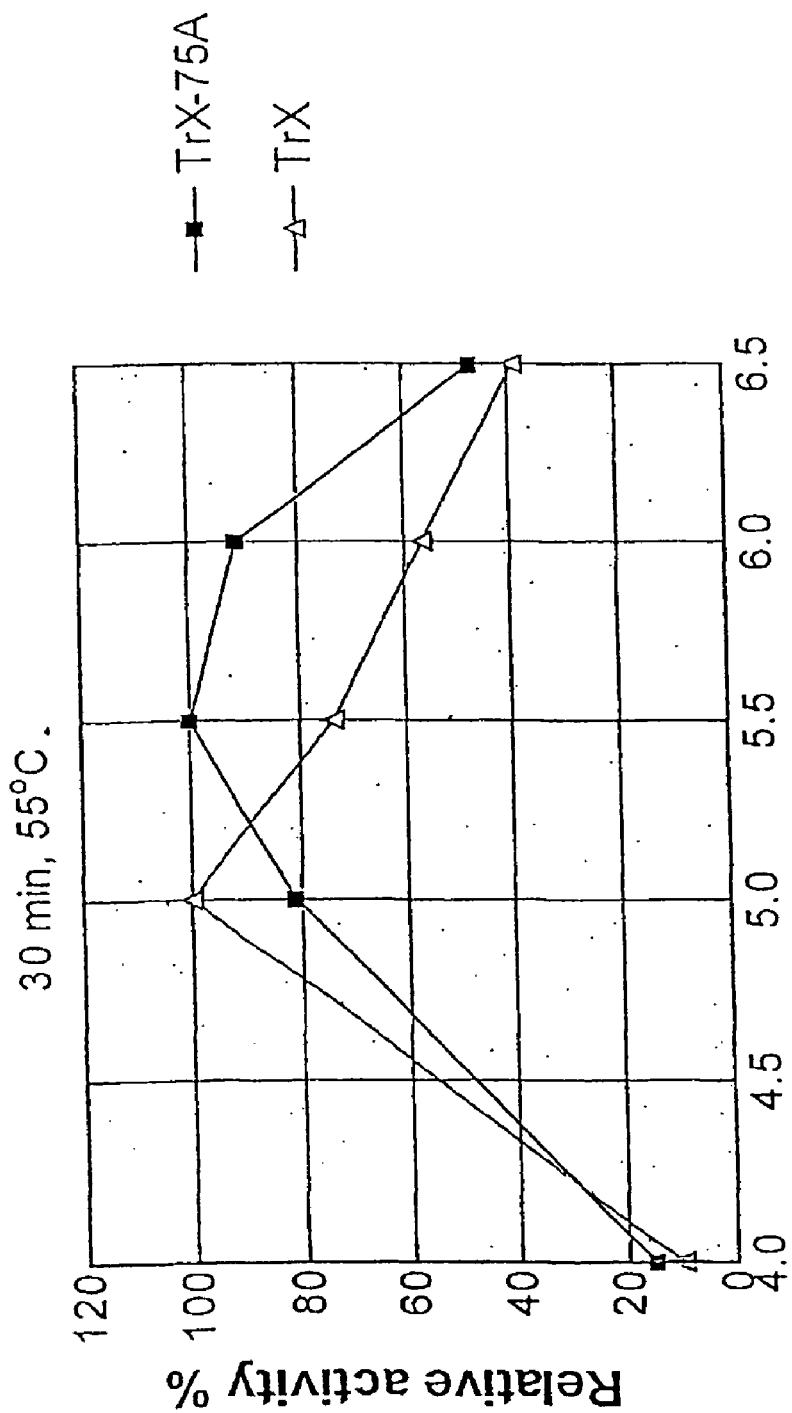

FIG. 10 shows the pH profile of modified xylanase enzyme TrX-75A compared with native TrX, over pH 4.0-6.5, at 55° C. during 30 min incubation. The data are normalized to the pH exhibiting optimal activity for each enzyme.

Figure 11:
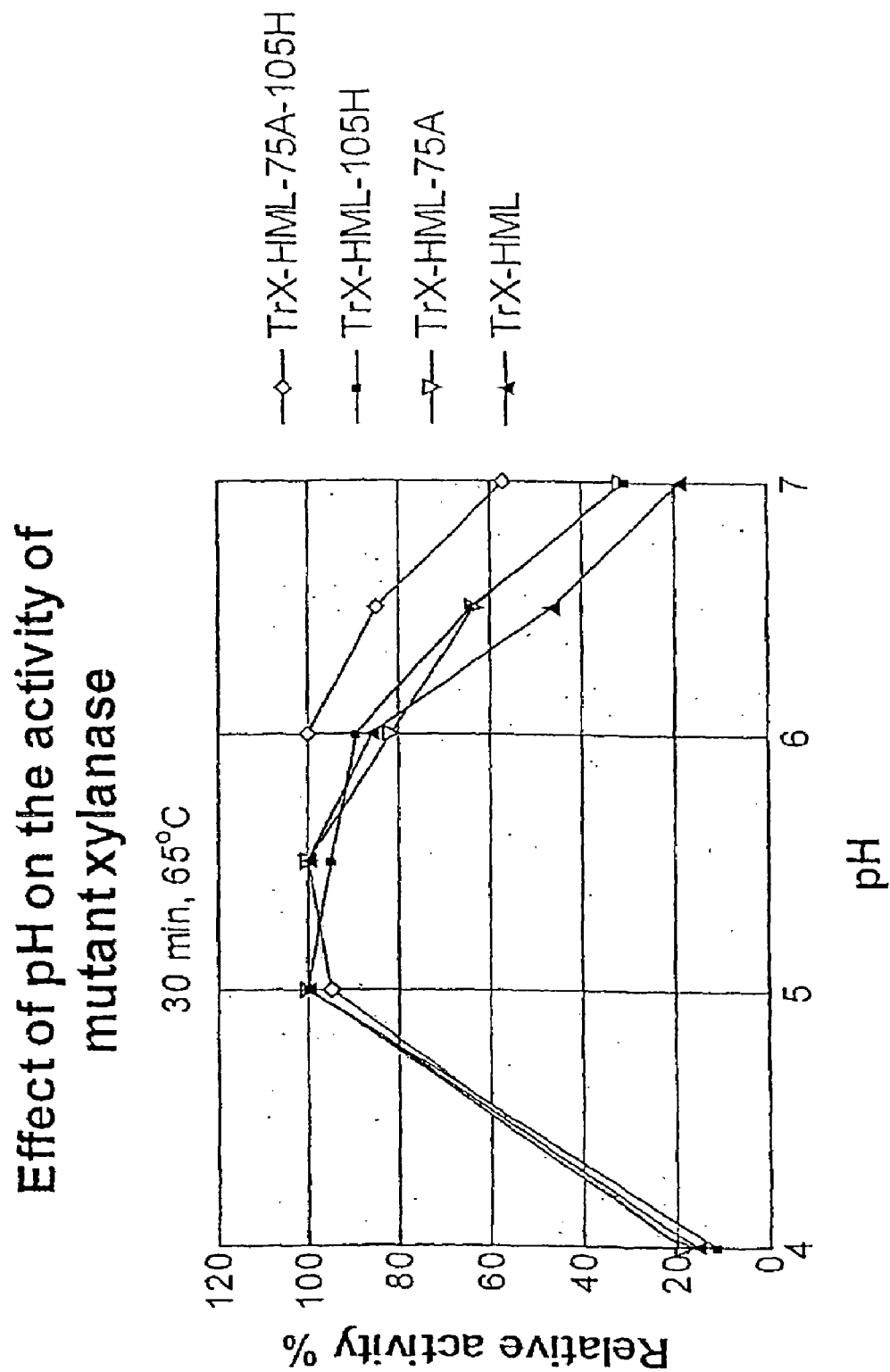

FIG. 11 shows the pH profiles of modified xylanases TrX-HML, TrX-HML-75A, TrX-HML-105H and TrX-HML-75A-105H over pH 4-7, at 65° C. during 30 min incubation. The data are normalized to the pH exhibiting optimal activity for each enzyme.

Figure 12:
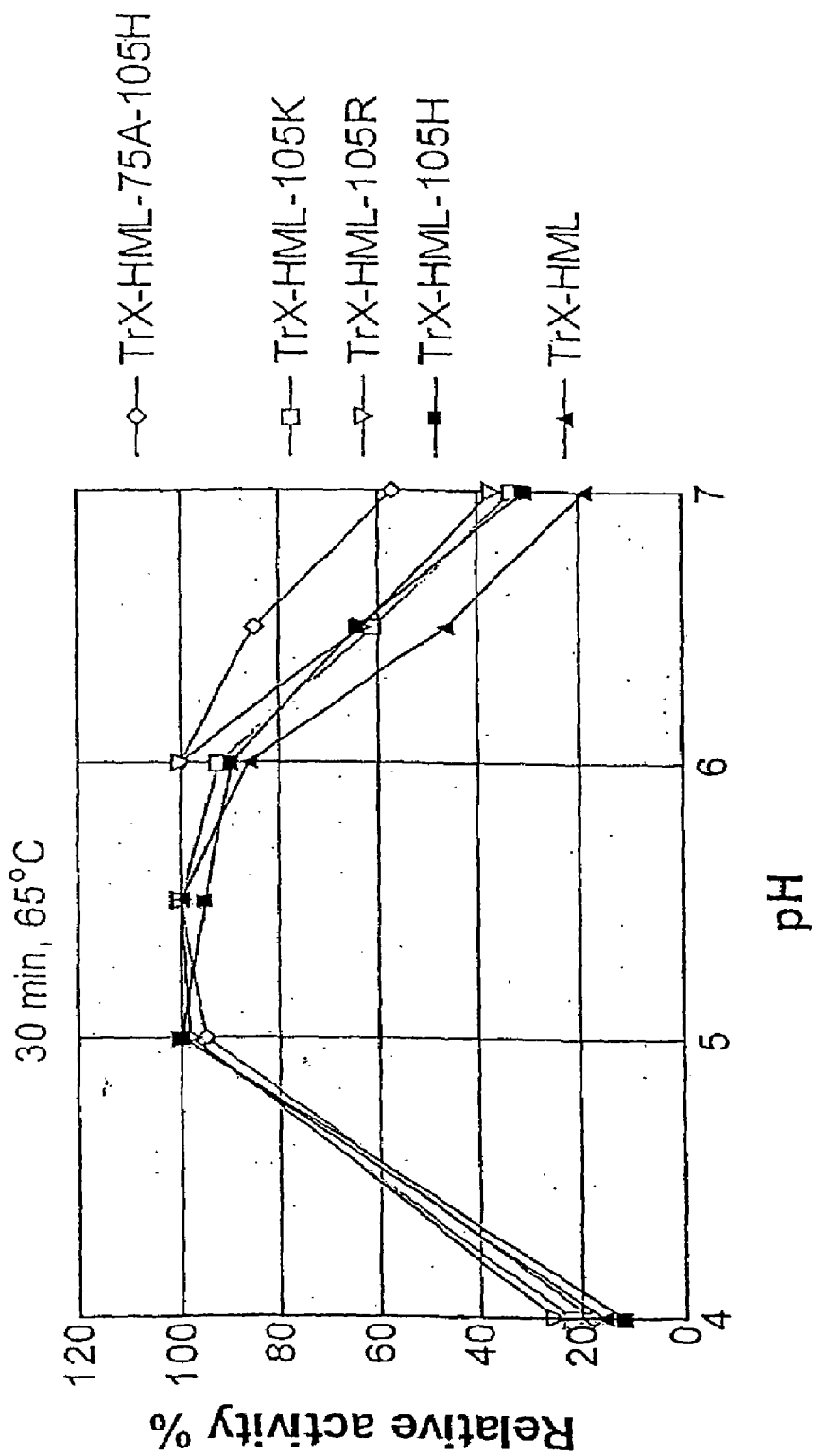

FIG. 12 shows the pH profile of modified xylanases TrX-HML, TrX-HML-105K, TrX-HML-105R, TrX-HML-105H and TrX-HML-75A-105H over pH 4-7, at 65° C. during 30 min incubation. The data are normalized to the pH exhibiting optimal activity for each enzyme.

Figure 13:
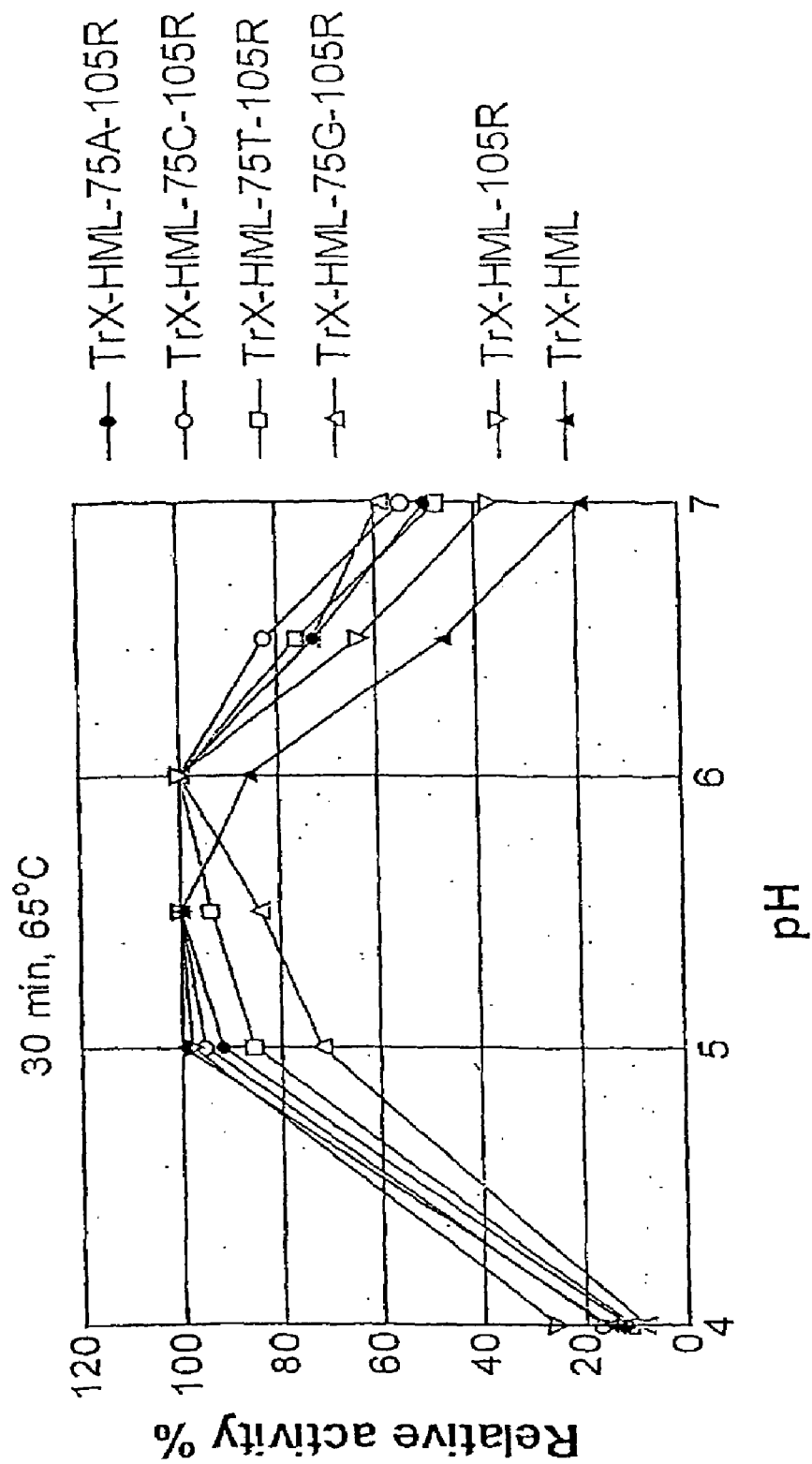

FIG. 13 shows the pH profile of modified xylanases:
TRX-HML;
TrX-HML-105R;
TrX-HML-75T-105R, TrX-HML-75G-105R;
TrX-HML-75A-105R; and
TrX-75C-105R over pH 4-7, at 65° C. during 30 min incubations. The data are normalized to that observed at the pH for optimal activity of the enzyme.

Figure 14:
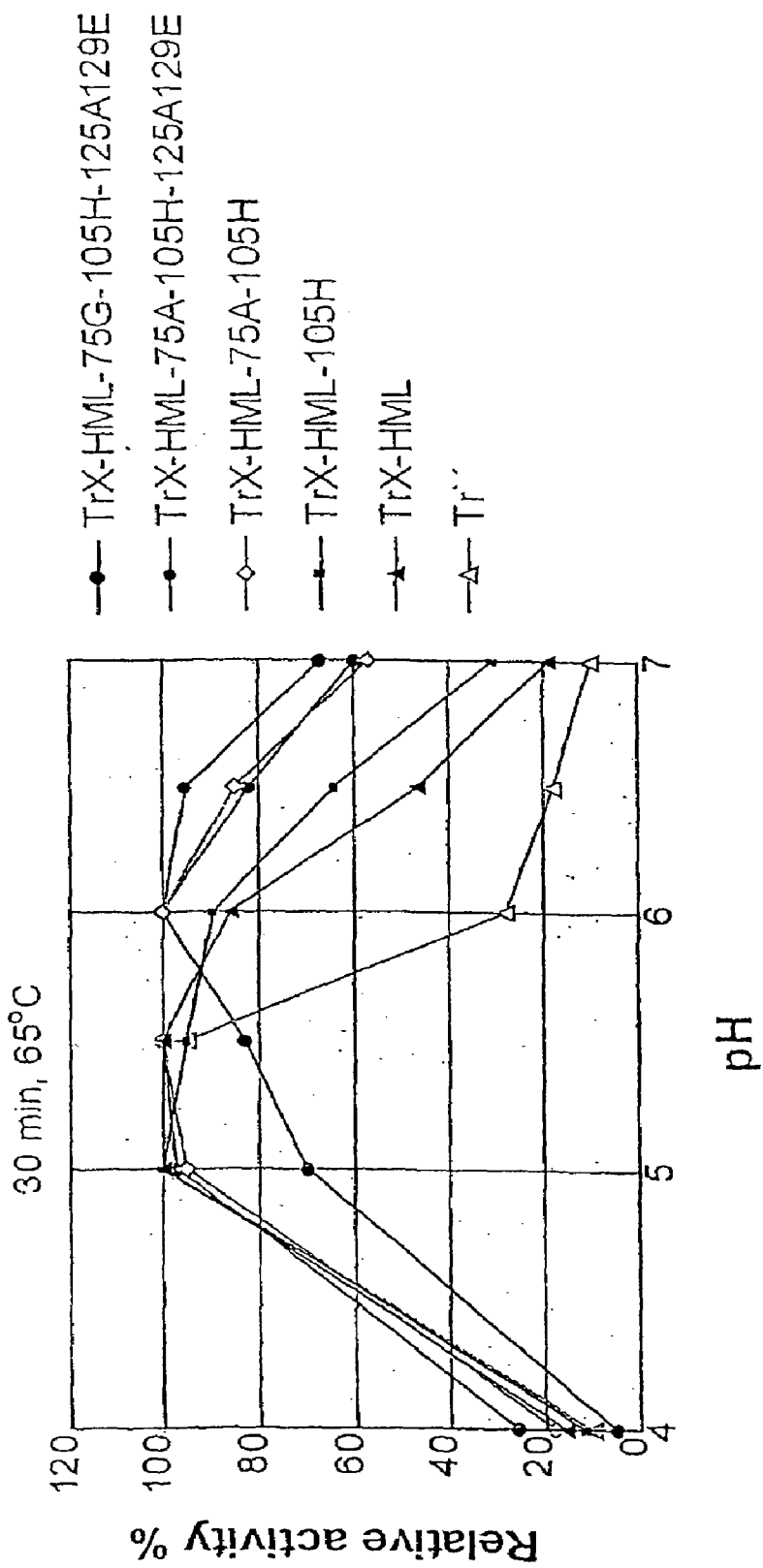

FIG. 14 shows the pH profile of modified xylanases:
TrX-HML;
TrX-HML-105H;
TrX-HML-75A-105H;
TrX-HML-75A-105H-125A129E (TrX-HML-AHAE); and
TrX-HML-75G-105H-125A129E (TrX-HML-GHAE)

over pH 4-7, at 65° C. during 30 min incubations. The data are normalized to the pH exhibiting optimal activity for each enzyme.

Figure 15:
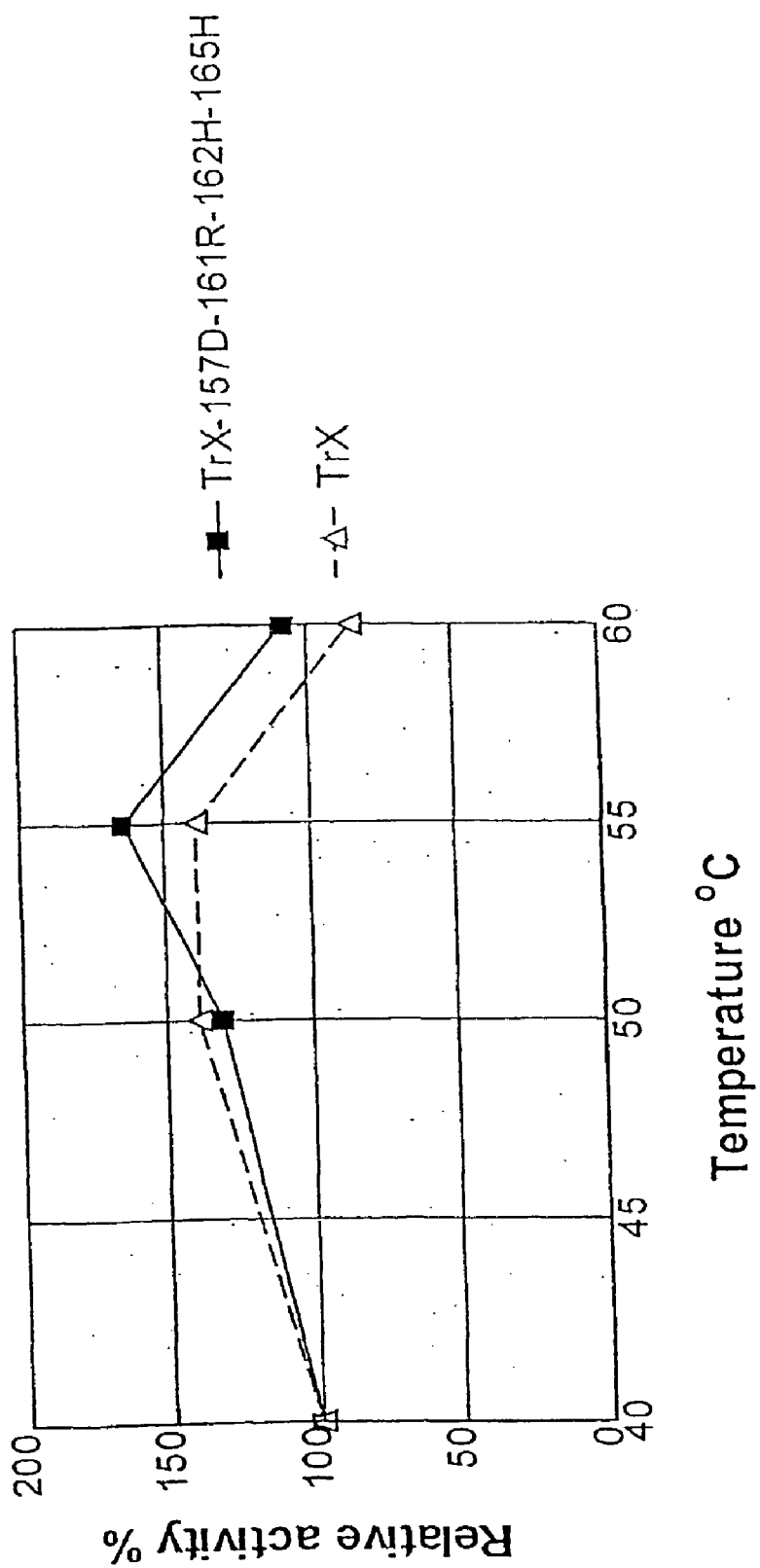

FIG. 15 shows the effect of temperature on the enzymatic activity of modified xylanase TrX-157D-161R-162H-165H, compared with TrX, at pH 5.5 during 30 min incubations. The data are normalized to the activity observed at 40° C.

Figure 16:
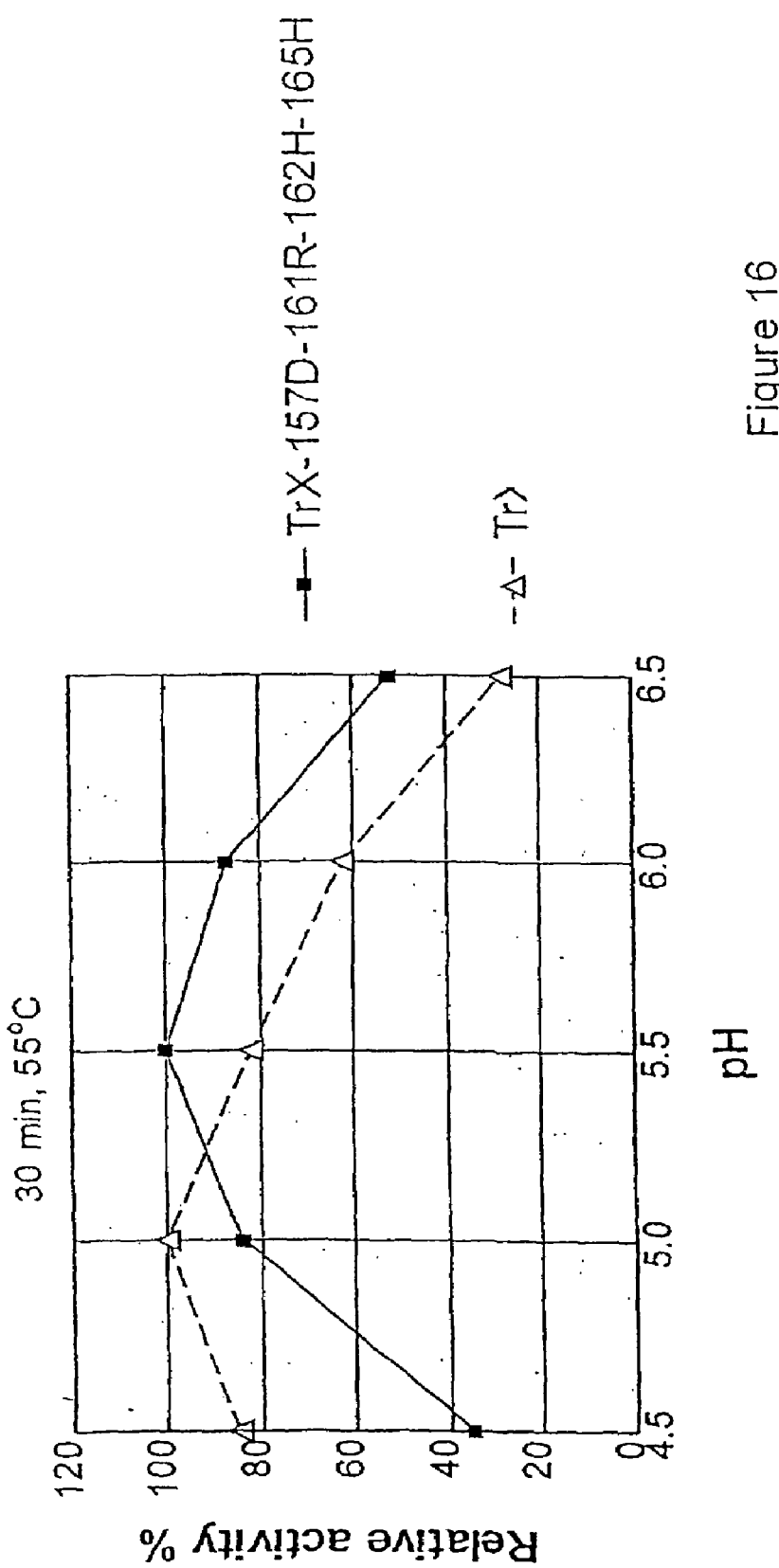

FIG. 16 shows the pH profile of modified xylanase enzyme TrX-157D-161R-162H-165H compared with native TrX, over pH 4.0-6.5, at 55° C. during 30 min incubation. The data are normalized to the pH exhibiting optimal activity for each enzyme.

Figure 17:
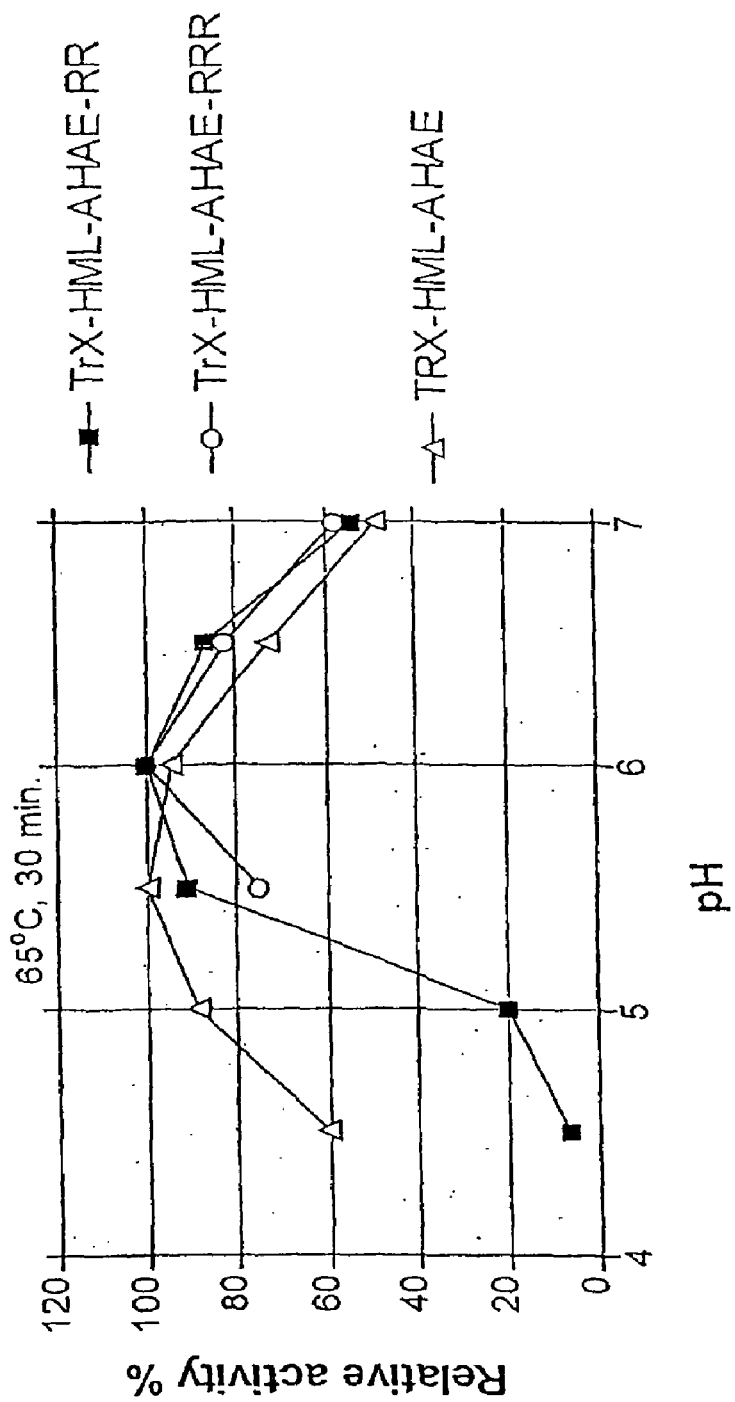

FIG. 17 shows the effect of temperature on the enzymatic activity of modified xylanases:
TrX-HML-AHAE-RR; and
TrX-HML-AHAE-RRR at pH 5.5 during 30 min incubations. The data are normalized to the activity observed at 40° C.

Figure 18:
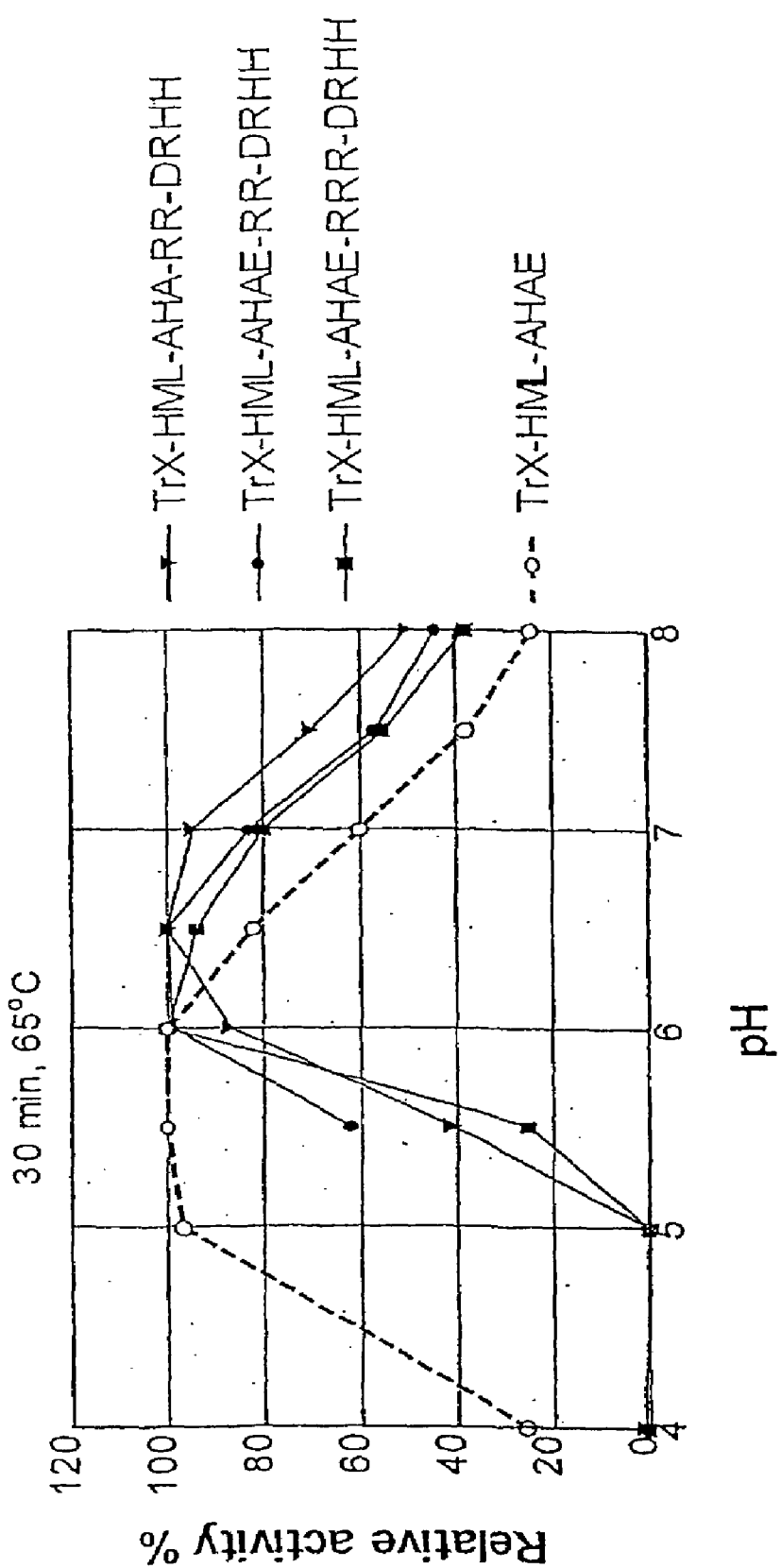

FIG. 18 shows the effect of temperature on the enzymatic activity of modified xylanases:
TrX-HML-AHA-RR-DRHH;
TrX-HML-AHAE-RR-DRHH; and
TrX-HML-AHAE-RRR-DRHH at pH 5.5 during 30 min incubations. The data are normalized to the activity observed at 40° C.

Figure 19:
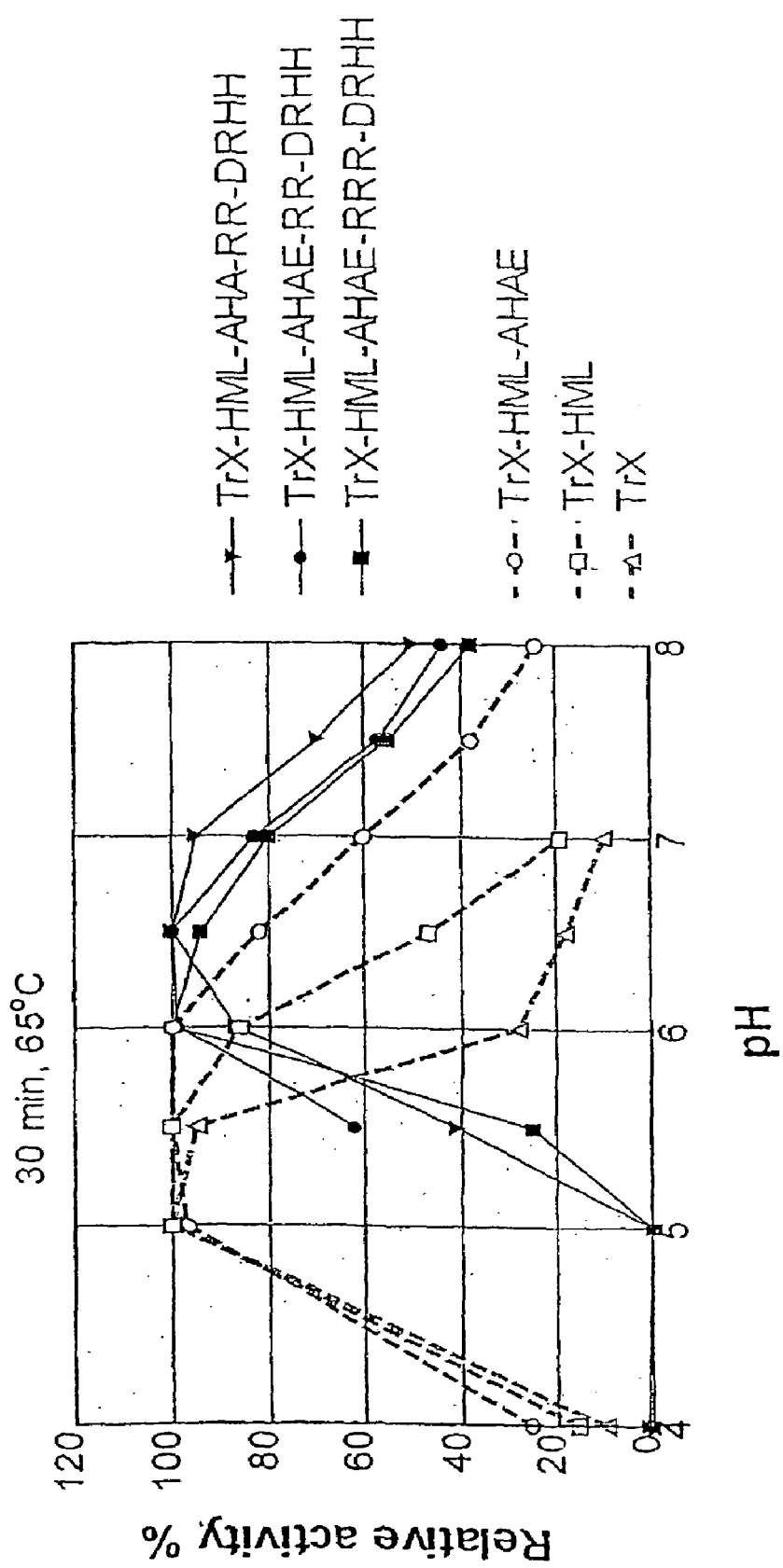

FIG. 19 shows the effect of temperature on the enzymatic activity of modified xylanases:
TrX;
TRX-HML
TrX-HML-AHAE
TrX-HML-AHAE-RRR-DRHH;
TrX-HML-AHA-RR-DRHH; and
TrX-HML-AHAE-RR-DRHH at pH 5.5 during 30 min incubations. The data are normalized to the activity observed at 40° C.

Figure 20:
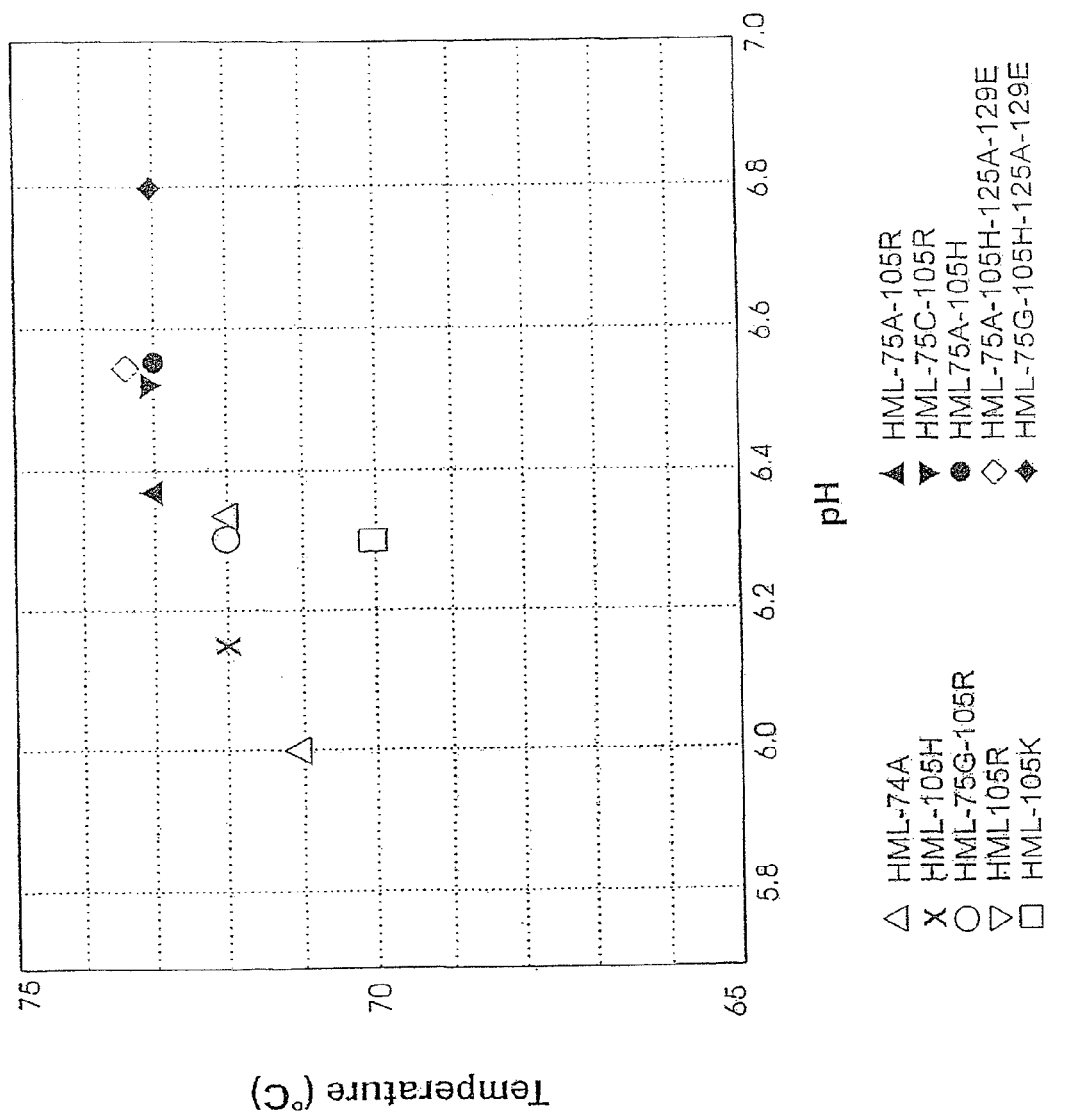

FIG. 20 shows the maximum effective temperature (MET) and maximum effective pH (MEP) values of several of the modified enzymes of the present invention. The MET and MEP are the highest temperature and pH, respectively, at which a xylanase exhibits at least 80% of its optimal activity (using xylan as a substrate; see method for complete details of assays). These data points were obtained from the data presented in FIGS. 5 to 14.

DESCRIPTION OF PREFERRED EMBODIMENT

The present invention relates to modified xylanases. More specifically, the invention relates to modified xylanases with improved performance at conditions of high temperature and pH.

The following description is of a preferred embodiment by way of example only and without limitation to the combination of features necessary for carrying the invention into effect.

The mechanism by which xylanases facilitate bleaching of pulp is not fully understood. It has been postulated that the coloured lignin is connected to crystalline cellulose through xylan and xylanase enzymes facilitate bleaching of pulp by hydrolysing xylan, releasing coloured lignin in the pulp. Modified xylanases, as outlined herein, may be used for the purposes of bleaching pulp or other applications requiring activities at temperatures and pH above that of the wild-type enzyme. For the biobleaching of pulp, the preferred xylanase is derived from a xylanase classified in Family 11 (see Table 1); however, the modifications disclosed herein need not be limited to only Family 11 xylanases and may include other xylanase enzymes.

Family 11 xylanase enzymes are a group of small enzymes of relatively low molecular mass (approximately 20 kDa, and about 200 amino acid residues. The small size associated with Family 11 xylanases permits ready penetration of the pulp mass. Furthermore, Family 11 xylanases are free of cellulase activity.

One aspect of the present invention is directed to a modified Family 11 xylanase obtained from a *Trichoderma* sp. comprising at least one substituted amino acid residue, and characterized as having a maximum effective temperature (MET) between about 69° C. to about 78° C. Preferably, the modified xylanase is characterized as having a MET between about 70° to about 75° C. This invention also includes a modified xylanase comprising at least one substituted amino acid residue, and is characterized as having a maximum effective pH (MEP) between about 5.8 to about 7.6. Preferably, the MEP is between about 6.5 to about 7.4.

This invention also pertains to a modified xylanase obtained from *Trichoderma*, comprising at least one substituted amino acid, and characterized as having a maximum effective temperature (MET) between about 69° C. to about 78° C., and a maximum effective pH (MEP) is between about 5.8 to about 7.6. Preferably the MET is between about 70° to about 75° C., and the MEP is between about 6.5 to about 7.4.

By "maximum effective temperature" or "MET" it is meant the highest temperature at which a xylanase exhibits at least 80% of its optimal activity. This test is typically carried out using xylan as a substrate at pH 5.5, and for a 30 min period. Results from assays used to characterize modified xylanases are presented in FIGS. 3 to 9 and involved a 30 min incubation at pH 5.5. A summary of the MET of several enzymes of the present invention, determined from FIGS. 3 to 9 is presented in FIG. 20. Experiments demonstrate that the MET of a xylanase differs on different substrates. Therefore, it is to be understood that with different substrates, different MET values will be obtained (data not presented). For the purposes of evaluating xylanases of the present invention, the xylan substrate is used (see Examples 3 and 4).

By "maximum effective pH" or "MEP" it is meant the highest pH at which a xylanase exhibits at least 80% of its optimal activity. This test is carried out using xylan as a substrate, at 65° C., and for a 30 min period. Results from assays used to characterize modified xylanases are presented in FIGS. 10 to 14 and 16 to 19 and involved a 30 min incubation at 65° C. A summary of the MEP of several enzymes of the present invention is presented in FIG. 20. Experiments demonstrate that the MEP of a xylanase differs on different substrates. For example, on kraft pulp prepared from soft wood or hardwood, a MEP of 8.5 has been observed (data not presented). Therefore, it is to be understood that with different substrates, different MEP values will be obtained. For the purposes of evaluating xylanases of the present invention, the xylan substrate is used (see Examples 4 and 5).

TABLE 1

Family 11 xylanase enzymes

| Microbe | Xylanase | SEQ ID NO |
|---|---|---|
| *Aspergillus niger* | Xyn A | SEQ ID NO: 1 |
| *Aspargillus awamori* var. *kawachi* | Xyn B | SEQ ID NO: 19 |
| *Aspergillus kawachii* | Xyn C | — |
| *Aspergillus tubigensis* | Xyn A | SEQ ID NO: 2 |
| *Bacillus circulans* | Xyn A | SEQ ID NO: 3 |
| *Bacillus pumilus* | Xyn A | SEQ ID NO: 4 |
| *Bacillus subtilis* | Xyn A | SEQ ID NO: 5 |
| *Cellulomonas fimi* | Xyn D | — |
| *Chainia* spp. | Xyn | — |
| *Clostridium acetobutylicum* | Xyn B | SEQ ID NO: 6 |
| *Clostridium stercorarium* | Xyn A | SEQ ID NO: 7 |
| *Fibrobacter succinognees* | Xyn II | SEQ ID NO: 18 |
| *Neocallimasterix patriciarum* | Xyn A | — |
| *Nocardiopsis dassonvillei* | Xyn II | — |
| *Ruminococcus flavefaciens* | Xyn A | SEQ ID NO: 8 |
| *Schizophyllum cimmune* | Xyn | SEQ ID NO: 9 |
| *Streptomyces lividans* | Xyn B | SEQ ID NO: 10 |
| *Streptomyces lividans* | Xyn C | SEQ ID NO: 11 |
| *Streptomyces* sp. No. 36a | Xyn | SEQ ID NO: 12 |
| *Streptomyces thermoviolaceus* | Xyn II | — |
| *Thermomonospora fusca* | Xyn A | SEQ ID NO: 13 |

TABLE 1-continued

Family 11 xylanase enzymes

| Microbe | Xylanase | SEQ ID NO |
|---|---|---|
| *Thermomyces lanuginosus* | Xyn | SEQ ID NO: 20 |
| *Trichoderma harzianum* | Xyn | SEQ ID NO: 14 |
| *Trichoderma reesei* | Xyn I | SEQ ID NO: 15 |
| *Trichoderma reesei* | Xyn II | SEQ ID NO: 16 |
| *Trichoderma viride* | Xyn | SEQ ID NO: 17 |

Family 11 xylanases share extensive amino acid sequence similarity (FIG. 1). Structural studies of several Family 11 xylanases indicate that Family 11 xylanases from bacterial and fungal origins share the same general molecular structure (U.S. Pat. No. 5,405,769; Arase et al 1993). In addition, most Family 11 xylanases identified so far exhibit three types of secondary structure, including beta-sheets, turns and a single alpha helix. The helix of *Trichoderma reesei* xylanase II enzyme encompasses the region from amino acid 151 to amino acid 162 (Torronen et. al. 1995).

A xylanase is classified as a Family 11 xylanase if it comprises amino acids common to other Family 11 xylanases, including two glutamic acid (E) residues which may serve as catalytic residues. The glutamic acid residues are found at positions 86 and 177 (see FIG. 1; based on Tr2 (*Trichoderma reesei* xylanase II enzyme) amino acid numbering).

Most of the Family 11 xylanases identified thus far are mesophilic and have low-molecular masses (20 kDa). However, this family also includes at least two thermostable xylanases of higher molecular mass, *Thermomonospora fusca* xylanase A (TfX-A) of 296 amino acids and a molecular mass of approximately 32 kDa (Irwin et. al., 1994); Wilson et al. 1994, WO 95/12668) and *Clostridium stercorarium* xylanase A of 511 amino acids and a molecular mass of approximately 56 Kda. The *Clostridium stercorarium* xylanase A enzyme exhibits maximum activity at a temperature of 70° C. (Sakka et al., 1993).

The large thermostable Family 11 xylanases differ from the small mesophilic enzymes by the possession of a hydrophobic cellulose-binding domain (CBD) in the extended C-terminus of the enzyme. The TfX-A enzyme is composed of a catalytic core sequence of 189 residues common to all Family 11 xylanases, and a cellulose binding domain of 107 residues. The larger *C. stercorarium* xylanase A has two copies of the cellulose binding domain.

Site-directed mutagenesis has been used in the present invention to produce mutations in xylanases which render the enzyme more thermophilic and alkalophilic compared to the native enzyme. Preferably, the mutant xylanase is one derived from a Family 11 xylanase. More preferably, the mutant xylanase of the present invention comprises a mutant *Trichoderma reesei* xylanase II enzyme.

Therefore, it is considered within the scope of the present invention that xylanases, including Family 11 xylanases for example but not limited to *Trichoderma reesei* xylanase II, *Trichoderma reesei* xylanase I, *Trichoderma viride* xylanase, *Streptomyces lividans* xylanase B and *Streptomyces lividans* xylanase C, may be modified following the general approach and methodology as outlined herein. It is also considered within the scope of the present invention that non-Family 11 xylanases may also be modified following the general principles as described herein in order to obtain a xylanase enzyme that exhibits thermophilicity and alkalophilicity.

By the term "thermophilicity" it is meant that an enzyme is active, or more active, at a higher temperature when compared with the activity of another enzyme when all other conditions remain constant. For example, xylanase 1 exhibits increased thermophilicity compared to xylanase 2 if xylanase 1 is capable of, or is more active in, hydrolysing xylan at a higher temperature than xylanase 2, under identical conditions using the same substrate. As most xylanases are effective at a higher temperature when hydrolysing pure xylan rather than pulp, comparative analysis should be made using the same substrate. Quantitative measures of thermophilicity referred to herein use pure xylan substrates unless otherwise indicated.

By "thermostability" it is meant the ability of an enzyme to be stored or incubated at high temperature conditions, typically in the absence of substrate, and then exhibit activity when returned to standard assay conditions. For example, xylanase 1 is said to display increased thermostability compared to xylanase 2 if xylanase 1 retains a greater amount of activity than xylanase 2 after being maintained at a certain temperature (typically a higher temperature), for example but not limited to, 70° C. for 24 hours, followed by assay at a lower temperature. In contrast to thermophilicity, thermostability relates to the remaining enzyme activity following an incubation in the absence of substrate.

These use of these two terms (thermophilicity and thermostability) has been confused within the prior art as they have been used interchangeably. However, the use of the terms as defined herein is consistent with the usage of the terms in the art (Mathrani and Ahring, 1992).

By "alkalophilicity" it is meant that an enzyme is active, or more active, at a higher pH when compared with the activity of another enzyme when all other conditions remain constant. For example, xylanase 1 exhibits increased alkalophilicity compared to xylanase 2 if xylanase 1 is capable of hydrolysing xylan at a higher pH than xylanase 2. Typically alkalophilicity relates to enzyme activity in the presence of xylan substrate.

By "TrX numbering" it is meant the numbering associated with the position of amino acids based on the amino acid sequence of TrX (Xyn II—Table 1; Tr2—FIG. 1; SEQ ID NO:16). As disclosed below and as is evident upon review of FIG. 1, Family 11 xylanases exhibit a substantial degree of sequence similarity. Therefore, by aligning the amino acids to optimize the sequence similarity between xylanase enzymes and by using the amino acid numbering of TrX as the basis for numbering, the positions of amino acids within other xylanase enzymes can be determined relative to TrX.

By modified xylanase, it is meant the alteration of a xylanase molecule using techniques that are known to one of skill in the art. These techniques include, but are not limited to, site directed mutagenesis, cassette mutagenesis, random mutagenesis, synthetic oligonucleotide construction, cloning and other genetic engineering techniques.

As described in more detail herein, several mutant xylanases have been prepared that exhibit increased thermophilicity, alkalophilicity and thermostability when compared to native xylanase. A list of several of mutants, which is not to be considered limiting in any manner, is presented in Table 2.

Furthermore, the present is directed to a modified Family 11 xylanase obtained from a *Trichoderma* sp. that comprises at least one substituted amino acid residue, and characterized as having a maximum effective temperature (MET) between about 69° C. to about 78° C. Preferably, the modified xylanase is characterized as having a MET between about 70° to about 75° C. This invention also pertains to a modified xylanase obtained from *Trichoderma*, comprising at least one substituted amino acid, and characterized as having a maximum effective pH (MEP) between about 5.8 to about 7.6. Preferably the MEP is between about 6.5 to about 7.4. This invention also pertains to a modified xylanase obtained from *Trichoderma*, comprising at least one substituted amino acid, and characterized as having a maximum effective temperature (MET) between about 69° C. to about 78° C., and a maximum effective pH (MEP) is between about 5.8 to about 7.6. Preferably the MET is between about 70° to about 75° C., and the MEP is between about 6.5 to about 7.4.

Determination of the MET and MEP of a xylanase may be carried out as follows:

i) measure the temperature profile of a xylanase as outlined in Example 3. The temperatures for which at least 80% of the optimal (maximum) activity are determined, and the highest temperature is the MET;

ii) measure the pH profile of a xylanase as outlined in Example 4. The pH for which at least 80% of the optimal (maximum) activity is determined, and the highest pH is the MEP.

These values may then be plotted as shown in FIG. 20.

Substitution at position 75 or 105 does not change the specific activity of the xylanase enzyme compared to that of native xylanase (see Table 4, Example 3). Similarly, mutations at position 157, 161, 162, and 165 do not change the specific activity on the modified xylanase.

Increasing the Thermophilicity of Xylanase

Figure 3:
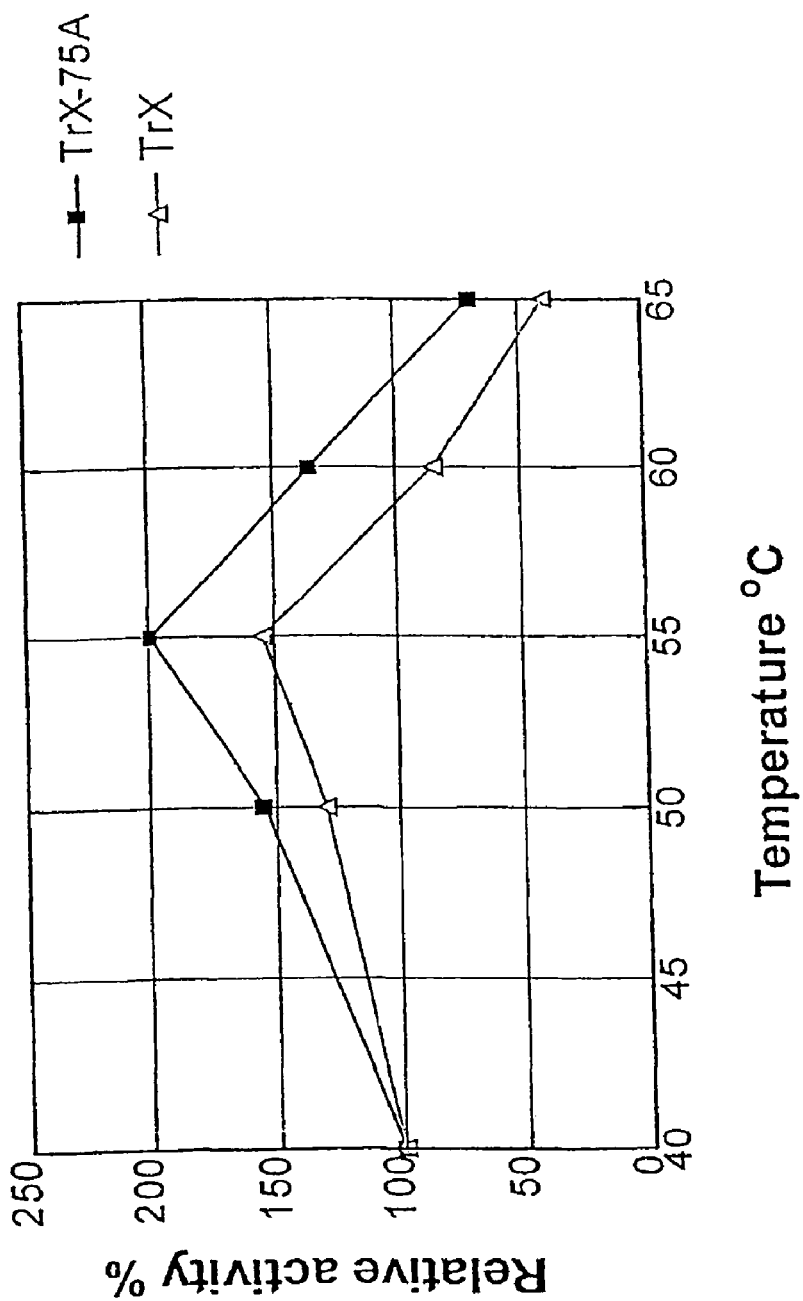
FIG. 3 shows the effect of temperature on the enzymatic activity of modified xylanase TrX-75A, compared with TrX, at pH 5.5 during 30 min incubations. The data are normalized to the activity observed at 40° C.
Figure 4:
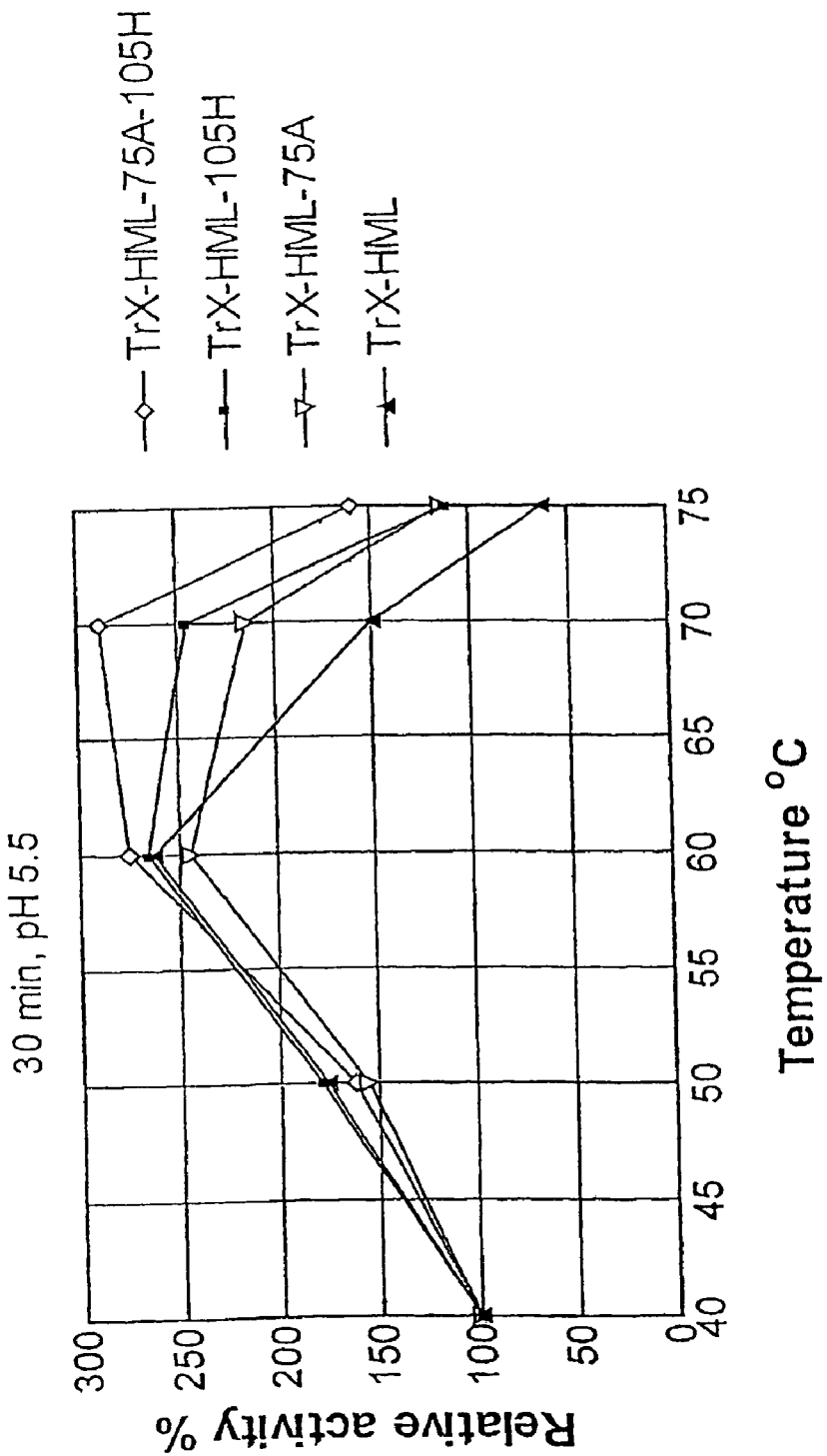
FIG. 4 shows the effect of temperature on the enzymatic activity of modified xylanases TrX-HML, TrX-HML-75A, TrX-HML-105H and TrX-HML-75A-105H, at pH 5.5 during 30 min incubations. The data are normalized to the activity observed at 40° C.

The mutant TrX-75A, bearing a single S75A mutation, showed greater enzymatic activity than the native TrX xylanase at 50, 55, 60 and 65° C. (FIG. 3). Further, the S75A mutation in the TrX-HML-75A mutant xylanase exhibited greater enzymatic activity than the TrX-HML parent xylanase at 70° C. and 75° C. (FIG. 4). These results suggest that the S75A mutation improves the thermophilicity of TrX and TrX-HML xylanases.

The Ser to Ala mutation at position 75 (S75A) improves the thermophilicity for both TrX-75A and TrX-HML-75A xylanases in comparison to their native counterparts. The S75A mutation represents a change from a Ser amino acid bearing a side-chain which is relatively polar and hydrophilic to an Ala residue which bears a small and relatively nonpolar side-chain. Without wishing to be bound by theory, it is possible that replacing the polar serine amino acid with the smaller nonpolar Ala residue enhances intramolecular packing of the xylanase. The enhanced intramolecular packing of the ter-

TABLE 2

Modified xylanases

| Xylanase | Description | SEQ ID NO |
| --- | --- | --- |
| TrX-75A | TrX with Ser at position 75 replaced with Ala (S75A) | SEQ ID: 59 |
| TrX-105H | TrX with Leu at position 105 replaced with His (L105H) | SEQ ID: 60 |
| TrX-HML | TrX with N10H, Y27M, and N29L (see U.S. 5,759,840) | SEQ ID: 61 |
| TrX-HML-105H | TrX N10H, Y27M, N29L and L105H | — |
| TrX-HML-105K | TrX N10H, Y27M, N29L and L105K | — |
| TrX-HML-105R | TrX N10H, Y27M, N29L and L105R | — |
| TrX-HML-75A | TrX N10H, Y27M, N29L and S75A | SEQ ID: 62 |
| TrX-HML-75A-105H | TrX N10H, Y27M, N29L, S75A, and L105H | SEQ ID: 63 |
| TrX-HML-75A-105R | TrX N10H, Y27M, N29L, S75A and L105R | SEQ ID: 64 |
| TrX-HML-75C-105R | TrX N10H, Y27M, N29L, S75C and L105R | SEQ ID: 65 |
| TrX-HML-75G-105R | TrX N10H, Y27M, N29L, S75G and L105R | SEQ ID: 66 |
| TrX-HML-75T-105R | TrX N10H, Y27M, N29L, S75T and L105R | SEQ ID: 67 |
| TrX-HML-125A | TrX N10H, Y27M, N29L and Q125A | — |
| TrX-HML-125A129E | TrX N10H, Y27M, N29L, Q125A and I129E | — |
| TrX-HML-GRAE | TrX N10H, Y27M, N29L, S75G, L105R, Q125A and I129E | SEQ ID: 68 |
| TrX-HML-AHAE | TrX N10H, Y27M, N29L, S75A, L105H, Q125A and I129E | SEQ ID: 69 |
| TrX-HML-GHAE | TrX N10H, Y27M, N29L, S75G, L105H, Q125A and I129E | SEQ ID: 70 |
| TrX-HML-ARAE | TrX N10H, Y27M, N29L, S75A, L105R, Q125A and I129E | SEQ ID: 71 |
| TrX-HML-GPRAE | TrX N10H, Y27M, N29L, S75G, K104P, L105R, Q125A and I129E | SEQ ID: 72 |
| TrX-HML-GPHAE | TrX N10H, Y27M, N29L, S75G, K104P, L105H, Q125A and I129E | SEQ ID: 73 |
| TrX-HML-AHAE-RR | TrX N10R, Y27M, N29L, S75A, L105H, Q125A, I129E, A132R, and Y135R | SEQ ID: 74 |
| TrX-HML-AHAE-RRR | TrX N10H, Y27M, N29L, S75A, L105H, Q125A, I129E, A132R, Y135R, and H144R | SEQ ID: 75 |
| TrX-157D-161R-162H-165H | TrX N157D, Q161R, Q162H, and T165H | — |
| TrX-HML-AHAE-RRR-DRHH | TrX N10H, Y27M, N29L, S75A, L105H, Q125A, I129E, A132R, Y135R, H144R, N157D, Q161R, Q162H, and T165H | SEQ ID: 76 |
| TrX-HML-AHA-RR-DRHH | TrX N10H, Y27M, N29L, S75A, L105H, Q125A, Y135R, H144R, N157D, Q161R, Q162H, and T165H | SEQ ID: 77 |
| TrX-HML-AHAE-RR-DRHH | TrX N10H, Y27M, N29L, S75A, L105H, Q125A, I129E, Y135R, H144R, N157D, Q161R, Q162H, and T165H | SEQ ID: 78 | tiary structure of xylanase may in turn improve van der Waals interactions between closely positioned a polar substituents. The result of such improved intramolecular packing is an increase in the thermophilicity of the enzyme. In. such cases, higher temperatures are required to denature and inactivate the mutant xylanase.

Substitution of position 157 with an acidic amino acid, and positions, 161, 162, and 165 with a basic amino acid, for example, but not limited to, replacing Asn at 157 with Asp (N157D), Ala at position 161 with Arg (A161R), Gln at position 162 with His (Q162H), and Thr at position 165 with His (T165H) to produce TrX-157D-161R-162H-165H may result in a slight increase in the thermophilicity of this enzyme over that of the parent TrX enzyme (FIG. 15).

Similarly, mutation of Leu 105 to His (L105H) in TrX-HML xylanase to produce the TrX-HML-105H mutant xylanase exhibits increased enzymatic activity over the parent TrX-HML xylanase at 70 and 75° C. (FIG. 4).

The Leu to His mutation at position 105 (L105H) improves the thermophilicity of TrX-HML-105H in comparison to TrX-HML xylanase. The L105H mutation represents a change from Leu, which is a hydrophobic, branched-chain amino acid to His bearing a relatively bulky, polar imidazole side-chain. Without wishing to be bound by theory, the L105H mutation introduces a reasonably bulky, planar amino acid capable of hydrogen bonding with other amino acids in the same vicinity of the molecule, possibly enhancing the intramolecular packing of atoms in the enzyme and thereby stabilizing the tertiary structure of the enzyme. Further, the imidazole side-chain may be protonated in the assay conditions to give the conjugate acid of imidazole. The protonated imidazole moiety may partake in attractive electrostatic interactions within the three dimensional tertiary structure of the xylanase and thereby stabilize its tertiary structure.

The combined mutant xylanase, TrX-HML-75A-105H, exhibited a maximum enzymatic activity at a temperature of 70° C. and further showed greater enzymatic activity than either TrX-HML-75A or TrX-HML-105H single mutant xylanases at 70° C. (FIG. 4). These results indicate that the effects of the S75A and L105H mutations, on the thermophilicity of the mutant xylanase, are additive or complementary.

Figure 5:
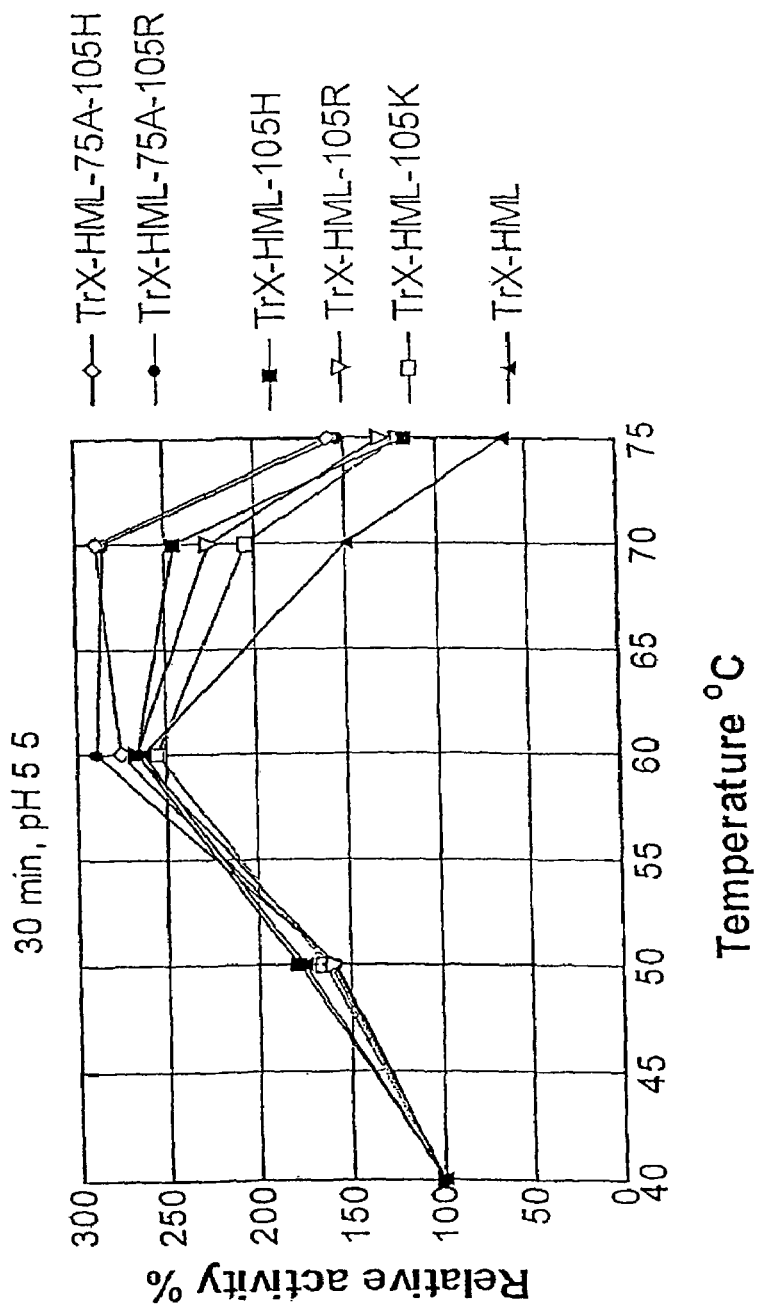
FIG. 5 shows the effect of temperature on the enzymatic activity of modified xylanases TrX-HML, TrX-HML-105K, TrX-HML-105R, TrX-HML-105H, TrX-HML-75A-105R and TrX-HML-75A-105H at pH 5.5 during 30 min incubations. The data are normalized to the activity observed at 40° C.

A series of TrX-HML xylanases bearing mutations at position-105 were constructed to determine those amino acid residues which enhance the thermophilicity of the parent TrX-HML enzyme (FIG. 5). Three mutants at position 105, TrX-HML-105H, TrX-HML-105R and TrX-HML-105K, showed greater enzymatic activity than the precursor TrX-HML enzyme from about 60° C. or higher. The native xylanase comprises a Leu at position 105, a relatively hydrophobic branched-chain amino acid. Mutant xylanases wherein position 105 is substituted with a hydrophilic, positively charged or basic amino acid, for example His, Arg or Lys exhibited enhanced thermophilicity.

The combination mutant TrX-HML-75A-105R xylanase showed a similar temperature-activity profile to TrX-HML-75A-105H xylanase, suggesting that the S75A and L105R mutations, like those of the S75A and L105H mutations are additive or complementary. These results further suggest that basic residues at position 105 enhance the thermophilicity of the xylanases.

Figure 6:
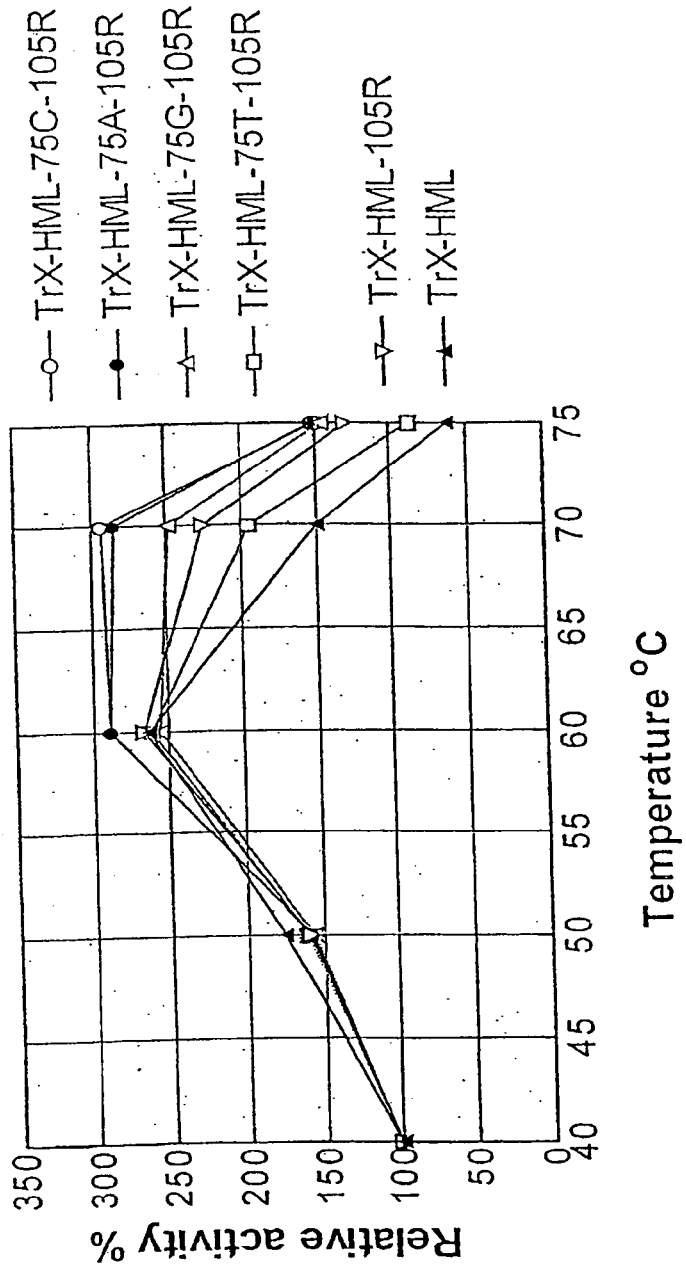
FIG. 6 shows the effect of temperature on the enzymatic activity of modified xylanases TrX-HML, TrX-HML-105R, TrX-HML-75T-105R, TrX-HML-75G-105R, TrX-HML-75A-105R and TrX-HML 75C-105R at pH 5.5 during 30 min incubations. The data are normalized to the activity observed at 40° C.

Due to the observed increase in thermophilicity associated with mutations involving position 75, combination mutants were also examined involving different substitutions at position 75, along with L105R. Three genetically modified xylanase mutants, TrX-HML-75C-105R, TrX-HML-75A-105R and TrX-HML-75G-105R showed greater enzymatic activity than either the precursor TrX-HML-105R xylanase or the TrX-HML xylanase at temperatures greater than about 60° C. (FIG. 6). A fourth mutant TrX-HML-75T-105R xylanase showed no enhancement in thermophilicity over the precursor TrX-HML-105R xylanase that has a natural Ser residue at position 75. The mutant threonine residue at position 75, like the natural Ser 75 residue found in TrX and TrX-HML parent xylanases, is a hydrophilic amino acid. Collectively, the mutations which involve replacing Ser at position 75 with small, nonpolar amino acids, such as but not wishing to be limiting Ala or Gly lead to an increase in the thermophilicity of the xylanase.

A series of mutant xylanases were also constructed with mutations Gln-125 to Ala and Ile-129 to Glu. The new mutants showed an increase of enzymatic activity at higher temperatures, as compared to their precursor xylanases (see FIGS. 7 to 9). These include (see Table 2 for complete description of modified enzymes):

TrX-HML-125A;
TrX-HML-125A129E;
TrX-HML-GRAE;
TrX-HML-AHAE;
TrX-HML-GHAE;
TrX-HML-ARAE;
TrX-HML-GPHAE; and
TrX-HML-GPRAE.

In some organisms, the expression and recovery of these modified xylanases may be reduced or not possible due to the synthesis of sites within the protein that reduce expression or recovery of the modified xylanase. This reduced recovery may vary depending upon the host within which the modified enzyme is expressed. For example, which is not to be construed as limiting, alterations of the amino acid sequence may produce a proteolytic cleavage site that is recognized by a protease in certain, but not all hosts. In order to overcome this problem adjacent amino acids, on one or both sides of the site comprising the desired mutation, may be modified in order to attend to any host-specific difficulty for the expression and recovery of a modified xylanase. Preferably, the additional amino acids that are altered do not negate the effect of the initially substituted amino acid in increasing the thermophilicity, or alkalophilicity, or both the thermophilicity and alkalophilicity, of the enzyme. For example, which is not to be considered limiting in any manner, a modified xylanase comprising a substitution of L105R, can be produced from *E. coli*, however, the recovery of this enzyme is reduced in *Trichoderma*, and *Aspergillus* due to endogenous KEX protease activity recognizing the amino acid combination "Lys-Arg" at positions 104 and 105 respectively. In this case, the amino acid at position 104 may be substituted for by an alternate amino acid, for example a non-polar amino acid as in modified xylanases TrX-HML-GPHAE, or TrX-HML-GPRAE. As shown in FIG. 14, the substitution of Lys at position 104 by Pro does not affect the thermophilicity or alkalophilicity of these modified xylanase. It is to be understood that other proteases may recognize other amino acid combinations that may be produced when preparing the modified xylanases as described herein. Therefore, the present invention also pertains to a modified xylanase comprising one or more substituted amino acids adjacent to the amino acids as described herein.

This invention therefore includes a modified xylanase comprising a His at position 10, a Met at position 27, a Leu at position 29, and at least one of:

a non-polar amino acid at positions 75, 104, or 125, or a combination thereof;
a polar amino acid at position 105; and
an acidic amino acid at position 129.

Preferably, the amino acid at position 75 is Ala, the amino acid at position 125 is selected from the group consisting of Ala, Cys, Gly, and Thr, the amino acid at position 125 is Glu, the amino acid at position 105 is selected from the group consisting of His, Lys, and Arg, and the amino acid residue at position 104 is Pro.

Increasing the Alkalophilicity of Xylanase

The effect of pH conditions on the enzymatic activity of single mutant TrX-75A xylanase is shown in FIG. 10. At 55° C., the TrX-75A mutant xylanase displays an increase in activity above pH 5.5 when compared to the native TrX enzyme over the same pH range. A similar contribution to improved alkalophilicity by the substitution of Ser for Ala at position 75 (TrX-75A) was also observed for the TrX-HML-75A over the parent TrX-HML xylanase at pH conditions between 6.5 and 7 (FIG. 11).

An increase in alkalophilicity, with an increase in activity over pH from about 5.2 to a pH of about 6.5 is also observed in TrX-157D-161R-162H-165H, when compared with that of the native TrX over the same pH range (FIG. 16).

The L105H mutation in the TrX-HML-105H mutant xylanase also increased the enzymatic activity over the parent TrX-HML xylanase at pH 6.5 and 7.0 (FIG. 11). Interestingly, the combination mutant TrX-HML-75A-105H xylanase showed greater enzymatic activity than either TrX-HML-75A or TrX-HML-105H single mutant xylanases at pH 6.5 and 7.0 (FIG. 11), suggesting that the effects of the S75A mutation and the L105H mutation on the alkalophilicity of the xylanase are additive or complementary.

A series of genetically modified xylanases modified at position 105 were constructed to determine those residues which promote increased alkalophilicity in modified xylanases (FIG. 12). Three mutant xylanases bearing three mutations at position 75, TrX-105H, TrX-HML-105R and TrX-HML-105K showed greater enzymatic activity than the precursor TrX-HML xylanase at pH conditions of 6.5 and 7.0. Collectively, the mutations which lead to increases in alkalophilicity, represent a change from a branched chain relatively hydrophobic Leu residue to a residue which is hydrophilic, positively charged or basic.

Without wishing to be bound by theory, the hydrophilic, positively charged, or basic residues may facilitate intramolecular packing with other atoms that are juxtapositioned in the same vicinity in the tertiary structure of the xylanase. These residues may stabilize the three dimensional structure of the enzyme against structural perturbations in the molecule which may arise via the titration of several ionizable side-chains of amino aids in other regions of the molecule. Again, without wishing to be bound by theory, the basic ionized form of the side chain may be important in altering the pH activity profile of the enzyme, as at pH conditions between 6 and 7, Arg and Lys residues have side-chains which likely remain protonated. In contrast, His residues having a pKa of approximately 6 in solution for its imidazole moiety could be present in either a protonated or unprotonated form. However, it is known to those skilled in the art that the polarity of the substituents surrounding an amino acid side chain may affect its pKa value. For example, the side chain of a His residue in a polar or hydrophobic region of a protein may exhibit a pKa of 6 whereas the same side-chain in a hydrophobic or apolar environment may exhibit a pKa of 7 or greater.

In another study, mutations were constructed at position 75 of TrX-HML to determine which residues promote increased alkalophilicity in modified xylanases (FIG. 13). Four xylanases bearing mutations at position 75, TrX-HML-75C-105R, TrX-HML-75A-105R, TrX-HML-75G-105R and TrX-HML-75T-105R showed greater enzymatic activity at pH conditions of 6.0, 6.5 and 7.0, compared to the precursors TrX-HML and TrX-HML-105R xylanases.

The mutations Q125A and 129E that enhanced the thermophilicity of xylanases, are compatible to the mutations at positions 75 and 105 described above, as the combination mutants like TrX-HML-75G-105H-125A129E possessing these two mutations generally maintained the pH/activity profile of the precursor xylanase TrX-HML-75G-105H (FIG. 14).

A series of mutant xylanases were also constructed with mutations Gln-125 to Ala, and Ile-129 to Glu. The new mutants showed an increase of enzymatic activity at higher pH, as compared to their precursor xylanases (see FIGS. 11 to 14 and 17-19). These include (see Table 2 for complete description of modified enzymes):

TrX-HML-125A;
TrX-HML-125A129E;
TrX-HML-GRAE;
TrX-HML-AHAE;
TrX-HML-GHAE;
TrX-HML-ARAE;
TrX-HML-GPHAE;
TrX-HML-GPRAE;
TrX-HML-AHAE-RR;
TrX-HML-AHAE-RRR;
TrX-HML-AHAE-RRR-DRHH;
TrX-HML-AHA-RR-DRHH; and
TrX-HML-AHAE-RR-DRHH Mutant xylanases comprising a basic amino acid at positions 132 and 135, in addition to the substitutions describe above, including HML-75A-105H-125A-129E, exhibited an increase in alkalophilicity. Similarly, a mutant comprising a basic amino acid at positions 132, 135 and 144, also exhibited an increase in alkalophilicity. Examples of modified xylanase comprising these mutations include TrX-HML-AHAE-RR, and TrX-HML-AHAE-RRR (FIG. 17).

Further modifications were made to xylanases in order to increase the alkalophilicity of the enzyme. For example, the substitution of an acidic amino acid at position 157, basic amino acid at positions 161, 162 and 165 with or without basic amino acid substitutions at positions. 132, 135 and 144 also increased alkalophilicity. For example, TrX-HML-AHAE-RR-DRHH, or TrX--HML-AHAE-RRR-DRHH each exhibited an increase in alkalophilicity (FIGS. 18, 19) and a MEP of about 7.0 (FIG. 20), when compared with TrX-HML-AHAE, which comprises a MEP of about 6.5, or TrX, with a MEP of about 5.6.

A further increase in alkalophilicity over those outlined above was also obtained by substitution of an acidic amino acid at position 157, and substituting a basic amino acid at positions 135, 144, 161, 162, 165, and leaving the ammo acid at positions 129 and 132 in their native state, for example, TrX-HML-AHA-RR-DRHH (FIGS. 18 and 19). This enzyme exhibits a MEP of about 7.4.

The breadth of the pH optimum for TrX-HML-AHAE is much broader when compared to the pH profile of TrX (e.g. see FIG. 19). Several of the modified xylanases of the present invention exhibit a breadth in the pH optimum approaching that of the breadth of native TrX, however, the pH optimum of these modified xylanases is shifted, with an increase of about at least 1 pH unit (FIG. 19) when compared to that of TrX. TrX exhibits 80% of its optimal activity from about pH 4.8 to about pH 5.6 (pH optimum at 80% activity over 0.8 pH units). TrX-HML-AHAE exhibits a much broader pH range where 80% of its optimal activity ranges from about pH 4.8 to about pH 6.5 (about 1.7 pH units). The range of 80% of optimal activity for TrX-HML-AHAE-RR and TrX-HML-AHAE-RRR, is from about 5.4 to about 6.6 (about 1.2 pH units; FIG. 17), for TrX-HML-AHAE-RRR-DRHH and TrX-HML-AHAE-RR-DRHH is from about pH 5.8 to about 7.0 (about 1.2 pH units), and for TrX-HML-AHA-RR-DRHH is from about 5.9 to about 7.4 (about 1.5 pH units; see FIGS. 18 and 19).

Therefore, this invention also pertains to a modified xylanase comprising a His at position 10, a Met at position 27, a Leu at position 29, and at least one of:

a non-polar amino acid at position 75, 104, or 125 or a combination thereof;

a polar amino acid at position 105;

an acidic amino acid at positions 129 and 157; and a basic amino acid at positions 132, 135, 144, 161, 162, or 165, or a combination thereof.

Preferably, the amino acid at position 75 is Ala, the amino acid at position 125 is selected from the group consisting of Ala, Cys, Gly, and Thr, the amino acid at position 125 is Glu. The amino acid at position 105 is selected from the group consisting of His, Lys, and Arg, the amino acid residue at position 104 is Pro, the amino acid at position 132, 135, 144 and 161 is Arg, the amino acid at position 157 is Asp, and the amino acid at position 162 and 165 is His.

In summary, improved alkalophilic mutant TrX xylanases may be constructed through:

i) mutation of Ser 75 to a small non-polar residue, for example, but not limited to Ala. Furthermore, position 75 may be substituted by polar residues, for example, but not limited to Gly, Cys and Thr;

ii) mutation of Leu 105 to a basic residue such as but not limited to Arg, Lys or His;

iii) mutation of Gln 125 to Ala;

iv) mutation of Ile 129 to Glu;

v) mutation of Ala 132, Tyr 135, His 144, Gln 161, Gln 162, Thr 165 or a combination thereof to a basic amino acid, for example, Arg, Lys or His;

vi) mutation of Asn157 to an acidic amino acid, for example, Asp or Glu;

vii) combination of mutations described in i) with those described in ii) to iii) for the improvement of thermophilicity and alkalophilicity; or viii) combination of mutations described in i) to vi), above, with the HML series of mutations as described above (see also U.S. Pat. No. 5,759,840).

The above description is not intended to limit the claimed invention in any manner, furthermore, the discussed combination of features might not be absolutely necessary for the inventive solution.

EXAMPLES

The present invention will be further illustrated in the following examples. However it is to be understood that these examples are for illustrative purposes only, and should not be used to limit the scope of the present invention in any manner.

Example 1

Construction of *Trichoderma reesei* Mutant Xylanases

Basic recombinant DNA methods like plasmid preparation, restriction enzyme digestion, polymerase chain reaction, oligonucleotide phosphorylation, ligation, transformation and DNA hybridization were performed according to well-established protocols familiar to those skilled in the art (e.g. Sung et al., 1986) or as recommended by the manufacturer of the enzymes or kit. The buffers for many enzymes have been supplied as part of a kit or made according to the manufacturer's instructions. Restriction enzymes, T4 polynucleotide kinase and T4 DNA ligase were purchased from New England BioLabs Ltd, Mississauga, Ont. GeneAmp PCR reagent kit was purchased from Perkin-Elmer. A precursor plasmid pXYbc, which is a pUC type plasmid with a *Bacillus circulans* xylanase gene inserted, has previously been prepared and published (Sung et al, 1993; Campbell et al., U.S. Pat. No. 5,405,769). A commonly used *E. coli* strain, HB101 (Clonetech Lab, Palo Alto, Calif.) was used as a transformation and expression host for all gene constructs. Birchwood xylan and Remazol Brilliant Blue R-D-Xylan were purchased from Sigma (St. Louis, Mo.). Hydroxybenzoic acid hydrazide (HBAH) was purchased from Aldrich. Oligonucleotides were prepared with an APPLIED BIOSYSTEM DNA synthesizer (model 380B). All xylanase enzymatic assays were performed in a covered circulating water bath (Haake type F 4391) and maintained within a temperature range of ±0.1° C.

1-1: Construction of Precursor Plasmid pTrX Harbouring Synthetic TrX (SEQ ID NO:39)

The precursor plasmid pTrX for mutations disclosed below has been previously published (Sung et al, 1995). This plasmid is derived from a pUC119 plasmid with a synthetic nucleotide sequence encoding a *Trichoderma reesei* xylanase (TrX; FIG. 2). Expression of this xylanase and other mutant xylanases subsequently described are under the control of the lac Z promoter of the pUC plasmid. The total assembly of the *Trichoderma* xylanase gene required two stages, initially for the (92-190; Tr2 numbering) region, then followed by the (1-92; Tr2 numbering) region. The protocol for the construction of this gene is routine and identical to the standard published procedure for many other genes. The protocol requires enzymatic phosphorylation of overlapping synthetic oligonucleotides which encodes a xylanase. This is followed by their ligation into an appropriately cut plasmid.

For the construction of TrX (92-190), ten overlapping oligonucleotides (see FIG. 2):

| | |
|---|---|
| XyTv-101, | SEQ ID NO:29; |
| XyTv-102, | SEQ ID NO:30; |
| TrX-103, | SEQ ID NO:31; |
| XyTv-104, | SEQ ID NO:32; |
| XyTv-105, | SEQ ID NO:33; |
| XyTv-106, | SEQ ID NO:38; |
| XyTv-107, | SEQ ID NO:37; |
| TrX-108, | SEQ ID NO:36; |
| XyTv-109, | SEQ ID NO:35; and |
| XyTv-110, | SEQ ID NO:34 | were designed with codon usage frequency imitating that of *E. coli*. The SalI and BglII cohesive ends of two terminal oligonucleotides enabled the enzymatic ligation of the ten fragments into the linearized plasmid pXYbc. The ten oligonucleotides (50 pmol, 1 μL for each) encoding the TrX(92-190) region of *Trichoderma* xylanase were phosphorylated in a mixture containing 10× standard kinase buffer (0.4 μL), 1 mM ATP (4 μL), T4 DNA kinase (5 units), and water (3 μL). Phosphorylation reactions were carried out for 1 h at 37° C. The solutions were then combined and heated to 70° C. for 10 min. After being cooled slowly to room temperature, the combined solutions were added to a mixture of 4 mM ATP (3.5 μL), EcoR1-HindIII linearized plasmid pUC119 (0.1 pmol), and T4 DNA ligase (3.5 μL) and incubated at 12° C. for 20 h. Aliquots of the ligation mixture were used to transform *E. coli* HB101 on YT plates (8 g yeast extract, 5 g bacto-tryptone, 5 g NaCl, 15 g of agar in 1 L of water) containing ampicillin (100 mg/L).

For the preparation of a hybridization probe, one of the oligonucleotides, for example XyTv-110 (10 pmol, 1 μL) was phosphorylated with $^{32}$P-ATP (10 pmol, 3 μL) using T4 DNA kinase (1 μL), 10× kinase buffer (1 μL), and water (4 μL) at 37° C. for 1 h.

Transformants were selected randomly for hybridization analysis. Colonies were grown on YT plates with ampicillin overnight, and transferred onto nylon filters. They were then denatured with 0.5N NaOH-1.5M NaCl (10 min) and neutralized with 0.5N Tris-HCl (pH 7.0)-1.5M NaCl (10 min). After ultraviolet irradiation at 254 nm for 8 min, the filters were washed with 6×SSC-0.05% Triton X-100 for 30 min. Cell debris was scraped off completely. After another 30 min. in fresh solution, duplicate filters were transferred individually into separate mixtures of 6×SSC-1% dextran sulphate-0.05% TritonX-100-1× Denhardt's hybridization fluid. The $^{32}$P-labelled probe was added to the filter. After 16 h at 45° C., the filter was washed twice with 633 SSC-0.05% TritonX-100 at room temperature for 5 min. and then at 65° C. for 30 min. Positively hybridized clones with the intermediate plasmid pBcX-TrX were identified by auto-radiographic analysis.

The above protocol, involving enzymatic phosphorylation of synthetic overlapping oligonucleotides and ligation into a linearized plasmid, was employed in the assembly of the TrX(1-92) region and in the cassette mutagenesis for the subsequent generation of other mutant xylanases described in this invention.

encoding the TrX(1-91) sequence were ligated into the linearized plasmid pBcX-TrX (FIG. 2), via the protocol described above. The new plasmid pTrX therefore harbored a synthetic TrX gene (SEQ ID NO:39).

All mutant xylanase genes described below have been constructed via the method of cassette mutagenesis. The protocol for cassette mutagenesis was identical to that described for gene assembly described above. Generally, cassette mutagenesis involved (i) enzymatic phosphorylation of overlapping synthetic oligonucleotides, (ii) ligation of synthetic oligonucleotides with a linearized plasmid, (iii) transformation of the plasmid into *E. coli* HB101 competent cells, (iv) identification of mutant transformants via hybridization with the labelled oligonucleotide, and (v) confirmation of the mutation through dideoxy nucleotide sequencing.

1-2: Construction of the Precursor Plasmid pTrX-HML

The construction of this precursor plasmid pTrX-HML has been described in detail in U.S. Pat. No. 5,759,840 (see Example 1N, herein incorporated by reference; plasmid termed pN1-TX13). TrX-HML comprises the native TrX xylanase, along with three mutations at N10H (Asn at position 10 is replaced with His), Y27M and N29L. The first thirty amino acids of the sequence comprising N10H, Y27M and N29L are shown below.

```
TrX                                   1   2   3   4   5   6   7   8
amino acid                            Q   T   I   Q   P   G   T   G
           5'-CT AGC TAA GGA GG CTG CAG ATG CAA ACA ATA CAA CCA GGA ACC GGT
              3'-G ATT CCT CC GAC GTC TAC GTT TGT TAT GTT GGT CCT TGG CCA
                    NheI                                              PinAI 9  10  11  12  13  14  15  16  17  18  19  20  21  22  23  24
           Y   H   N   G   Y   F   Y   S   Y   W   N   D   G   H   G   G
           TAC CAC AAC GGT TAC TTT TAC AGC TAT TGG AAC GAT GGC CAT GGA GGC
           ATG GTG TTG CCA ATG AAA ATG TCG ATA ACC TTG CTA CCG GTA CCT CCG 25  26  27  28  29  30
           V   T   M   T   L   G   (SEQ ID NO:58)
           GTC ACA ATG ACT CTG GGG (SEQ ID NO:52)
           CAG TGT TAC TGA GAC CCC (SEQ ID NO:53)
```

For the assembly of the TrX(1-92; Tr2 numbering) region to complete the full-length *Trichoderma reesei* xylanase II gene (TrX), the intermediate plasmid pBcX-TrX was linearized by NheI and KpnI endonucleases to release the DNA insert for BcX(1-83). With NheI and KpnI cohesive ends, eight overlapping oligonucleotides:

| TrX-1,   | SEQ ID NO:21;       |
| XyTv-2,  | SEQ ID NO:22;       |
| TrX-3,   | SEQ ID NO:23;       |
| XyTv-4,  | SEQ ID NO:24;       |
| XyTv-5,  | SEQ ID NO:28;       |
| TrX-6,   | SEQ ID NO:27;       |
| XyTv-7,  | SEQ ID NO:26; and   |
| TrX-8    | SEQ ID NO:25        |

1-3: Construction of the Deletion Plasmid pTrX(1-113)

Plasmid pTrX(1-113) comprises nucleotides 1-113 of SEQ ID NO:39 (nucleotides 1-113 of TrX) and cannot express an active xylanase. Such transformants are confirmed by the absence of a clearing zone or halo around the transformant colonies on blue xylan plates.

The new plasmid pTrX(1-113) was constructed via (i) the removal of the TrX(114-190) coding sequence of pTrX through cutting with restriction enzymes BamHI and BgIII, (ii) ligation of the identical cohesive ends of the linearized plasmid, (iii) transformation into the *E. coli* HB101 competent cells followed by platting on YT plate (containing 5 g yeast extract, 3 g bacto-tryptone, 5 g NaCl, 15 g of agar in 1 L of water, 1 g Remazol Brilliant Blue R-D-xylan) and ampicillin (100 mg/L), (iv) identification of the mutant transformants through the loss of xylanase activity (absence of a clearing zone or halo around the colonies on the blue xylan plate overnight at 40° C.), and (v) confirmation of the mutation through dideoxy nucleotide sequencing. The protocol for each of these steps was similar to that for gene assembly described above.

1-4: Construction of the Deletion Plasmid pTrX-HML(1-113)

Plasmid pTrX-HML(1-113) is similar to pTrX(1-113), but contains three mutations at positions 10, 27 and 29 (Tr2 numbering) of N10H, Y27M and N29L (as described above). The plasmid was constructed with the same protocol as described for pTrX(1-113; see above), in that the sequence encoding the TrX(114-190) region was deleted. The pTrX-HML(1-113) plasmid does not express an active xylanase.

1-5: Construction of pTrX-75A and pTrX-105H

All of the following mutant xylanase genes, based on the pTrX-derived plasmids pTrX(1-113) (see Example 1-3) and pTrX-HML(1-113) (see Example 1-4), were constructed using cassette mutagenesis. PCR primers that harbor specific mutations, were used to create PCR products. These PCR products were used to complete the C-terminal sequence (residues 114-190; Tr2 numbering) of the full length xylanase genes. Appearance of clearing zones or halos around transformant colonies plated on plates containing blue xylan indicated that these colonies expressed an active xylanase and thus provides a marker for clones expressing a functional mutant TrX enzyme.

The protocol for the construction of these plasmids is similar to the protocol previously described for gene assembly (above). The procedure involved:
i) PCR with primer oligonucleotides bearing specific mutations at position-75 (in the case of pTrX-75A), or position-105 (in the case of pTrX-105H),
ii) cutting the PCR product with restriction enzymes HindIII at one end and KasI or EcoRI at the other,
iii) ligation of the restriction fragments to the HindIII/KasI- or EcoRI-linearized deletion plasmid,
iv) transformation into *E. coli* HB101 competent cells,
v) identification of mutant transformants expressing xylanase activity (indicated by the appearance of a clearing zone or halo surrounding colonies plated on media containing blue xylan), and
vi) confirmation of the mutation through dideoxy nucleotide sequencing.

The two xylanase mutants TrX-75A and TrX-105H comprise the sequence of TrX, with the exception of that the Ser at position 75 was replaced with an Ala residue (S75A) in TrX-75A, and the Leu at position 105 was replaced with a His residue (L105H) in TrX-105H.

The PCR primers used to create these genetically modified xylanases (specific mutation os shown in bold) include:
PCR oligonucleotide primers:

TX-75A-1
(SEQ ID NO:40)
```
   69  70  71  72  73  74  75  76  77  78  79  80
    N   G   N   S   Y   L   A   V   Y   G   W   S
5'-T GGG AAT TCA TAC TTA GCC GTC TAT GGC TGG TCT
       EcoRI
    81
     R
    AG
```

TX-105H-1
(SEQ ID NO:41)
```
     100 101 102 103 104 105 106 107 108 109 110 111
      T   G   A   T   K   H   G   E   V   T   S   D
5'-ACC GGC GCC ACA AAA CAC GGC GAA GTC ACT AGT GAT
        KasI
    112 113
     G   S
    GGA TCC
```

Reverse PCR primer TX-C1 comprised:

TX-C1
(SEQ ID NO:42)
```
    183 184 185 186 187 188 189 190 ter
     G   S   A   S   I   T   V   S
    CCA AGG CGA TCA TAA TGT CAC TCG ATT TCT AGA
                                          BglI
    ACT TCG AAC CC-5'
       HindIII
```

The appropriate PCR template, oligonucleotide primers, and restriction enzymes to cut the end of the PCR products are listed below in Table 3-1.

TABLE 3-1

| PCR product | PCR upstream primer | PCR reverse primer | PCR template | Restriction enzymes for PCR product |
|---|---|---|---|---|
| (a) | TX-75A-1 | TX-C1 | pTrX | EcoRI/HindIII |
| (b) | TX-105H-1 | TX-C1 | pTrX | KasI/HindIII |

For the preparation of PCR product (a), plasmid pTrX was used as a template for PCR. The reaction solution contained plasmid pTrX DNA (50 ng, 15 μL), 5 μL 10× buffer (100 mM KCl, 100 mM ammonium sulfate, 200 mM Tris-HCl pH 8.8, 40 mM magnesium sulfate, 1% TritonX-100, 100 mg/ml BSA), 5 μL 5 mM dNTPs, PCR primer TX-75A (25 pmol, 2.5 μL), and reverse PCR primer TX-C1 (25 pmol, 2.5 μL) and water (19 μL).

The reaction was covered with paraffin oil (50 μL) to prevent evaporation. The reaction mixture was pre-warmed to 94° C. without enzyme for 5 min, then the reaction mixture was cooled to 72° C. Subsequently, DNA polymerase (1 μL, 1 U) was added to the reaction mixture. The reaction mixture was incubated in a temperature cycler for 30 cycles of 94° C. for 1 min., 55° C. for 2 min. and then 72° C. for 2 min. The yield of the PCR product was approximately 1 μg of a 400 bp fragment. This fragment was purified from an agarose gel.

The EcoRI/HindIII-linearized PCR product (a) (Table 3-1) was ligated to the EcoRI/HindIII-linearized pTrX plasmid to generate plasmid pTrX-75A comprising full length xylanase with Ser at position 75 replaced with Ala (S75A).

In the same manner, PCR product (b) (Table 3-1) was prepared and was linearized with the KasI and HindIII restriction nucleases. The linearized product (b) was ligated to the KasI/HindIII-linearized pTrX plasmid to generate plasmid pTrX-105H comprising full length xylanase with Leu at position, 105 replaced with His (L105H).

1-6: Construction of pTrX-HML-105H, pTrX-HML-105K and pTrX-HML-105R

Three mutant xylanases TrX-HML-105H, pTrX-HML-105K and pTrX-HML-105R are similar to TrX-HML except that Leu at position 105 is replaced by His (L105H), Lys (L105K) and Arg (L105R), respectively. As indicated previously, the TrX-HML xylanase is similar to the TrX xylanase except that Asn at position 10 is replaced with His (N10H), Tyr at position 27 is replaced by Met (Y27M) and Asn at position 29 is replaced by Leu (N29L).

A similar PCR product (b) for the synthesis of pTrX-105H was used for the construction of pTrX-HML-105H. The PCR primers with mutation (in bold type) in the construction of pTrX-HML-105K and pTrX-HML-105R are shown below.

Mutation PCR oligonucleotide primers:

```
TX-105K-1
                                          (SEQ ID NO:43)
     100 101 102 103 104 105 106 107 108 109 110 111
      T   G   A   T   K   K   G   E   V   T   S   D
5'-ACC GGC GCC ACA AAA AAA GGC GAA GTC ACT AGT GAT
       KasI 112 113
 G   S
GGA TCC

TX-105R-1
                                          (SEQ ID NO:44)
     100 101 102 103 104 105 106 107 108 109 110 111
      T   G   A   T   K   R   G   E   V   T   S   D
5'-ACC GGC GCC ACA AAA AAA GGC GAA GTC ACT AGT GAT
       KasI 112 113
 G   S
GGA TCC
```

The appropriate PCR template and primers, and the restriction enzymes to cut the end of the PCR products are listed below (Table 3-2).

TABLE 3-2

| PCR product | PCR upstream primer | PCR reverse primer | PCR template | Restriction enzymes for PCR product |
|---|---|---|---|---|
| (c) | TX-105K-1 | TX-C1 | pTrX | KasI/HindIII |
| (d) | TX-105R-1 | TX-C1 | pTrX | KasI/HindIII |

The PCR products (b) (Table 3-1), (c) and (d) (Table 3-2) were prepared and cut with KasI and HindIII restriction nucleases. The products of the restriction digests (b), (c) and (d) were ligated into a KasI/HindIII-linearized pTrX-HML (1-113) plasmid to generate plasmids pTrX-HML-105H, pTrX-HML-105K and pTrX-HML-105R, respectively.

1-7: Construction of the Plasmids pTrX-HML-75A and pTrX-HML-75A-105H

The two mutant xylanases TrX-HML-75A and TrX-HML-75A-105H are similar to TrX-HML except that Ser at position 75 is replaced by Ala (S75A) in TrX-HML-75A construct, and in TrX-HML-75A-105H Ser at position 75 is replaced by Ala (S75A) and Leu at position 105 is replaced by His (L105H).

The appropriate PCR template and primers, and the restriction enzymes to cut the end of the PCR products are listed below (Table 3-3).

TABLE 3-3

| PCR product | PCR upstream primer | PCR reverse primer | PCR template | Restriction enzymes for PCR product |
|---|---|---|---|---|
| (e) | TX-75A-1 | TX-C1 | pTrX-105H | EcoRI/HindIII |

The EcoRI/HindIII-cut PCR products (a) and (e) (Tables 3-1 and 3-3 respectively) were prepared and ligated into KasI/HindIII-linearized pTrX-HML(1-113) plasmid to generate plasmids pTrX-HML-75A and pTrX-HML-75A-105H respectively.

1-8: Construction of pTrX-HML-75A-105R pTrX-HML-75C-105R, pTrX-HML-75G-105R and pTrX-HML-75T-105R Xylanase mutants TrX-HML-75A-105R, TrX-HML-75C-105R, TrX-HML-75G-105R and TrX-HML-75T-105R are similar to TrX-HML-105R (comprising mutations N10H, Y27M, N29L and L105R), with the exception of an additional single mutation S75A, S75C, S75G and S75T in each of the mutant xylanases, respectively.

The PCR primers with mutations S75C (TX-75C-1; SEQ ID NO:45), S75G (TX75-G-1; SEQ ID NO:46) and S75T (TX-75-T-1; SEQ ID NO:47) are shown below.

Mutation PCR oligonucleotide primers:

```
TX-75C-1
                                          (SEQ ID NO:45)
    69  70  71  72  73  74  75  76  77  78  79  80
     N   G   N   S   Y   L   C   V   Y   G   W   S
5'-T GGG AAT TCA TAC TTA TGC GTC TAT GGC TGG TCT
        EcoRI

81
 R
AG

TX-75G-1
                                          (SEQ ID NO:46)
    69  70  71  72  73  74  75  76  77  78  79  80
     N   G   N   S   Y   L   G   V   Y   G   W   S
5'-T GGG AAT TCA TAC TTA GGC GTC TAT GGC TGG TCT
        EcoRI

81
 R
AG

TX-75T-1
                                          (SEQ ID NO:47)
    69  70  71  72  73  74  75  76  77  78  79  80
     N   G   N   S   Y   L   T   V   Y   G   W   S
5'-T GGG AAT TCA TAC TTA ACC GTC TAT GGC TGG TCT
        EcoRI

81
 R
AG
```

The appropriate PCR template and primers, and the restriction enzymes to cut the end of the PCR products are listed below (Table 3-4).

TABLE 3-4

| PCR product | PCR upstream primer | PCR reverse primer | PCR template | Restriction enzymes for PCR product |
|---|---|---|---|---|
| (f) | TX-75A-1 | TX-C1 | pTrX-HML-105R | EcoRI/HindIII |
| (g) | TX-75C-1 | TX-C1 | pTrX-HML-105R | EcoRI/HindIII |
| (h) | TX-75G-1 | TX-C1 | pTrX-HML-105R | EcoRI/HindIII |
| (i) | TX-75T-1 | TX-C1 | pTrX-HML-105R | EcoRI/HindIII |

The EcoRI-HindIII-cut PCR products (f), (g), (h) and (i) (see Table 3-4) were prepared and ligated into EcoRI/HindIII-linearized pTrX-HML(1-113) plasmid to generate plasmids pTrX-HML-75A-105R, pTrX-HML-75C-105R, pTrX-HML-75G-105R, and pTrX-HML-75T-105R respectively.

1.9: Construction of the Plasmids pTrX-HML-125A and pTrX-HML-125A129E

The mutants TrX-HML-125A and TrX-HML-125A129E were identical to TrX-HML, with the exception of additional mutations Q125A and I129E.

The intact mutant genes were assembled via the ligation of two DNA sequences encoding the 1-121 and the 122-190 regions. The DNA sequence encoding the 1-121 region was created via deletion of the plasmid pTrX-HML by nucleases NheI and MluI. The DNA sequence encoding the 122-190 region was generated via PCR. The PCR primers with mutation Q125A or Q125A/I129E (in bold type) are shown below.

```
TX-125A-1
                                       (SEQ ID NO:48)
 120 121 122 123 124 125 126 127 128 129 130 131
  Q   R   V   N   A   P   S   I   I   G   T
5'-C CAA CGC GTT AAT GCG CCA TCG ATC ATT GGA ACC
        MluI
132 133
 A   T
GCC ACC

TX-125A129E-1
                                       (SEQ ID NO:49)
 120 121 122 123 124 125 126 127 128 129 130 131
  Q   R   V   N   A   P   S   I   E   G   T
5'-C CAA CGC GTT AAT GCG CCA TCG ATC GAG GGA ACC
        MluI
132 133
 A   T
GCC ACC
```

The appropriate PCR template and primers, and the restriction enzymes to cut the end of the PCR product which is the 122-190 sequence, are listed below (Table 3-5).

TABLE 3-5

| PCR product | PCR upstream primer | PCR reverse primer | PCR template | Restriction enzymes for PCR product |
|---|---|---|---|---|
| (j) | TX-125A-1 | TX-C1 | pTrX | MluI/HindIII |
| (k) | TX-125A129E-1 | TX-C1 | pTrX | MluI/HindIII |

The two cut DNA sequences 1-121 and 122-190 together constituting an intact xylanase sequence, were ligated to the NheI/HindIII-linearized plasmid pTrX-(1-113) to generate plasmids pTrX-HML-125A and pTrX-HML 125A129E.

1.10: Construction of the plasmid pTrX-HML-75G-105R-125A129E.

The mutant TrX-75G-105R-125A129E was identical to TrX-HML 75G-105R, with the exception of the additional mutations Q125A and I129E.

The intact mutant genes were assembled via the ligation of two DNA sequences encoding the 1-121 and the 122-190 regions. The DNA sequence encoding the 1-121 region prepared through the deletion of plasmid pTrX-HML-75G-105R with restriction nucleases listed below (Table 3-6).

TABLE 3-6

| Deletion sequence | Precursor plasmid | Restriction enzymes for PCR product |
|---|---|---|
| (A) | pTrX-HML-75G-105R | NheI/MluI |

The DNA sequence encoding the 122-190 region was the same MluI/HindIII-cut PCR product (k) in the Example 1.9 (above).

The cut PCR product (k) and the deletion sequence (A) were ligated to the NheI/HindIII-linearized plasmid pTrX-(1-113) to generate the new plasmids listed below (Table 3-7).

TABLE 3-7

| Deletion product | PCR product | New plasmid |
|---|---|---|
| (A) | (k) | pTrX-HML-75G-105R-125A129E |

1.11: Construction of the Plasmids pTrX-HML-75G-105H-125A129E, pTrX-HML-75A-105H-125A129E and pTrX-HML-75A-105R-125A129E The mutants TrX-HML-75G-105H-125A129E, pTrX-HML-75A-105H-125A129E and pTrX-HML-75A-105R-125A129E were identical to TrX-HML-75G-105R-125A129E, with the exception of the appropriate mutations at residues-75 (S75A or S75G) and -105 (L105H or L105R).

The intact mutant genes were assembled via the ligation of two DNA sequences encoding the 1-101 and the 102-190 regions.

For the preparation of the DNA sequence encoding the 1-101 region, restriction nucleases for the deletion of the appropriate plasmid are listed below (Table 3-8).

TABLE 3-8

| Deletion sequence | Precursor plasmid | Restriction enzymes for PCR product |
|---|---|---|
| (B) | pTrX-HML-75G-105R | NheI/KasI |
| (C) | pTrX-HML-75A-105R | NheI/KasI |

For the preparation of the DNA sequence encoding the 102-190 region, polymerase chain reaction was used. The appropriate PCR primers with mutations at position-105 and the restriction enzymes to cut the end of the PCR product are listed below (Table 3-9).

TABLE 3-9

Plasmid pTrX-HML-75G-105R-125A129E as PCR template.

| PCR product | PCR upstream primer | PCR reverse primer | Restriction enzymes for PCR product |
|---|---|---|---|
| (l) | TX-105H-1 | TX-C1 | KasI/HindIII |
| (m) | TX-105R-1 | TX-C1 | KasI/HindIII |

The cut PCR product ((l) or (m)) and one of the deletion sequences ((B) or (C)) were ligated to the NheI/HindIII-linearized plasmid pTrX-(1-113) to generate the new plasmids listed below (Table 3-10).

TABLE 3-10

| Deletion product | PCR product | New plasmid |
|---|---|---|
| (B) | (l) | pTrX-HML-75G-105H-125A129E |
| (C) | (l) | pTrX-HML-75A-105H-125A129E |
| (C) | (m) | pTrX-HML-75A-105R-125A129E |

1.12. Construction of the Plasmids pTrX-HML-75G-104P105H-125A129E and pTrX-HML-75G-104P105R-125A129E The mutants TrX-HML-75G-104P105H-125A129E and pTrX-HML-75G-104P105R-125A129E were identical to TrX-HML-75G-105H-125A129E and TrX-HML-75G-105R-125A129E respectively, with the exception of an additional mutation of Lys-104 into proline (K104P).

The intact mutant genes were assembled via the ligation of two DNA sequences encoding the 1-101 and the 102-190 regions.

The DNA sequence encoding the 1-101 region for the three new mutants was the same deletion sequence (B) through the cutting of plasmid pTrX-HML-75G-105R by nucleases NheI and KasI in the Example 1.11 (above).

For the preparation of the DNA sequence encoding the 102-190 region, polymerase chain reaction was used. The PCR primers with mutations at residues-104 and 105 (bold type) have been synthesized.

Mutation PCR oligonucleotide primers:

```
TX-104P-105H-1
                                       (SEQ ID NO:50)
    100 101 102 103 104 105 106 107 108 109 110 111
     T   G   A   T   P   H   G   E   V   T   S   D
 5'ACC GGC GCC ACA CCA CAC GGC GAA GTC ACT AGT GAT
        KasI

112
GG

TX-104P-105R-1
                                       (SEQ ID NO:51)
    100 101 102 103 104 105 106 107 108 109 110 111
     T   G   A   T   P   R   G   E   V   T   S   D
 5'ACC GGC GCC ACA CCA CAC GGC GAA GTC ACT AGT GAT
        KasI

112
GG
```

Polymerase chain reaction was conducted. The appropriate primers and restriction enzymes to cut the ends of the PCR product, were listed-below (Table 1-11).

TABLE 1-11

Plasmid pTrX-HML-75G-105R-125A129E as the PCR template.

| PCR product | PCR upstream primer | PCR reverse primer | Restriction enzymes for PCR product |
|---|---|---|---|
| (n) | TX-104P-105H-1 | TX-C1 | KasI/HindIII |
| (o) | TX-104P-105R-1 | TX-C1 | KasI/HindIII |

The cut PCR product (n, or o) and the deletion sequence (B) were ligated to the NheI/HindIII-linearized plasmid pTrX-(1-113) to generate the new plasmids listed below (Table 3-12).

TABLE 3-12

| Deletion product | PCR product | New Plasmid |
|---|---|---|
| (B) | (n) | pTrX-HML-75G-104P-105H-125A129E |
| (B) | (o) | pTrX-HML-75G-104P-105R-125A129E |

1.13. Construction of the Plasmids pTrX-157D-161R-162H-165H; pTrX-HML-75A-105H-125A-129E-132R-135R: pTrX-HML-75A-105H-125A-129E-132R-135R-144R; pTrX-HML-75A-105H-125A-129E-132R-135R-144R-157D-161R-162H-165H; pTrX-HML-75A-105H-125A-135R-144R-157D-161R-162H-165H; and pTrX-HML-75A-105H-125A-129E-135R-144R-157D-161R-162H-165H The mutants: pTrX-157D-161R-162H-165H; pTrX-HML-75A-105H-125A-129E132R-135R; pTrX-HML-75A-105H-125A-129E-132R-135R-144R; pTrX-H 75A-1O5H-125A-129E-132R-135R-144R-157D-161R-162H-165H; pTrX-HML-75A-105H-125A-135R-144R-157D-161R-162H-165H; and pTrX-HML-75A-105H-125A-129E-135R-157D-144R-161R-162H-165H, were prepared essentially as described above using the appropriate primers and templates. The intact mutant genes were assembled via the ligation of two DNA sequences encoding the 1-101 and the 102-190 regions.

Example 2

Characterization of Mutant Xylanases

2-1: Production of Xylanases

The culture conditions comprised a 5 ml culture of overnight innoculant in 2YT medium (16 g bacto-tryptone, 10 g yeast extract, 5 g NaCl, 1 L of water) containing ampicillin (100 mg/L) was added to 2YT medium (1 L) with ampicillin. The cultures were grown with shaking (200 rpm) at 37° C. After 16 hr, cells were harvested.

2-2: Purification of Mutant Xylanases

Protein samples were prepared from cells by first making an extract of the cells by grinding 10 g of the cell paste with 25 g of alumina powder. After grinding to smooth mixture, small amounts (5 mL) of ice cold buffer A (10 mM sodium acetate, pH 5.5 for BcX mutants) or buffer B (10 mM sodium acetate, pH 4.6 for TX mutants) were added and the mixture ground vigorously between additions. The alumina and cell debris were removed by centrifugation of the mixture at 8000×g for 30 min.

Prior to column chromatography, the supernatant was adjusted to pH 4.6 by acetic acid and centrifuged to remove any precipitate. The subsequent method for column chromatography was identical for all mutant xylanases.

Following acidification and centrifugation, the xylanase sample was pumped onto a 50 mL bed volume, CM-sepharose fast flow, cation exchange column (Pharmacia Biotech, Uppsala), equilibrated in 10 mM sodium acetate (pH 4.6). The xylanase was eluted with a 250 mL linear gradient (0 to 0.6M NaCl in 10 mM sodium acetate, pH 4.6) at a flow rate of 1 mL/min. The xylanases elute at 150 to 200 mL of the gradient. Aliquots from the collected fractions are examined by SDS-PAGE, and those fractions having most of the xylanase present were pooled. The purified xylanase was quantified by spectrophotometry at 280 nm using an extinction coefficient between 54,600-53,400 $M^{-1}$, for most mutant TrX xylanases. A typical purification from 10 g of cells yielded 25 mg of xylanase.

2-3: Standard Assay for the Measurement of Enzymatic Activity

The quantitative assay determined the number of reducing sugar ends generated from soluble xylan. The substrate for this assay was the fraction of birchwood xylan which dissolved in water from a 5% suspension of birchwood xylan (Sigma Chemical Co.). After removing the insoluble fraction, the supernatant was freeze dried and stored in a dessicator. The measurement of specific activity was performed as follows: Reaction mixtures containing 100 µL of 30 mg/mL xylan previously diluted in assay buffer (50 mM sodium citrate, pH 5.5 or the pH optimum of the tested xylanase), 150 µL assay buffer, and 50 µL of enzyme diluted in assay buffer were incubated at 40° C. At various time intervals 50 µL portions were removed and the reaction stopped by diluting in 1 mL of 5 mM NaOH. The amount of reducing sugars was determined with the hydroxybenzoic acid hydrazide reagent (HBAH) (Lever, 1972, Analytical Biochem 47:273-279). A unit of enzyme activity was defined as that amount generating 1 µmol reducing sugar in 1 minute at 40° C.

For comparison of the specific activities between mutant and native xylanases the specific activities of a mutant xylanase was converted to a relative activity. The relative activity is calculated as a percentage, by dividing the specific activity of the mutant enzyme by the specific activity of the native xylanase.

TABLE 4

Relative activity of TrX and native xylanases at 40° C.

| Xylanase | Relative activity (%) |
|---|---|
| native TrX | 100* |
| TrX-105H | 97 |
| TrX-75A | 95 |
| TrX-HML-75A-105H | 95 |
| TrX-HML-75A-105R | 93 |

*specific activity of native TrX xylanase determined to be 770 U/mg.

The results depicted in Table 4 indicate that the specific enzymatic activities of the mutant xylanases at 40° C. have not been changed significantly as compared to the native xylanase.

Example 3

Thermophilicity of Mutant Xylanases

Thermophilicity was examined to test the effect of different temperatures on the enzymatic hydrolysis of soluble xylan by different mutant xylanases.

The assay procedure was similar to the standard assay with changes in the incubation temperature and time. The xylanases (15 µg/mL) and soluble xylan substrate, in 50 mM sodium citrate buffer of pH 5.5, were mixed and incubated in a circulating water bath at different temperatures. After a 30 min incubation, the amount of reducing sugars released from xylan was determined by HBAH analysis and was calculated as a relative activity, with the value at 40° C. representing 100%.

The effect of temperature on the hydrolysis of xylan by TrX and TrX-75A xylanases is shown in FIG. 3. The mutant TrX-75A xylanase bearing a single S75A mutation, showed greater enzymatic activity than the natural TrX xylanase at 50, 55, 60 and 65° C. Further, the S75A mutation in the TrX-HML-75A mutant xylanase exhibited greater enzymatic activity than the TrX-HML parent xylanase at 70° C. and 75° C. (FIG. 4). These results suggest that the S75A mutation improves the thermophilicity of TrX and TrX-HML xylanases.

Mutation of Leu 105 to His (L105H) in TrX-HML xylanase to produce the TrX-HML-105H mutant xylanase also exhibited increased enzymatic activity over the parent TrX-HML xylanase at 70 and 75° C. (FIG. 4).

Noteworthy, the combination mutant TrX-HML-75A-105H xylanase exhibited a maximum enzymatic activity at a temperature of 70° C. and further showed greater enzymatic activity than either TrX-HML-75A or TrX-HML-105H single mutant xylanases at 70° C. (FIG. 4). These results suggest the effects of the two mutations S75A and L105H on the thermophilicity of the mutant xylanase are additive or complementary.

Substitution of Asn at position 157 with Asp, Ala at position 161 with Arg (A161R), Gln at position 162 with His (Q162H), and Thr at position 165 with His (T165H) to produce TrX-157D-161R-162H-165H was neutral with respect to, or resulted in a slight increase in, the thermophilicity of this enzyme over that of the parent TrX enzyme (FIG. 15).

A series of TrX-HML xylanases bearing mutations at position-105 were constructed to determine those amino acid residues which enhance the thermophilicity of the parent TrX-HML enzyme (FIG. 5). Three mutants at position 105, TrX-HML-105H, TrX-HML-105R and TrX-HML-105K showed greater enzymatic activity than the precursor TrX-HML enzyme at 70° C. or higher. The three mutations involve substituting Leu at position 105, a relatively hydrophobic branched-chain amino acid with His, Arg and Lys, amino acid residues that are hydrophilic or positively charged or basic. Such mutations enhanced the thermophilicity of the mutant xylanases.

The combination mutant TrX-HML-75A-105R xylanase showed a similar temperature-activity profile to TrX-HML-75A-105H xylanase, suggesting that the S75A and L105R mutations, like the effect of the S75A and L105H are additive or complementary. These results further suggest that basic residues at position 105 enhance the thermophilicity of the xylanases.

In another series of mutant xylanases, position-75 of TrX-HML-105R was mutated to determine those residues which exhibited enhanced thermophilicity (FIG. 6). Three genetically modified xylanase mutants, TrX-HML-75C-105R, TrX-HML-75A-105R and TrX-HML-75G-105R showed greater enzymatic activity than either the precursor TrX-HML-105R xylanase or the TrX-HML xylanase at temperatures greater than 60° C. Interestingly, the fourth mutant TrX-HML-75T-105R xylanse xylanase showed no enhancement in thermophilicity over the precursor TrX-HML-105R xylanase that has a natural Ser residue at position 75. The mutant threonine residue at position 75, like the natural Ser 75 residue found in TrX and TrX-HML parent xylanases, is a hydrophilic amino acid. Collectively, the mutations which involve replacing Ser, a polar amino acid at position 75 with small, nonpolar amino acids, such as but not wishing to be limiting Ala, Gly or Cys lead to an increase in the thermophilicity of the xylanase.

Figure 7:
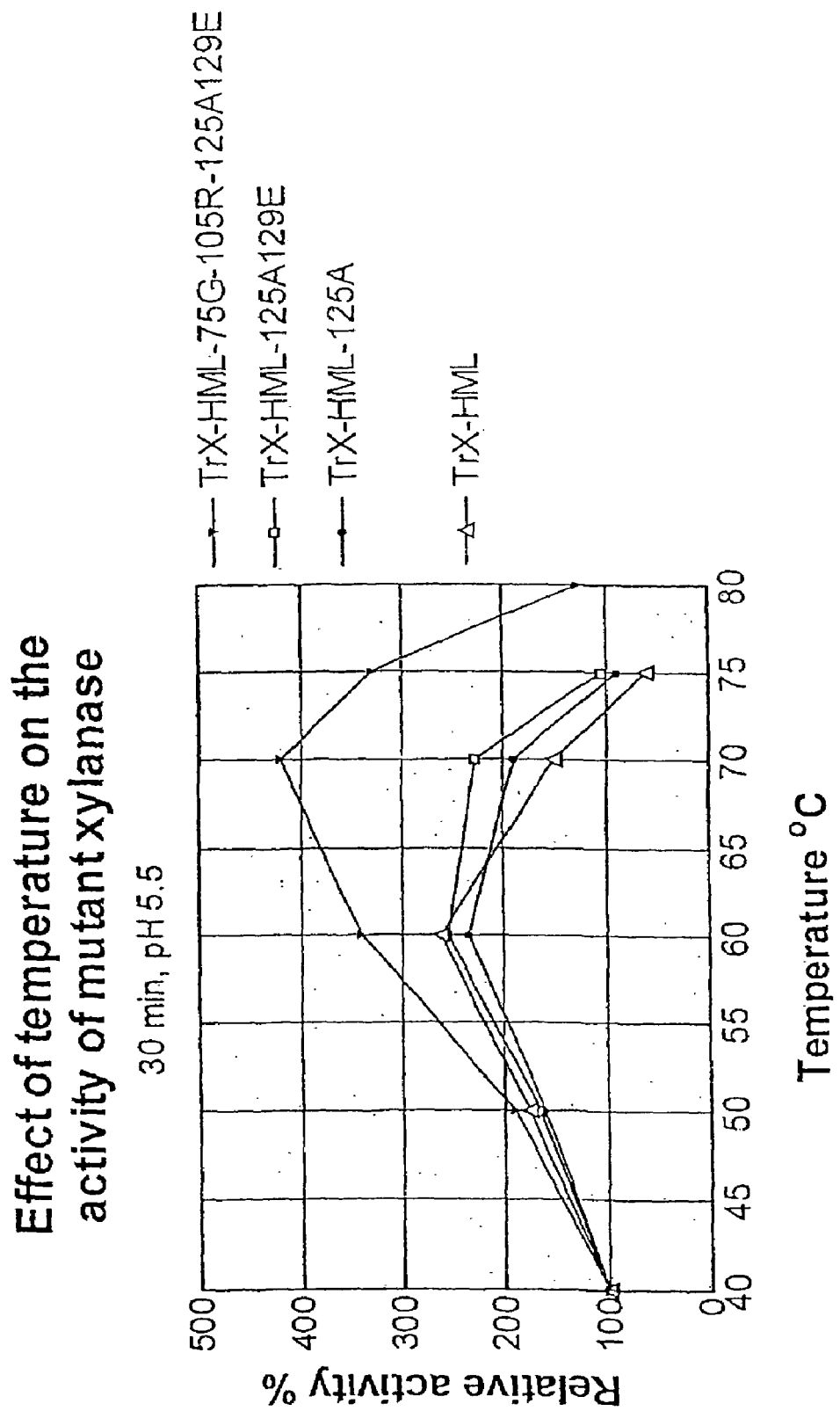
FIG. 7 shows the effect of temperature on the enzymatic activity of modified xylanase enzyme TrX-HML, TrX-HML-125A, TrX-HML 125A129E and TrX-HML75G-105R-125A129E (TrX-HML-GRAE) at pH 5.5 during 30 min incubations. The data are normalized to the activity observed at 40° C.
Figure 8:
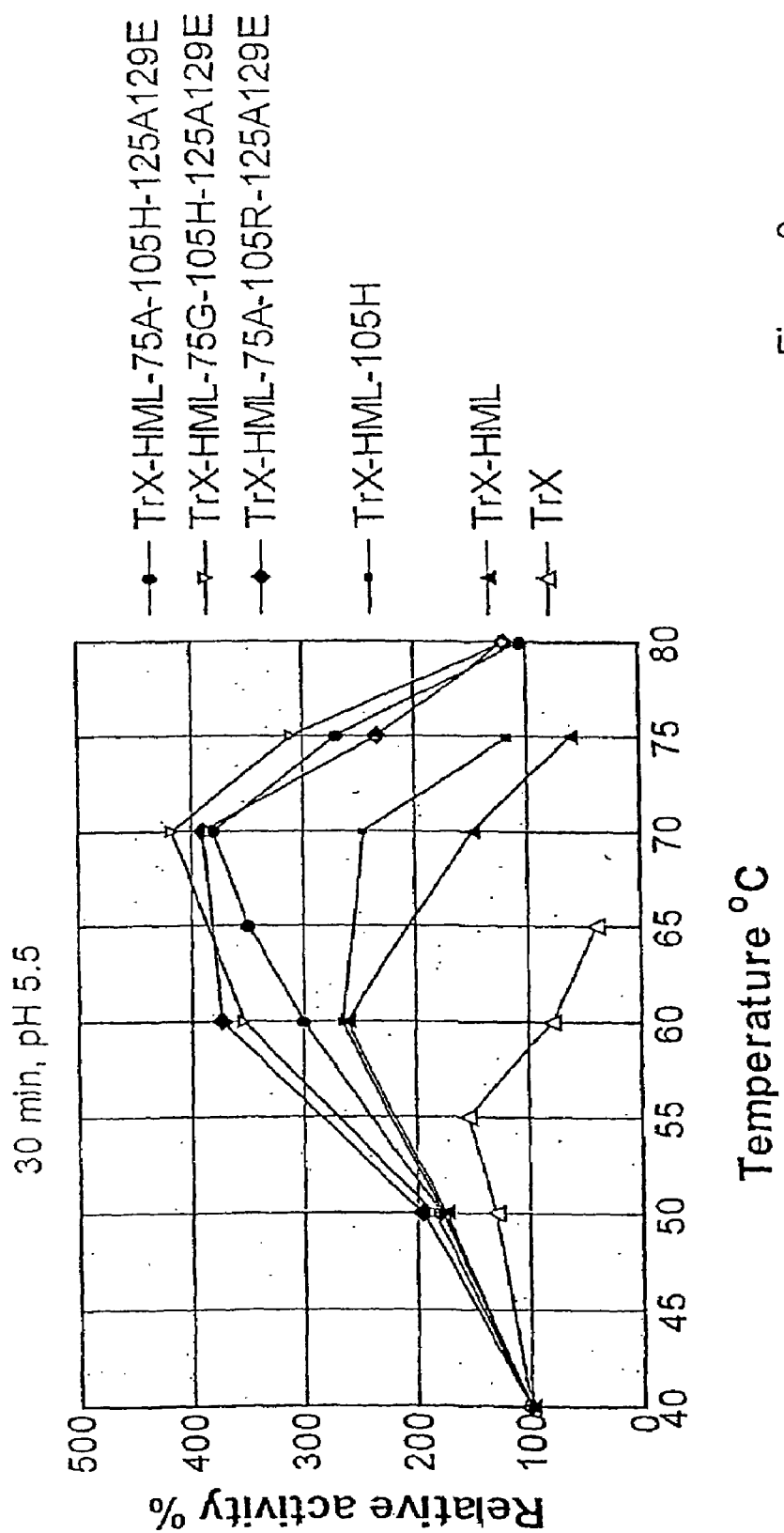
FIG. 8 shows the effect of temperature on the enzymatic activity of modified xylanase enzymes:
TRX-HML;
TrX-HML-105H;
TrX-HML-75A-105H-125A129E (TrX-HML-AHAE);
TrX-HML-75G-105H-125A129E (TrX- HML-GHAE); and
TrX-HML-75A-105R-125A129E (TrX-HML-ARAE)

In another series, a mutation of the residue Gln-125 of TrX-HML to Ala (Q125A) resulted in greater activity at higher activity at higher temperatures (FIG. 7). A second mutation of Ile-129 to Glu (I129E) also resulted a modest improvement of the thermophilicity of the xylanase. The advantageous mutations at residues-75, 105, 125 and 129 were then combined together to yield a mutant TrX-HML-75G-105R-125A129E and it showed further improvement of activity at higher temperatures (FIG. 7). Other combination mutants with mutations at residues-75 (S75A or S75G) and -105 (L105H or L105R) have also demonstrated the same improvement of activity at higher temperature (FIG. 8).

In the final series, a mutation of Lys-104 to proline (K104P) also produced a xylanase with much improved thermophilicity similar to the advantageous mutations S75G, L105R or H, Q125A and I129E (FIG. 9).

Example 4

Alkalophilicity of Mutant Xylanases

The alkalophilicity of genetically modified xylanases was examined to test the effect that different pH conditions had on the enzymatic hydrolysis of soluble xylan by mutant xylanases. The assay procedure was similar to the standard assay with changes in the incubation temperature and time. Aliquots of genetically modified xylanases (15 µg/mL) and soluble xylan substrate in 50 mM sodium citrate buffers which varied between pH 4-7 were incubated together at 65° C. Following 30 min incubations, the amount of reducing sugars released from the xylan substrate was determined by HBAH analysis and the enzymatic activity as a function of pH was calculated for a variety of mutant xylanases with the maximal activity taken as 100%.

The effect of pH conditions on the enzymatic activity of single mutant TrX-75A xylanase is shown in FIG. 10. At 55° C., the TrX-75A mutant xylanase displayed maximum activity at a pH which was higher (pH 5.5) than the pH at which the native TrX enzyme exhibits maximum activity (pH 5.0). An increase in enzymatic activity was also exhibited by the mutant in comparison to the natural TrX xylanase at pH conditions of 6.0 and 6.5.

A similar contribution to improved alkalophilicity by the S75A in TrX-75A was also observed for the TrX-HML-75A over the parent TrX-HML xylanase at pH conditions between 6.5 and 7 (FIG. 11).

The L105H mutation in the TrX-HML-105H mutant xylanase also increased the enzymatic activity over the parent TrX-HML xylanase at pH 6.5 and 7.0 (FIG. 11). Interestingly, the combination mutant TrX-75A-105H xylanase showed greater enzymatic activity than either TrX-HML-75A or TrX-HML-105H single mutant xylanases at pH 6.5 and 7.0 (FIG. 11), suggesting that the effects of the S75A mutation and the L105H mutation on the alkalophilicity of the xylanase are additive or complementary.

A series of genetically modified xylanases modified at position 105 were constructed to determine those residues which promote increased alkalophilicity in modified xylanases (FIG. 12). Three mutant xylanases bearing three mutations at position 105, TrX-HML-105H, TrX-HML-105R and TrX-HML-105K showed greater enzymatic activity than the precursor TrX-HML xylanase at pH conditions of 6.5 and 7.0. Collectively, the mutations which lead to increases in alkalophilicity, represent a change of the amino acid at position 105 from a branched chain relatively hydrophobic Leu residue to a residue which is hydrophilic, positively charged or basic.

Without wishing to be bound by theory, the hydrophilic, positively charged, or basic residues may facilitate intramolecular packing with other atoms that are juxtapositioned in the same vicinity in the tertiary structure of the xylanase. These residues may stabilize the three dimensional structure of the enzyme against structural perturbations in the molecule which may arise via the titration of several ionizable side-chains of amino aids in other regions of the molecule. Again, without wishing to be bound by theory, the basic ionized form of the side chain may be important in altering the pH activity profile of the enzyme, as at pH conditions between 6 and 7, Arg and Lys residues have side-chains which likely remain protonated. In contrast, His residues having a pKa of approximately 6 in solution for its imidazole moiety could be present in either a protonated or unprotonated form. However, it is known to those skilled in the art that the polarity of the substituents surrounding an amino acid side chain may affect its pKa value. For example, the side chain of a His residue in a polar or hydrophobic region of a protein may exhibit a pKa of 6 whereas the same side-chain in a hydrophobic or apolar environment may exhibit a pKa of 7 or greater.

In another study, mutations were constructed at position 75 of TrX-HML to determine which residues promote increased, alkalophilicity in modified xylanases (FIG. 13). Four xylanases bearing mutations at position 75, TrX-HML-75C-105R, TrX-HML-75A-105R, TrX-75G-105R and TrX-HML-75T-105R showed greater enzymatic activity at pH conditions of 6.0, 6.5 and 7.0, compared to the precursors TrX-HML and TrX-HML-105R xylanases.

The two mutations Q125A and I129E in the mutant xylanases TrX-HML-125A and TrX-HML-125A129, which successfully increased the thermophilicity of the enzymes, have generally not affected their activity at higher pH, as compared to TrX-HML. This specific improvement of thermophilicity but not the alkalophilicity of xylanase, was also demonstrated in a comparison of TrX-HML-75A-105H and the combination mutants TrX-HML-75A-105H-125A129E (FIG. 14). This has also been observed in other mutants TrX-HML-75G-105H-125A129E (FIG. 14), TrX-HML-75A-105R-125A129E and TrX-HML-75G-105R-125A129E.

The substitution of an acidic amino acid at position 157, and basic amino acids at positions 161, 162 and 165 with or without basic amino acid substitutions at positions 132, 135 and 144 also increased alkalophilicity. TrX-HML-AHAE-RR-DRHH, or TrX-HML-AHAE-RRR-DRRH (see full description of substituted amino acids in Table 2) each exhibited an increase in alkalophilicity (FIGS. 18 and 19). These enzymes are also characterized as exhibiting a MEP of about pH 7.0 (FIGS. 18 and 19).

A further increase in alkalophilicity over those outlined above was also obtained by substituting an acidic amino acid at position 157, and basic amino acids at positions 135, 144, 161, 162, 165, and leaving the amino acid at positions 129 and 132 in their native state, for example, TrX-HML-AHA-RR-DRHH (FIGS. 18 and 19). The MEP of TrX-HML-AHA-RR-DRHH is about pH 7.4 (FIGS. 18 and 19).

In summary, improved alkalophilic mutant TrX xylanases may be constructed through i) mutation of Ser 75 to small apolar residues. Without wishing to be limiting these residues may comprise Gly, Ala, and Cys; ii) mutation of Ser 75 to Thr; iii) mutation of Leu 105 to a basic residue such as but not limited to Arg, Lys or His; iv) mutation of Ala 132, Tyr 135, His 144, Gln 161, Gln 162, Thr 165 or a combination thereof to a basic amino acid, for example but not limited to, Arg, Lys or His; v) mutation of Asn 157 to an acidic amino acid Asp or Glu, or vi) combination of mutations described in i) or ii) with those described in iii) and iv) for the improvement of alkalophilicity.

While the present invention has described mutant xylanases which exhibit improved thermophilicity and alkalophilicity and the benefits associated with these enzymes in the production of paper pulp, these mutant xylanases may also be of use in other industrial processes, for example but not limited to the washing of precision devices and semiconductors. Further, by virtue their increased thermophilicity, and thermostability the mutant xylanases may be used in chemical processes that employ small quantities of denaturants or detergents or in the presence of solvents, for example but not limited to small amounts of apolar solvents such as but not limited to hexane, dioxanes, carbontetrachloride, benzene, ethers, chloroform, acetic acid and methylene chloride, and polar solvents such as but not limited to acetone, alcohols, dimethylformamide, acetonitrile, sulfolane, dimethylsulfoxide and water.

The present invention has been described with regard to preferred embodiments. However, it will be obvious to persons skilled in the art that a number of variations and modifications can be made without departing from the scope of the invention as described herein.

All references and citations are herein incorporated by reference

REFERENCES

Arase, A., Yomo, T., Urabe, I., Hata, Y., Katsube, Y. and Okada, H. (1993) FEBS Lett. 316:123-127.
Casimir-Schenkel, J., Davis, S., Fiechter, a., Gysin, B., Murray, E., Perrolaz, J.-J. and Zimmermann, W. European Patent application no. 91810652.7, published on Apr. 3, 1992. Publication no. 0 473 545 A2.
Campbell, R. L., Rose, D. R., Sung, W. L., Yaguchi, M. and Wakarchuk, W. U.S. Pat. No. 5,405,769 issued on Apr. 11, 1995.
Campbell, R. L., Rose, D. R., Sung, W. L., Yaguchi, M. and Wakarchuk, W. PCT publication no. WO 94/24270, published on 27 Oct. 1994.
Fisk, R. S. and Simpson, C. (1993) in Stability and Stabilization of Enzymes, edited by W. J. J. van den Tweel, A. Harder and R. M. Buitelaar, published by Elsevier Science Publishers B. V. pp 323-328.
Gruber, K., Klintschar, G., Hayn, M, Schlacher, A., Steiner, W. and Kratky, C. (1998) Biochemistry 37:13475-13485.
Irwin, D., Jung, E. D. and Wilson, D. B. (1994) Appl. Environ. Microbiol. 60:763-770.
Lee, S. L., Forsberg, C. W., and Rattray, J. B. (1987) Appl. Environ. Microbiol. 53:644-650.
Lüthi, E., Jasmat, N. B., and Bergquist, P. L. (1990) Appl. Environ. Microbiol. 56:2677-2683.
Mathrani, I. M. and Ahring, B. K. (1992) Appl. Microbiol. Biotechnol. 38:23-27.
Misset, O. (1993) in Stability and Stabilization of Enzymes, edited by W. J. J. van den Tweel, A Harder and R M. Buitelaar; published by Elsevier Science Publishers B. V. pp 111-131.
Nissen A. M., Anker, L., Munk, N., and Lange, N. K. in Xylans and Xylanases, edited by J. Visser, G. Beldman, M. A. Kusters-van Someren and A. G. J. Voragen, published by Elsevier, Amsterdam, 1992. p 325-337.
Sakka, K., Kojima Y., Kondo, T., Karita, S., Ohmiya, K. and Shimada, K. (1993) Biosci. Biotech. Biochem. 57:273-277.
Simpson, H. D., Haufler, U. R., and Daniel, R. M. (1991) Biochem. J. (1991) 277:413-417.
Sung.. W. L., Yao. F.-L., Zahab, D. M. and Narang, S. A. (1986) Proc. Natl. Acad. Sci. USA 83:561-565.
Sung, W. L., Luk, C. K., Zahab, D. M. and Wakarchuk, W. (1993) Protein Expression Purif. 4:200-206.
Sung, W. L., Luk, C. K., Chan, B., Wakarchuk, W., Yaguchi, M., Campbell, R., Willick, G., Ishikawa, K. and Zabab, D. M. (1995) Biochem. Cell. Biol. 73:253-259.
Sung, W. L., Yaguchi, M and Ishikawa, K. U.S. Pat. No. 5,759,840, issued on Jun. 2, 1998.
Sung, W. L., Yaguchi, M and Ishikawa, K. U.S. Pat. No. 5,866,408, issued on Feb. 2, 1999
Tolan, J. S. and Vega Canovas, R. (1992) Pulp & Paper Canada 93-116-119).
Wakarchuck W. W., Sung, W. L., Campbell, R. L., Cunningham, A., Watson, D. C. and Yaguchi, M. (1994) Protein Engineering 7:1379-1386.
Wilson, D. B., Jung, E. D., Changas, G. S., Irvin, D. C. PCT international publication on 11 May 1995, Publication No. WO 95/12668.
Winterhalter C. and Liebl, W. (1995) Appl. Environ. Bicrobiol. 61:1810-1815.
Zappe, H., Jones, W. A., and Woods, D. R. (1987) Appl. Microbiol. Biotechnol. 27:57-63.
Zappe, H., Jones, W. A., and Woods, D. R. (1990) Nucleic Acids Res. 18:2179.

---

The embodiments of the invention in which an exclusive property of privilege is claimed are defined as follows:

1. A modified xylanase comprising a substituted amino acid residue at position 75, said position determined from sequence alignment of said modified xylanase with *Trichoderma reesei* xylanase II amino acid sequence defined in SEQ ID NO:16, wherein said modified xylanase exhibits improved thermophilicity, alkalophilicity, or a combination thereof, in comparison to a corresponding native xylanase.

2. The modified xylanase of claim 1, wherein said substituted amino acid at position 75 is selected from the group consisting of a non-polar and a polar amino acid.

3. The modified xylanase of claim 2, wherein said substituted amino acid at position 75 is selected from the group consisting of Ala, Cys and Gly.

4. The modified xylanase of claim 3, wherein said modified xylanase is derived from a Family 11 xylanase.

5. The modified xylanase of claim 4, wherein said Family 11 xylanase is a *Trichoderma reesei* xylanase.

6. The modified xylanase of claim 3, further comprising a His at position 10, a Met at position 27 and a Leu at position 29 (HML).

7. The modified xylanase of claim 6, further comprising a basic amino acid at position 105.

8. The modified xylanase of claim 7, wherein said basic amino acid at position 105 is selected from the group consisting of His, Lys and Arg.

9. The modified xylanase of claim 8, wherein the xylanase is a Family 11 xylanase.

10. The modified xylanase of claim 9, wherein said Family 11 xylanase is a *Trichoderma reesei* xylanase.

11. The modified xylanase of claim 7, further comprising a non-polar substituted amino acid residue at position 125 and an acidic substituted amino acid residue at position 129.

12. The modified xylanase of claim 11, wherein said amino acid at position 125 is Ala.

13. The modified xylanase of claim 11, wherein said acidic substituted amino acid at position 129 is Glu.

14. The modified xylanase of claim 11, further comprising a non-polar substituted amino acid residue at position 104.

15. The modified xylanase of claim 14, wherein said non-polar substituted amino acid at position 104 is a Pro.

16. The modified xylanase of claim 11, further comprising a basic substituted amino acid residue at position 132, and a basic substituted amino acid residue at position 135.

17. The modified xylanase of claim 11, further comprising a basic substituted amino acid residue at position 135 and a basic substituted amino acid residue at position 144.

18. The modified xylanase of claim 17, further comprising a substituted amino acid residue at position 157, a substituted amino acid residue at position 161, a substituted amino acid at position 162, and a substituted amino acid residue at position 165, each of said substituted amino acids at positions 161, 162 and 165 is a basic amino acid and said substituted amino acid residue at position 157 is an acidic amino acid.

19. The modified xylanase of claim 16, further comprising a substituted amino acid at position 144, a substituted amino acid residue at position 157, a substituted amino acid at position 161, a substituted amino acid at position 162, and a substituted amino acid at position 165, each of said substituted amino acids at positions 144, 161, 162 and 165 is a basic amino acid and said substituted amino acid residue at position 157 is an acidic amino acid.

20. A modified xylanase according to claim 1, wherein said modified xylanase has a maximum effective temperature (MET) between about 69° C. and about 78° C., or wherein said modified xylanase has a maximum effective pH (MEP) between about pH 5.8 and about pH 7.6, and wherein said modified xylanase is a Family 11 xylanase obtained from a *Trichoderma* sp.

21. The modified xylanase of claim 20, wherein said MET is between about 70° and about 75° C.

22. The modified xylanase of claim 20, wherein said modified xylanase has a maximum effective pH (MEP) between about pH 5.8 and about pH 7.6 and has a maximum effective temperature (MET) between about 69° C. and about 78° C.

23. The modified xylanase of claim 21, wherein said modified xylanase has a maximum effective pH (MEP) between about pH 6.5 and about pH 7.4.

24. The modified xylanase of claim 2, wherein said substituted amino acid at position 75 is a non-polar amino acid.

25. The modified xylanase of claim 24, wherein said non-polar amino acid is selected from the group consisting of Ala and Gly.

* * * * *

SEQUENCE LISTING

```
<160> NUMBER OF SEQ ID NOS: 78

<210> SEQ ID NO 1
<211> LENGTH: 184
<212> TYPE: PRT
<213> ORGANISM: Aspergillus niger

<400> SEQUENCE: 1
```

```
Ser Ala Gly Ile Asn Tyr Val Gln Asn Tyr Asn Gly Asn Leu Gly Asp
1               5                   10                  15

Phe Thr Tyr Asp Glu Ser Ala Gly Thr Phe Ser Met Tyr Trp Glu Asp
            20                  25                  30

Gly Val Ser Ser Asp Phe Val Val Gly Leu Gly Trp Thr Thr Gly Ser
        35                  40                  45

Ser Asn Ala Ile Thr Tyr Ser Ala Glu Tyr Ser Ala Ser Gly Ser Ser
    50                  55                  60

Ser Tyr Leu Ala Val Tyr Gly Trp Val Asn Tyr Pro Gly Ala Glu Tyr
65                  70                  75                  80

Tyr Ile Val Glu Asp Tyr Gly Asp Tyr Asn Pro Cys Ser Ser Ala Thr
                85                  90                  95

Ser Leu Gly Thr Val Tyr Ser Asp Gly Ser Thr Tyr Gln Val Cys Thr
            100                 105                 110

Asp Thr Arg Ile Asn Glu Pro Ser Ile Thr Gly Thr Ser Thr Phe Thr
        115                 120                 125

Gln Tyr Phe Ser Val Arg Glu Ser Thr Arg Thr Ser Gly Thr Val Thr
    130                 135                 140

Val Ala Asn His Phe Asn Phe Trp Ala Gln His Gly Phe Gly Asn Ser
145                 150                 155                 160

Asp Phe Asn Tyr Gln Val Met Ala Val Glu Ala Trp Ser Gly Ala Gly
                165                 170                 175

Ser Ala Ser Val Thr Ile Ser Ser
            180

<210> SEQ ID NO 2
<211> LENGTH: 185
<212> TYPE: PRT
<213> ORGANISM: Aspergillus tubingensis

<400> SEQUENCE: 2

Ser Ala Gly Ile Asn Tyr Val Gln Asn Tyr Asn Gln Asn Leu Gly Asp
1               5                   10                  15

Phe Thr Tyr Asp Glu Ser Ala Gly Thr Phe Ser Met Tyr Trp Glu Asp
            20                  25                  30

Gly Val Ser Ser Asp Phe Val Val Gly Leu Gly Gly Trp Thr Thr Gly
        35                  40                  45

Ser Ser Asn Ala Ile Thr Tyr Ser Ala Glu Tyr Ser Ala Ser Gly Ser
    50                  55                  60

Ala Ser Tyr Leu Ala Val Tyr Gly Trp Val Asn Tyr Pro Gln Ala Glu
65                  70                  75                  80

Tyr Tyr Ile Val Glu Asp Tyr Gly Asp Tyr Asn Pro Cys Ser Ser Ala
                85                  90                  95

Thr Ser Leu Gly Thr Val Tyr Ser Asp Gly Ser Thr Tyr Gln Val Cys
            100                 105                 110

Thr Asp Thr Arg Ile Asn Glu Pro Ser Ile Thr Gly Thr Ser Thr Phe
        115                 120                 125

Thr Gln Tyr Phe Ser Val Arg Glu Ser Thr Arg Thr Ser Gly Thr Val
    130                 135                 140

Thr Val Ala Asn His Phe Asn Phe Trp Ala His His Gly Phe His Asn
145                 150                 155                 160

Ser Asp Phe Asn Tyr Gln Val Val Ala Val Glu Ala Trp Ser Gly Ala
                165                 170                 175

Gly Ser Ala Ala Val Thr Ile Ser Ser
            180                 185
```

```
<210> SEQ ID NO 3
<211> LENGTH: 185
<212> TYPE: PRT
<213> ORGANISM: Bacillus circulans

<400> SEQUENCE: 3

Ala Ser Thr Asp Tyr Trp Gln Asn Trp Thr Asp Gly Gly Gly Ile Val
 1               5                  10                  15

Asn Ala Val Asn Gly Ser Gly Gly Asn Tyr Ser Val Asn Trp Ser Asn
             20                  25                  30

Thr Gly Asn Phe Val Val Gly Lys Gly Trp Thr Thr Gly Ser Pro Phe
         35                  40                  45

Arg Thr Ile Asn Tyr Asn Ala Gly Val Trp Ala Pro Asn Gly Asn Gly
     50                  55                  60

Tyr Leu Thr Leu Tyr Gly Trp Thr Arg Ser Pro Leu Ile Glu Tyr Tyr
 65                  70                  75                  80

Val Val Asp Ser Trp Gly Thr Tyr Arg Pro Thr Gly Thr Tyr Lys Gly
                 85                  90                  95

Thr Val Lys Ser Asp Gly Gly Thr Tyr Asp Ile Tyr Thr Thr Thr Arg
            100                 105                 110

Tyr Asn Ala Pro Ser Ile Asp Gly Asp Arg Thr Thr Phe Thr Gln Tyr
        115                 120                 125

Trp Ser Val Arg Gln Ser Lys Arg Pro Thr Gly Ser Asn Ala Thr Ile
130                 135                 140

Thr Phe Thr Asn His Val Asn Ala Trp Lys Ser His Gly Met Asn Leu
145                 150                 155                 160

Gly Ser Asn Trp Ala Tyr Gln Val Met Ala Thr Glu Gly Tyr Gln Ser
                165                 170                 175

Ser Gly Ser Ser Asn Val Thr Val Trp
            180                 185

<210> SEQ ID NO 4
<211> LENGTH: 201
<212> TYPE: PRT
<213> ORGANISM: Bacillus pumilus

<400> SEQUENCE: 4

Arg Thr Ile Thr Asn Asn Glu Met Gly Asn His Ser Gly Tyr Asp Tyr
 1               5                  10                  15

Glu Leu Trp Lys Asp Tyr Gly Asn Thr Ser Met Thr Leu Asn Asn Gly
             20                  25                  30

Gly Ala Phe Ser Ala Gly Trp Asn Asn Ile Gly Asn Ala Leu Phe Arg
         35                  40                  45

Lys Gly Lys Lys Phe Asp Ser Thr Arg Thr His His Gln Leu Gly Asn
     50                  55                  60

Ile Ser Ile Asn Tyr Asn Ala Ser Phe Asn Pro Ser Gly Asn Ser Tyr
 65                  70                  75                  80

Leu Cys Val Tyr Gly Trp Thr Gln Ser Pro Leu Ala Glu Tyr Tyr Ile
                 85                  90                  95

Val Asp Ser Trp Gly Thr Tyr Arg Pro Thr Gly Ala Tyr Lys Gly Ser
            100                 105                 110

Phe Tyr Ala Asp Gly Gly Thr Tyr Asp Ile Tyr Glu Thr Thr Arg Val
        115                 120                 125

Asn Gln Pro Ser Ile Ile Gly Ile Ala Thr Phe Lys Gln Tyr Trp Ser
130                 135                 140
```

```
Val Arg Gln Thr Lys Arg Thr Ser Gly Thr Val Ser Val Ser Ala His
145                 150                 155                 160

Phe Arg Lys Trp Glu Ser Leu Gly Met Pro Met Gly Lys Met Tyr Glu
                165                 170                 175

Thr Ala Phe Thr Val Glu Gly Tyr Gln Ser Ser Gly Ser Ala Asn Val
            180                 185                 190

Met Thr Asn Gln Leu Phe Ile Gly Asn
        195                 200

<210> SEQ ID NO 5
<211> LENGTH: 185
<212> TYPE: PRT
<213> ORGANISM: Bacillus subtilis

<400> SEQUENCE: 5

Ala Ser Thr Asp Tyr Trp Gln Asn Trp Thr Asp Gly Gly Gly Ile Val
1               5                   10                  15

Asn Ala Val Asn Gly Ser Gly Gly Asn Tyr Ser Val Asn Trp Ser Asn
            20                  25                  30

Thr Gly Asn Phe Val Val Gly Lys Gly Trp Thr Thr Gly Ser Pro Phe
        35                  40                  45

Arg Thr Ile Asn Tyr Asn Ala Gly Val Trp Ala Pro Asn Gly Asn Gly
    50                  55                  60

Tyr Leu Thr Leu Tyr Gly Trp Thr Arg Ser Pro Leu Ile Glu Tyr Tyr
65                  70                  75                  80

Val Val Asp Ser Trp Gly Thr Tyr Arg Pro Thr Gly Thr Tyr Lys Gly
                85                  90                  95

Thr Val Lys Ser Asp Gly Gly Thr Tyr Asp Ile Tyr Thr Thr Thr Arg
            100                 105                 110

Tyr Asn Ala Pro Ser Ile Asp Gly Asp Arg Thr Thr Phe Thr Gln Tyr
        115                 120                 125

Trp Ser Val Arg Gln Ser Lys Arg Pro Thr Gly Ser Asn Ala Thr Ile
    130                 135                 140

Thr Phe Ser Asn His Val Asn Ala Trp Lys Ser His Gly Met Asn Leu
145                 150                 155                 160

Gly Ser Asn Trp Ala Tyr Gln Val Met Ala Thr Glu Gly Tyr Gln Ser
                165                 170                 175

Ser Gly Ser Ser Asn Val Thr Val Trp
            180                 185

<210> SEQ ID NO 6
<211> LENGTH: 211
<212> TYPE: PRT
<213> ORGANISM: Clostridium acetobutylicum

<400> SEQUENCE: 6

Ser Ala Phe Asn Thr Gln Ala Ala Pro Lys Thr Ile Thr Ser Asn Glu
1               5                   10                  15

Ile Gly Val Asn Gly Gly Tyr Asp Tyr Glu Leu Trp Lys Asp Tyr Gly
            20                  25                  30

Asn Thr Ser Met Thr Leu Lys Asn Gly Gly Ala Phe Ser Cys Gln Trp
        35                  40                  45

Ser Asn Ile Gly Asn Ala Leu Phe Arg Lys Gly Lys Phe Asn Asp
    50                  55                  60

Thr Gln Thr Tyr Lys Gln Leu Gly Asn Ile Ser Val Asn Tyr Asn Cys
65                  70                  75                  80
```

```
Asn Tyr Gln Pro Tyr Gly Asn Ser Tyr Leu Cys Val Tyr Gly Trp Thr
             85                  90                  95

Ser Ser Pro Leu Val Glu Tyr Tyr Ile Val Asp Ser Trp Gly Ser Trp
            100                 105                 110

Arg Pro Pro Gly Gly Thr Ser Lys Gly Thr Ile Thr Val Asp Gly Gly
            115                 120                 125

Ile Tyr Asp Ile Tyr Glu Thr Thr Arg Ile Asn Gln Pro Ser Ile Gln
        130                 135                 140

Gly Asn Thr Thr Phe Lys Gln Tyr Trp Ser Val Arg Arg Thr Lys Arg
145                 150                 155                 160

Thr Ser Gly Thr Ile Ser Val Ser Lys His Phe Ala Ala Trp Glu Ser
                165                 170                 175

Lys Gly Met Pro Leu Gly Lys Met His Glu Thr Ala Phe Asn Ile Glu
            180                 185                 190

Gly Tyr Gln Ser Ser Gly Lys Ala Asp Val Asn Ser Met Ser Ile Asn
        195                 200                 205

Ile Gly Lys
    210

<210> SEQ ID NO 7
<211> LENGTH: 206
<212> TYPE: PRT
<213> ORGANISM: Clostridium stercorarium

<400> SEQUENCE: 7

Gly Arg Ile Ile Tyr Asp Asn Glu Thr Gly Thr His Gly Gly Tyr Asp
  1               5                  10                  15

Tyr Glu Leu Trp Lys Asp Tyr Gly Asn Thr Ile Met Glu Leu Asn Asp
             20                  25                  30

Gly Gly Thr Phe Ser Cys Gln Trp Ser Asn Ile Gly Asn Ala Leu Phe
         35                  40                  45

Arg Lys Gly Arg Lys Phe Asn Ser Asp Lys Thr Tyr Gln Glu Leu Gly
 50                  55                  60

Asp Ile Val Val Glu Tyr Gly Cys Asp Tyr Asn Pro Asn Gly Asn Ser
 65                  70                  75                  80

Tyr Leu Cys Val Tyr Gly Trp Thr Arg Asn Phe Leu Val Glu Tyr Tyr
             85                  90                  95

Ile Val Glu Ser Trp Gly Ser Trp Arg Pro Pro Gly Ala Thr Pro Lys
            100                 105                 110

Gly Thr Ile Thr Gln Trp Met Ala Gly Thr Tyr Glu Ile Tyr Glu Thr
            115                 120                 125

Thr Arg Val Asn Gln Pro Ser Ile Asp Gly Thr Ala Thr Phe Gln Gln
        130                 135                 140

Tyr Trp Ser Val Arg Thr Ser Lys Arg Thr Ser Gly Thr Ile Ser Val
145                 150                 155                 160

Thr Glu His Phe Lys Gln Trp Glu Arg Met Gly Met Arg Met Gly Lys
                165                 170                 175

Met Tyr Glu Val Ala Leu Thr Val Glu Gly Tyr Gln Ser Ser Gly Tyr
            180                 185                 190

Ala Asn Val Tyr Lys Asn Glu Ile Arg Ile Gly Ala Asn Pro
        195                 200                 205

<210> SEQ ID NO 8
<211> LENGTH: 211
<212> TYPE: PRT
```

-continued

<213> ORGANISM: Ruminococcus flavefaciens

<400> SEQUENCE: 8

```
Ser Ala Ala Asp Gln Gln Thr Arg Gly Asn Val Gly Gly Tyr Asp Tyr
  1               5                  10                  15

Glu Met Trp Asn Gln Asn Gly Gln Gly Gln Ala Ser Met Asn Pro Gly
             20                  25                  30

Ala Gly Ser Phe Thr Cys Ser Trp Ser Asn Ile Glu Asn Phe Leu Ala
         35                  40                  45

Arg Met Gly Lys Asn Tyr Asp Ser Gln Lys Lys Asn Tyr Lys Ala Phe
     50                  55                  60

Gly Asn Ile Val Leu Thr Tyr Asp Val Glu Tyr Thr Pro Arg Gly Asn
 65                  70                  75                  80

Ser Tyr Met Cys Val Tyr Gly Trp Thr Arg Asn Pro Leu Met Glu Tyr
                 85                  90                  95

Tyr Ile Val Glu Gly Trp Gly Asp Trp Arg Pro Pro Gly Asn Asp Gly
            100                 105                 110

Glu Val Lys Gly Thr Val Ser Ala Asn Gly Asn Thr Tyr Asp Ile Arg
        115                 120                 125

Lys Thr Met Arg Tyr Asn Gln Pro Ser Leu Asp Gly Thr Ala Thr Phe
    130                 135                 140

Pro Gln Tyr Trp Ser Val Arg Gln Thr Ser Gly Ser Ala Asn Asn Gln
145                 150                 155                 160

Thr Asn Tyr Met Lys Gly Thr Ile Asp Val Ser Lys His Phe Asp Ala
                165                 170                 175

Trp Ser Ala Ala Gly Leu Asp Met Ser Gly Thr Leu Tyr Glu Val Ser
            180                 185                 190

Leu Asn Ile Glu Gly Tyr Arg Ser Asn Gly Ser Ala Asn Val Lys Ser
        195                 200                 205

Val Ser Val
    210
```

<210> SEQ ID NO 9
<211> LENGTH: 197
<212> TYPE: PRT
<213> ORGANISM: Schizophyllum commune

<400> SEQUENCE: 9

```
Ser Gly Thr Pro Ser Ser Thr Gly Thr Asp Gly Gly Tyr Tyr Tyr Ser
  1               5                  10                  15

Trp Trp Thr Asp Gly Ala Gly Asp Ala Thr Tyr Gln Asn Asn Gly Gly
             20                  25                  30

Gly Ser Tyr Thr Leu Thr Trp Ser Gly Asn Asn Gly Asn Leu Val Gly
         35                  40                  45

Gly Lys Gly Trp Asn Pro Gly Ala Ala Ser Arg Ser Ile Ser Tyr Ser
     50                  55                  60

Gly Thr Tyr Gln Pro Asn Gly Asn Ser Tyr Leu Ser Val Tyr Gly Trp
 65                  70                  75                  80

Thr Arg Ser Ser Leu Ile Glu Tyr Tyr Ile Val Glu Ser Tyr Gly Ser
                 85                  90                  95

Tyr Asp Pro Ser Ser Ala Ala Ser His Lys Gly Ser Val Thr Cys Asn
            100                 105                 110

Gly Ala Thr Tyr Asp Ile Leu Ser Thr Trp Arg Tyr Asn Ala Pro Ser
        115                 120                 125

Ile Asp Gly Thr Gln Thr Phe Glu Gln Phe Trp Ser Val Arg Asn Pro
```

-continued

```
            130                 135                 140
Lys Lys Ala Pro Gly Gly Ser Ile Ser Gly Thr Val Asp Val Gln Cys
145                 150                 155                 160

His Phe Asp Ala Trp Lys Gly Leu Gly Met Asn Leu Gly Ser Glu His
                165                 170                 175

Asn Tyr Gln Ile Val Ala Thr Glu Gly Tyr Gln Ser Ser Gly Thr Ala
                180                 185                 190

Thr Ile Thr Val Thr
            195

<210> SEQ ID NO 10
<211> LENGTH: 191
<212> TYPE: PRT
<213> ORGANISM: Streptomyces lividans

<400> SEQUENCE: 10

Asp Thr Val Val Thr Thr Asn Gln Glu Gly Thr Asn Asn Gly Tyr Tyr
1               5                   10                  15

Tyr Ser Phe Trp Thr Asp Ser Gln Gly Thr Val Ser Met Asn Met Gly
                20                  25                  30

Ser Gly Gly Gln Tyr Ser Thr Ser Trp Arg Asn Thr Gly Asn Phe Val
            35                  40                  45

Ala Gly Lys Gly Trp Ala Asn Gly Gly Arg Arg Thr Val Gln Tyr Ser
        50                  55                  60

Gly Ser Phe Asn Pro Ser Gly Asn Ala Tyr Leu Ala Leu Tyr Gly Trp
65                  70                  75                  80

Thr Ser Asn Pro Leu Val Glu Tyr Tyr Ile Val Asp Asn Trp Gly Thr
                85                  90                  95

Tyr Arg Pro Thr Gly Glu Tyr Lys Gly Thr Val Thr Ser Asp Gly Gly
                100                 105                 110

Thr Tyr Asp Ile Tyr Lys Thr Thr Arg Val Asn Lys Pro Ser Val Glu
            115                 120                 125

Gly Thr Arg Thr Phe Asp Gln Tyr Trp Ser Val Arg Gln Ser Lys Arg
        130                 135                 140

Thr Gly Gly Thr Ile Thr Thr Gly Asn His Phe Asp Ala Trp Ala Arg
145                 150                 155                 160

Ala Gly Met Pro Leu Gly Asn Phe Ser Tyr Tyr Met Ile Asn Ala Thr
                165                 170                 175

Glu Gly Tyr Gln Ser Ser Gly Ser Ser Ile Asn Val Gly Gly
                180                 185                 190

<210> SEQ ID NO 11
<211> LENGTH: 191
<212> TYPE: PRT
<213> ORGANISM: Streptomyces lividans

<400> SEQUENCE: 11

Ala Thr Thr Ile Thr Thr Asn Gln Thr Gly Thr Asp Gly Met Tyr Tyr
1               5                   10                  15

Ser Phe Trp Thr Asp Gly Gly Ser Val Ser Met Thr Leu Asn Gly
                20                  25                  30

Gly Gly Ser Tyr Ser Thr Gln Trp Thr Asn Cys Gly Asn Phe Val Ala
            35                  40                  45

Gly Lys Gly Trp Ser Thr Gly Asp Gly Asn Val Arg Tyr Asn Gly Tyr
        50                  55                  60

Phe Asn Pro Val Gly Asn Gly Tyr Gly Cys Leu Tyr Gly Trp Thr Ser
```

```
                65                  70                  75                  80
Asn Pro Leu Val Glu Tyr Tyr Ile Val Asp Asn Trp Gly Ser Tyr Arg
                85                  90                  95

Pro Thr Gly Thr Tyr Lys Gly Thr Val Ser Ser Asp Gly Gly Thr Tyr
            100                 105                 110

Asp Ile Tyr Gln Thr Thr Arg Tyr Asn Ala Pro Ser Val Glu Gly Thr
            115                 120                 125

Lys Thr Phe Gln Gln Tyr Trp Ser Val Arg Gln Ser Lys Val Thr Ser
            130                 135                 140

Gly Ser Gly Thr Ile Thr Thr Gly Asn His Phe Asp Ala Trp Ala Arg
145                 150                 155                 160

Ala Gly Met Asn Met Gly Gln Phe Arg Tyr Tyr Met Ile Asn Ala Thr
                165                 170                 175

Glu Gly Tyr Gln Ser Ser Gly Ser Ser Asn Ile Thr Val Ser Gly
            180                 185                 190

<210> SEQ ID NO 12
<211> LENGTH: 189
<212> TYPE: PRT
<213> ORGANISM: Streptomyces sp.

<400> SEQUENCE: 12

Ala Thr Thr Ile Thr Asn Glu Thr Gly Tyr Asp Gly Met Tyr Tyr Ser
  1               5                  10                  15

Phe Trp Thr Asp Gly Gly Gly Ser Val Ser Met Thr Leu Asn Gly Gly
                20                  25                  30

Gly Ser Tyr Ser Thr Arg Trp Thr Asn Cys Gly Asn Phe Val Ala Gly
            35                  40                  45

Lys Gly Trp Ala Asn Gly Gly Arg Arg Thr Val Arg Tyr Thr Gly Trp
    50                  55                  60

Phe Asn Pro Ser Gly Asn Gly Tyr Gly Cys Leu Tyr Gly Trp Thr Ser
65                  70                  75                  80

Asn Pro Leu Val Glu Tyr Tyr Ile Val Asp Asn Trp Gly Ser Tyr Arg
                85                  90                  95

Pro Thr Gly Glu Thr Arg Gly Thr Val His Ser Asp Gly Gly Thr Tyr
            100                 105                 110

Asp Ile Tyr Lys Thr Thr Arg Tyr Asn Ala Pro Ser Val Glu Ala Pro
            115                 120                 125

Ala Ala Phe Asp Gln Tyr Trp Ser Val Arg Gln Ser Lys Val Thr Ser
            130                 135                 140

Gly Thr Ile Thr Thr Gly Asn His Phe Asp Ala Trp Ala Arg Ala Gly
145                 150                 155                 160

Met Asn Met Gly Asn Phe Arg Tyr Tyr Met Ile Asn Ala Thr Glu Gly
                165                 170                 175

Tyr Gln Ser Ser Gly Ser Ser Thr Ile Thr Val Ser Gly
            180                 185

<210> SEQ ID NO 13
<211> LENGTH: 189
<212> TYPE: PRT
<213> ORGANISM: Thermomonospora fusca

<400> SEQUENCE: 13

Ala Val Thr Ser Asn Glu Thr Gly Tyr His Asp Gly Tyr Phe Tyr Ser
  1               5                  10                  15

Phe Trp Thr Asp Ala Pro Gly Thr Val Ser Met Glu Leu Gly Pro Gly
```

-continued

```
                    20                  25                  30

Gly Asn Tyr Ser Thr Ser Trp Arg Asn Thr Gly Asn Phe Val Ala Gly
            35                  40                  45

Lys Gly Trp Ala Thr Gly Gly Arg Arg Thr Val Thr Tyr Ser Ala Ser
        50                  55                  60

Phe Asn Pro Ser Gly Asn Ala Tyr Leu Thr Leu Tyr Gly Trp Thr Arg
65                  70                  75                  80

Asn Pro Leu Val Glu Tyr Tyr Ile Val Glu Ser Trp Gly Thr Tyr Arg
                85                  90                  95

Pro Thr Gly Thr Tyr Met Gly Thr Val Thr Thr Asp Gly Gly Thr Tyr
            100                 105                 110

Asp Ile Tyr Lys Thr Thr Arg Tyr Asn Ala Pro Ser Ile Glu Gly Thr
        115                 120                 125

Arg Thr Phe Asp Gln Tyr Trp Ser Val Arg Gln Ser Lys Arg Thr Ser
130                 135                 140

Gly Thr Ile Thr Ala Gly Asn His Phe Asp Ala Trp Ala Arg His Gly
145                 150                 155                 160

Met His Leu Gly Thr His Asp Tyr Met Ile Met Ala Thr Glu Gly Tyr
                165                 170                 175

Gln Ser Ser Gly Ser Ser Asn Val Thr Leu Gly Thr Ser
            180                 185

<210> SEQ ID NO 14
<211> LENGTH: 190
<212> TYPE: PRT
<213> ORGANISM: Trichoderma harzianum

<400> SEQUENCE: 14

Gln Thr Ile Gly Pro Gly Thr Gly Tyr Ser Asn Gly Tyr Tyr Tyr Ser
1               5                   10                  15

Tyr Trp Asn Asp Gly His Ala Gly Val Thr Tyr Thr Asn Gly Gly Gly
                20                  25                  30

Gly Ser Phe Thr Val Asn Trp Ser Asn Ser Gly Asn Phe Val Gly Gly
            35                  40                  45

Lys Gly Trp Gln Pro Gly Thr Lys Asn Lys Val Ile Asn Phe Ser Gly
        50                  55                  60

Ser Tyr Asn Pro Asn Gly Asn Ser Tyr Leu Ser Ile Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
        115                 120                 125

Ile Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Ser His Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 15
<211> LENGTH: 178
```

<212> TYPE: PRT
<213> ORGANISM: Trichoderma reesei

<400> SEQUENCE: 15

```
Ala Ser Ile Asn Tyr Asp Gln Asn Tyr Gln Thr Gly Gly Gln Val Ser
 1               5                  10                  15

Tyr Ser Pro Ser Asn Thr Gly Phe Ser Val Asn Trp Asn Thr Gln Asp
                20                  25                  30

Asp Phe Val Val Gly Val Gly Trp Thr Thr Gly Ser Ser Ala Pro Ile
            35                  40                  45

Asn Phe Gly Gly Ser Phe Ser Val Asn Ser Gly Thr Gly Leu Leu Ser
        50                  55                  60

Val Tyr Gly Trp Ser Thr Asn Pro Leu Val Glu Tyr Tyr Ile Met Glu
65                  70                  75                  80

Asp Asn His Asn Tyr Pro Ala Gln Gly Thr Val Lys Gly Thr Val Thr
                85                  90                  95

Ser Asp Gly Ala Thr Tyr Thr Ile Trp Glu Asn Thr Arg Val Asn Glu
            100                 105                 110

Pro Ser Ile Gln Gly Thr Ala Thr Phe Asn Gln Tyr Ile Ser Val Arg
        115                 120                 125

Asn Ser Pro Arg Thr Ser Gly Thr Val Thr Val Gln Asn His Phe Asn
    130                 135                 140

Trp Ala Ser Leu Gly Leu His Leu Gly Gln Met Met Asn Tyr Gln Val
145                 150                 155                 160

Val Ala Val Glu Gly Trp Gly Gly Ser Gly Ser Ala Ser Gln Ser Val
                165                 170                 175

Ser Asn
```

<210> SEQ ID NO 16
<211> LENGTH: 190
<212> TYPE: PRT
<213> ORGANISM: Trichoderma reesei

<400> SEQUENCE: 16

```
Gln Thr Ile Gln Pro Gly Thr Gly Tyr Asn Asn Gly Tyr Phe Tyr Ser
 1               5                  10                  15

Tyr Trp Asn Asp Gly His Gly Gly Val Thr Tyr Thr Asn Gly Pro Gly
                20                  25                  30

Gly Gln Phe Ser Val Asn Trp Ser Asn Ser Gly Asn Phe Val Gly Gly
            35                  40                  45

Lys Gly Trp Gln Pro Gly Thr Lys Asn Lys Val Ile Asn Phe Ser Gly
        50                  55                  60

Ser Tyr Asn Pro Asn Gly Asn Ser Tyr Leu Ser Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
        115                 120                 125

Ile Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
```

```
                    165                 170                 175

Glu Gly Tyr Phe Ser Ser Gly Ser Ala Ser Ile Thr Val Ser
            180                 185                 190

<210> SEQ ID NO 17
<211> LENGTH: 190
<212> TYPE: PRT
<213> ORGANISM: Trichoderma viride

<400> SEQUENCE: 17

Gln Thr Ile Gln Pro Gly Thr Gly Phe Asn Asn Gly Tyr Phe Tyr Ser
  1               5                  10                  15

Tyr Trp Asn Asp Gly His Gly Gly Val Thr Tyr Thr Asn Gly Pro Gly
             20                  25                  30

Gly Gln Phe Ser Val Asn Trp Ser Asn Ser Gly Asn Phe Val Gly Gly
         35                  40                  45

Lys Gly Trp Gln Pro Gly Thr Lys Asn Lys Val Ile Asn Phe Ser Gly
     50                  55                  60

Ser Tyr Asn Pro Asn Gly Asn Ser Tyr Leu Ser Val Tyr Gly Trp Ser
 65                  70                  75                  80

Arg Asn Pro Leu Ile Glu Tyr Tyr Ile Val Glu Asn Phe Gly Thr Tyr
                 85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
        115                 120                 125

Ile Gly Thr Ala Thr Phe Tyr Gln Tyr Trp Ser Val Arg Arg Thr His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 18
<211> LENGTH: 202
<212> TYPE: PRT
<213> ORGANISM: Fibrobacter succinogenes

<400> SEQUENCE: 18

Asn Ser Ser Val Thr Gly Asn Val Gly Ser Ser Pro Tyr His Tyr Glu
  1               5                  10                  15

Ile Trp Tyr Gln Gly Gly Asn Asn Ser Met Thr Phe Tyr Asp Asn Gly
             20                  25                  30

Thr Tyr Lys Ala Ser Trp Asn Gly Thr Asn Asp Phe Leu Ala Arg Val
         35                  40                  45

Gly Phe Lys Tyr Asp Glu Lys His Thr Tyr Glu Glu Leu Gly Pro Ile
     50                  55                  60

Asp Ala Tyr Tyr Lys Trp Ser Lys Gln Gly Ser Ala Gly Gly Tyr Asn
 65                  70                  75                  80

Tyr Ile Gly Ile Tyr Gly Trp Thr Val Asp Pro Leu Val Glu Tyr Tyr
                 85                  90                  95

Ile Val Asp Asp Trp Phe Asn Lys Pro Gly Ala Asn Leu Leu Gly Gln
            100                 105                 110

Arg Lys Gly Glu Phe Thr Val Asp Gly Asp Thr Tyr Glu Ile Trp Gln
```

```
                115                 120                 125
Asn Thr Arg Val Gln Gln Pro Ser Ile Lys Gly Thr Gln Thr Phe Pro
    130                 135                 140

Gln Tyr Phe Ser Val Arg Lys Ser Ala Arg Ser Cys Gly His Ile Asp
145                 150                 155                 160

Ile Thr Ala His Met Lys Lys Trp Glu Glu Leu Gly Met Lys Met Gly
                165                 170                 175

Lys Met Tyr Glu Ala Lys Val Leu Val Glu Ala Gly Gly Ser Gly
            180                 185                 190

Ser Phe Asp Val Thr Tyr Phe Lys Met Thr
            195                 200

<210> SEQ ID NO 19
<211> LENGTH: 189
<212> TYPE: PRT
<213> ORGANISM: Aspergillus awamori

<400> SEQUENCE: 19

Arg Ser Thr Pro Ser Ser Thr Gly Glu Asn Asn Gly Tyr Tyr Tyr Ser
1               5                   10                  15

Phe Trp Thr Asp Gly Gly Gly Asp Val Thr Tyr Thr Asn Gly Asn Ala
            20                  25                  30

Gly Ser Tyr Ser Val Glu Trp Ser Asn Val Gly Asn Phe Val Gly Gly
        35                  40                  45

Lys Gly Trp Asn Pro Gly Ser Ala Lys Asp Ile Thr Tyr Ser Gly Asn
    50                  55                  60

Phe Thr Pro Ser Gly Asn Gly Tyr Leu Ser Val Tyr Gly Trp Thr Thr
65                  70                  75                  80

Asp Pro Leu Ile Glu Tyr Tyr Ile Val Glu Ser Tyr Gly Asp Tyr Asn
                85                  90                  95

Pro Gly Ser Gly Gly Thr Thr Arg Gly Asn Val Ser Ser Asp Gly Ser
            100                 105                 110

Val Tyr Asp Ile Tyr Thr Ala Thr Arg Thr Asn Ala Pro Ser Ile Asp
        115                 120                 125

Gly Thr Gln Thr Phe Ser Gln Tyr Trp Ser Val Arg Gln Asn Lys Arg
    130                 135                 140

Val Gly Gly Thr Val Thr Thr Ser Asn His Phe Asn Ala Trp Ala Lys
145                 150                 155                 160

Leu Gly Met Asn Leu Gly Thr His Asn Tyr Gln Ile Leu Ala Thr Glu
                165                 170                 175

Gly Tyr Gln Ser Ser Gly Ser Ser Ser Ile Thr Ile Gln
            180                 185

<210> SEQ ID NO 20
<211> LENGTH: 194
<212> TYPE: PRT
<213> ORGANISM: Thermomyces lanuginosus

<400> SEQUENCE: 20

Gln Thr Thr Pro Asn Ser Glu Gly Trp His Asp Gly Tyr Tyr Tyr Ser
1               5                   10                  15

Trp Trp Ser Asp Gly Gly Ala Gln Ala Thr Tyr Thr Asn Leu Glu Gly
            20                  25                  30

Gly Thr Tyr Glu Ile Ser Trp Gly Asp Gly Gly Asn Leu Val Gly Gly
        35                  40                  45

Lys Gly Trp Asn Pro Gly Leu Asn Ala Arg Ala Ile His Phe Glu Gly
```

-continued

```
            50                  55                  60
Val Tyr Gln Pro Asn Gly Asn Ser Tyr Leu Ala Val Tyr Gly Trp Thr
 65                  70                  75                  80

Arg Asn Pro Leu Val Glu Tyr Tyr Ile Val Glu Asn Phe Gly Thr Tyr
                 85                  90                  95

Asp Pro Ser Ser Gly Ala Thr Asp Leu Gly Thr Val Glu Cys Asp Gly
            100                 105                 110

Ser Ile Tyr Arg Leu Gly Lys Thr Thr Arg Val Asn Ala Pro Ser Ile
        115                 120                 125

Asp Gly Thr Gln Thr Phe Asp Gln Tyr Trp Ser Val Arg Gln Asp Lys
130                 135                 140

Arg Thr Ser Gly Thr Val Gln Thr Gly Cys His Phe Asp Ala Trp Ala
145                 150                 155                 160

Arg Ala Gly Leu Asn Val Asn Gly Asp His Tyr Tyr Gln Ile Val Ala
                165                 170                 175

Thr Glu Gly Tyr Phe Ser Ser Gly Tyr Ala Arg Ile Thr Val Ala Asp
            180                 185                 190

Val Gly
```

<210> SEQ ID NO 21
<211> LENGTH: 76
<212> TYPE: DNA
<213> ORGANISM: Artificial Sequence
<220> FEATURE:
<223> OTHER INFORMATION: Description of Artificial Sequence: TrX 1

<400> SEQUENCE: 21
ctagctaagg aggctgcaga tgcaaacaat acaaccagga accggttaca acaacggtta    60
cttttacagc tattgg                                                   76

<210> SEQ ID NO 22
<211> LENGTH: 78
<212> TYPE: DNA
<213> ORGANISM: Artificial Sequence
<220> FEATURE:
<223> OTHER INFORMATION: Description of Artificial Sequence: XyTv 2

<400> SEQUENCE: 22
aacgatggcc atggtggtgt tacctataca aacgggcccg gaggccaatt tagcgtcaat    60
tggtctaact ccggaaac                                                 78

<210> SEQ ID NO 23
<211> LENGTH: 78
<212> TYPE: DNA
<213> ORGANISM: Artificial Sequence
<220> FEATURE:
<223> OTHER INFORMATION: Description of Artificial Sequence: TrX 3

<400> SEQUENCE: 23
ttcgtaggtg gaaaaggttg gcaacccggg accaaaaata aggtgatcaa cttctctgga    60
tcttataatc cgaatggg                                                 78

<210> SEQ ID NO 24
<211> LENGTH: 74
<212> TYPE: DNA
<213> ORGANISM: Artificial Sequence
<220> FEATURE:
<223> OTHER INFORMATION: Description of Artificial Sequence: XyTv 4

<400> SEQUENCE: 24
aattcatact taagcgtcta tggctggtct agaaacccac tgattgaata ttacattgtc      60
gaaaatttcg gtac                                                       74

<210> SEQ ID NO 25
<211> LENGTH: 51
<212> TYPE: DNA
<213> ORGANISM: Artificial Sequence
<220> FEATURE:
<223> OTHER INFORMATION: Description of Artificial Sequence: TrX 8

<400> SEQUENCE: 25
gattcctccg acgtctacgt tgttatgtt ggtccttggc aatgttgtt g                51

<210> SEQ ID NO 26
<211> LENGTH: 84
<212> TYPE: DNA
<213> ORGANISM: Artificial Sequence
<220> FEATURE:
<223> OTHER INFORMATION: Description of Artificial Sequence: XyTv 7

<400> SEQUENCE: 26
ccaatgaaaa tgtcgataac cttgctaccg gtaccaccac aatggatatg tttgcccggg      60
cctccggtta aatcgcagtt aacc                                            84

<210> SEQ ID NO 27
<211> LENGTH: 78
<212> TYPE: DNA
<213> ORGANISM: Artificial Sequence
<220> FEATURE:
<223> OTHER INFORMATION: Description of Artificial Sequence: TrX 6

<400> SEQUENCE: 27
agattgaggc ctttgaagca tccacctttt ccaaccgttg ggccctggtt tttattccac      60
tagttgaaga gacctaga                                                   78

<210> SEQ ID NO 28
<211> LENGTH: 85
<212> TYPE: DNA
<213> ORGANISM: Artificial Sequence
<220> FEATURE:
<223> OTHER INFORMATION: Description of Artificial Sequence: XyTv 5

<400> SEQUENCE: 28
atattaggct taccettaag tatgaattcg cagataccga ccagatcttt gggtgactaa      60
cttataatgt aacagctttt aaagc                                           85

<210> SEQ ID NO 29
<211> LENGTH: 58
<212> TYPE: DNA
<213> ORGANISM: Artificial Sequence
<220> FEATURE:
<223> OTHER INFORMATION: Description of Artificial Sequence: XyTv 101

<400> SEQUENCE: 29
tcgacaattt cggtacctac aatccgagta ccggcgccac aaaattaggc gaagtcac       58

<210> SEQ ID NO 30
<211> LENGTH: 53
<212> TYPE: DNA
<213> ORGANISM: Artificial Sequence
<220> FEATURE:
<223> OTHER INFORMATION: Description of Artificial Sequence: XyTv 102

-continued

```
<400> SEQUENCE: 30
tagtgatgga tccgtatatg atatctaccg tacccaacgc gttaatcagc cat            53

<210> SEQ ID NO 31
<211> LENGTH: 59
<212> TYPE: DNA
<213> ORGANISM: Artificial Sequence
<220> FEATURE:
<223> OTHER INFORMATION: Description of Artificial Sequence: TrX 103

<400> SEQUENCE: 31
cgatcattgg aaccgccacc ttttatcagt actggagtgt tagacgtaat catcggagc     59

<210> SEQ ID NO 32
<211> LENGTH: 69
<212> TYPE: DNA
<213> ORGANISM: Artificial Sequence
<220> FEATURE:
<223> OTHER INFORMATION: Description of Artificial Sequence: XyTv 104

<400> SEQUENCE: 32
tccggttcgg ttaatactgc gaatcacttt aatgcatggg cacagcaagg gttaaccta     60 ggtacaatg                                                            69

<210> SEQ ID NO 33
<211> LENGTH: 67
<212> TYPE: DNA
<213> ORGANISM: Artificial Sequence
<220> FEATURE:
<223> OTHER INFORMATION: Description of Artificial Sequence: XyTv 105

<400> SEQUENCE: 33
gattatcaaa tcgtagcggt ggaaggctac ttctcgagtg gttccgctag tattacagtg    60
agctaaa                                                              67

<210> SEQ ID NO 34
<211> LENGTH: 73
<212> TYPE: DNA
<213> ORGANISM: Artificial Sequence
<220> FEATURE:
<223> OTHER INFORMATION: Description of Artificial Sequence: XyTv 110

<400> SEQUENCE: 34
gttaaagcca tggatgttag gctcatggcc gcggtgtttt aatccgcttc agtgatcact    60
acctaggcat ata                                                       73

<210> SEQ ID NO 35
<211> LENGTH: 54
<212> TYPE: DNA
<213> ORGANISM: Artificial Sequence
<220> FEATURE:
<223> OTHER INFORMATION: Description of Artificial Sequence: XyTv 109

<400> SEQUENCE: 35
ctatagatgg catgggttgc gcaattagtc ggtagctagt aaccttggcg gtgg          54

<210> SEQ ID NO 36
<211> LENGTH: 60
<212> TYPE: DNA
<213> ORGANISM: Artificial Sequence
<220> FEATURE:
<223> OTHER INFORMATION: Description of Artificial Sequence: XyTv 108

<400> SEQUENCE: 36
```
aaaatagtca tgacctcaca atctgcatta gtagcctcga ggccaagcca attatgacgc    60

<210> SEQ ID NO 37
<211> LENGTH: 66
<212> TYPE: DNA
<213> ORGANISM: Artificial Sequence
<220> FEATURE:
<223> OTHER INFORMATION: Description of Artificial Sequence: XyTv 107

<400> SEQUENCE: 37
ttagtgaaat tacgtacccg tgtcgttccc aattgggatc catgttacct aatagtttag    60
catcgc                                                                66

<210> SEQ ID NO 38
<211> LENGTH: 53
<212> TYPE: DNA
<213> ORGANISM: Artificial Sequence
<220> FEATURE:
<223> OTHER INFORMATION: Description of Artificial Sequence: XyTv 106

<400> SEQUENCE: 38
caccttccga tgaagagctc accaaggcga tcataatgtc actcgatttc tag            53

<210> SEQ ID NO 39
<211> LENGTH: 596
<212> TYPE: DNA
<213> ORGANISM: Artificial Sequence
<220> FEATURE:
<223> OTHER INFORMATION: Description of Artificial Sequence: TrX

<400> SEQUENCE: 39
ctagctaagg aggctgcaga tgcaaacaat acaaccagga accggttaca acaacggtta    60
cttttacagc tattggaacg atggccatgg tggtgttacc tatacaaacg ggcccggagg   120
ccaatttagc gtcaattggt ctaactccgg aaacttcgta ggtggaaaag gttggcaacc   180
cgggaccaaa aataaggtga tcaacttctc tggatcttat aatccgaatg ggaattcata   240
cttaagcgtc tatggctggt ctagaaaccc actgattgaa tattcattg tcgaaaattt    300 cggtacctac aatccgagta ccggcgccac aaaattaggc gaagtcacta gtgatggatc   360
cgtatatgat atctaccgta cccaacgcgt taatcagcca tcgatcattg gaaccgccac   420
cttttatcag tactggagtg ttagacgtaa tcatcggagc tccggttcgg ttaatactgc   480
gaatcacttt aatgcatggg cacagcaagg gttaaccccta ggtacaatgg attatcaaat   540
cgtagcggtg gaaggctact ctcgagtgg ttccgctagt attacagtga gctaaa        596

<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence: Tx 75a 1

<400> SEQUENCE: 40
tgggaattca tacttagccg tctatggctg gtctag                                36

<210> SEQ ID NO 41
<211> LENGTH: 42
<212> TYPE: DNA
<213> ORGANISM: Artificial Sequence
<220> FEATURE:
<223> OTHER INFORMATION: Description of Artificial Sequence: Tx 105H 1

-continued

```
<400> SEQUENCE: 41
accggcgcca caaacacgg cgaagtcact agtgatggat cc                    42

<210> SEQ ID NO 42
<211> LENGTH: 44
<212> TYPE: DNA
<213> ORGANISM: Artificial Sequence
<220> FEATURE:
<223> OTHER INFORMATION: Description of Artificial Sequence: Tx C1

<400> SEQUENCE: 42
ccaaggcgat cataatgtca ctcgatttct agaacttcga accc                 44

<210> SEQ ID NO 43
<211> LENGTH: 42
<212> TYPE: DNA
<213> ORGANISM: Artificial Sequence
<220> FEATURE:
<223> OTHER INFORMATION: Description of Artificial Sequence: Tx 105K 1

<400> SEQUENCE: 43
accggcgcca caaaaaaagg cgaagtcact agtgatggat cc                   42

<210> SEQ ID NO 44
<211> LENGTH: 42
<212> TYPE: DNA
<213> ORGANISM: Artificial Sequence
<220> FEATURE:
<223> OTHER INFORMATION: Description of Artificial Sequence: Tx 105R 1

<400> SEQUENCE: 44
accggcgcca caaaaagagg cgaagtcact agtgatggat cc                   42

<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence: Tx 75C 1

<400> SEQUENCE: 45
tgggaattca tacttatgcg tctatggctg gtctag                          36

<210> SEQ ID NO 46
<211> LENGTH: 36
<212> TYPE: DNA
<213> ORGANISM: Artificial Sequence
<220> FEATURE:
<223> OTHER INFORMATION: Description of Artificial Sequence: Tx 75G 1

<400> SEQUENCE: 46
tgggaattca tacttaggcg tctatggctg gtctag                          36

<210> SEQ ID NO 47
<211> LENGTH: 36
<212> TYPE: DNA
<213> ORGANISM: Artificial Sequence
<220> FEATURE:
<223> OTHER INFORMATION: Description of Artificial Sequence: Tx 75T 1

<400> SEQUENCE: 47
tgggaattca tacttaaccg tctatggctg gtctag                          36

<210> SEQ ID NO 48
<211> LENGTH: 40
```

```
<212> TYPE: DNA
<213> ORGANISM: Artificial Sequence
<220> FEATURE:
<223> OTHER INFORMATION: Description of Artificial Sequence: TX 125A 1

<400> SEQUENCE: 48
ccaacgcgtt aatgcgccat cgatcattgg aaccgccacc                              40

<210> SEQ ID NO 49
<211> LENGTH: 40
<212> TYPE: DNA
<213> ORGANISM: Artificial Sequence
<220> FEATURE:
<223> OTHER INFORMATION: Description of Artificial Sequence: TX 125A
      129E 1

<400> SEQUENCE: 49
ccaacgcgtt aatgcgccat cgatcgaggg aaccgccacc                              40

<210> SEQ ID NO 50
<211> LENGTH: 38
<212> TYPE: DNA
<213> ORGANISM: Artificial Sequence
<220> FEATURE:
<223> OTHER INFORMATION: Description of Artificial Sequence: TX 104P
      105H 1

<400> SEQUENCE: 50
accggcgcca caccacacgg cgaagtcact agtgatgg                                38

<210> SEQ ID NO 51
<211> LENGTH: 38
<212> TYPE: DNA
<213> ORGANISM: Artificial Sequence
<220> FEATURE:
<223> OTHER INFORMATION: Description of Artificial Sequence: TX 104P
      105R 1

<400> SEQUENCE: 51
accggcgcca caccaagagg cgaagtcact agtgatgg                                38

<210> SEQ ID NO 52
<211> LENGTH: 112
<212> TYPE: DNA
<213> ORGANISM: Artificial Sequence
<220> FEATURE:
<223> OTHER INFORMATION: Description of Artificial Sequence: TrX-HML

<400> SEQUENCE: 52
ctagctaagg aggctgcaga tgcaaacaat acaaccagga accggttacc acaacggtta        60
cttttacagc tattggaacg atggccatgg aggcgtcaca atgactctgg gg               112

<210> SEQ ID NO 53
<211> LENGTH: 108
<212> TYPE: DNA
<213> ORGANISM: Artificial Sequence
<220> FEATURE:
<223> OTHER INFORMATION: Description of Artificial Sequence: TrX-HML
      (complementary)

<400> SEQUENCE: 53
gattcctccg acgtctacgt tgttatgtt ggtccttggc caatggtgtt gccaatgaaa        60
atgtcgataa ccttgctacc ggtacctccg cagtgttact gagacccc                   108

<210> SEQ ID NO 54
```

```
<211> LENGTH: 306
<212> TYPE: DNA
<213> ORGANISM: Artificial Sequence
<220> FEATURE:
<223> OTHER INFORMATION: Description of Artificial Sequence: TrX(1-91)

<400> SEQUENCE: 54
ctagctaagg aggctgcaga tgcaaacaat acaaccagga accggttaca acaacggtta      60
cttttacagc tattggaacg atggccatgg tggtgttacc tatacaaacg ggcccggagg     120
ccaatttagc gtcaattggt ctaactccgg aaacttcgta ggtggaaaag gttggcaacc     180
cgggaccaaa aataaggtga tcaacttctc tggatcttat aatccgaatg ggaattcata     240
cttaagcgtc tatggctggt ctagaaaccc actgattgaa tattacattg tcgaaaattt     300
cggtac                                                                306

<210> SEQ ID NO 55
<211> LENGTH: 298
<212> TYPE: DNA
<213> ORGANISM: Artificial Sequence
<220> FEATURE:
<223> OTHER INFORMATION: Description of Artificial Sequence: TrX(1-91)
      (complementary)

<400> SEQUENCE: 55
gattcctccg acgtctacgt tgttatgtt ggtccttggc caatgttgtt gccaatgaaa       60
atgtcgataa ccttgctacc ggtaccacca caatggatat gtttgcccgg gcctccggtt     120
aaatcgcagt taaccagatt gaggcctttg aagcatccac cttttccaac cgttgggccc     180
tggtttttat tccactagtt gaagagacct agaatattag cttacccctt aagtatgaat     240
tcgcagatac cgaccagatc tttgggtgac taacttataa tgtaacagct tttaaagc       298

<210> SEQ ID NO 56
<211> LENGTH: 290
<212> TYPE: DNA
<213> ORGANISM: Artificial Sequence
<220> FEATURE:
<223> OTHER INFORMATION: Description of Artificial Sequence: TrX(92-190)

<400> SEQUENCE: 56
ctacaatccg agtaccggcg ccacaaaatt aggcgaagtc actagtgatg gatccgtata      60
tgatatctac cgtacccaac gcgttaatca gccatcgatc attggaaccg ccacctttta    120
tcagtactgg agtgttagac gtaatcatcg gagctccggt tcggttaata ctgcgaatca    180
ctttaatgca tgggcacagc aagggttaac cctaggtaca atggattatc aaatcgtagc    240
ggtggaaggc tacttctcga gtggttccgc tagtattaca gtgagctaaa                290

<210> SEQ ID NO 57
<211> LENGTH: 306
<212> TYPE: DNA
<213> ORGANISM: Artificial Sequence
<220> FEATURE:
<223> OTHER INFORMATION: Description of Artificial Sequence: TrX(92-190)
      (complementary)

<400> SEQUENCE: 57
gttaaagcca tggatgttag gctcatggcc gcggtgtttt aatccgcttc agtgatcact      60
acctaggcat atactataga tggcatgggt tgcgcaatta gtcggtagct agtaaccttg    120
gcggtggaaa atagtcatga cctcacaatc tgcattagta gcctcgaggc caagccaatt    180
atgacgctta gtgaaattac gtacccgtgt cgttcccaat gggatccat gttacctaat     240
```

```
agtttagcat cgccaccttc cgatgaagag ctcaccaagg cgatcataat gtcactcgat    300
ttctag                                                              306
```

<210> SEQ ID NO 58
<211> LENGTH: 30
<212> TYPE: PRT
<213> ORGANISM: Artificial Sequence
<220> FEATURE:
<223> OTHER INFORMATION: Description of Artificial Sequence: First
      thirty amino acids of TrX-HML

<400> SEQUENCE: 58

Gln Thr Ile Gln Pro Gly Thr Gly Tyr His Asn Gly Tyr Phe Tyr Ser
 1               5                  10                  15

Tyr Trp Asn Asp Gly His Gly Gly Val Thr Met Thr Leu Gly
             20                  25                  30

<210> SEQ ID NO 59
<211> LENGTH: 190
<212> TYPE: PRT
<213> ORGANISM: Artificial Sequence
<220> FEATURE:
<223> OTHER INFORMATION: Description of Artificial Sequence: TrX-75A

<400> SEQUENCE: 59

Gln Thr Ile Gln Pro Gly Thr Gly Tyr Asn Asn Gly Tyr Phe Tyr Ser
 1               5                  10                  15

Tyr Trp Asn Asp Gly His Gly Gly Val Thr Tyr Thr Asn Gly Pro Gly
             20                  25                  30

Gly Gln Phe Ser Val Asn Trp Ser Asn Ser Gly Asn Phe Val Gly Gly
         35                  40                  45

Lys Gly Trp Gln Pro Gly Thr Lys Asn Lys Val Ile Asn Phe Ser Gly
     50                  55                  60

Ser Tyr Asn Pro Asn Gly Asn Ser Tyr Leu Ala Val Tyr Gly Trp Ser
 65                  70                  75                  80

Arg Asn Pro Leu Ile Glu Tyr Tyr Ile Val Glu Asn Phe Gly Thr Tyr
                 85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
        115                 120                 125

Ile Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 60
<211> LENGTH: 190
<212> TYPE: PRT
<213> ORGANISM: Artificial Sequence
<220> FEATURE:
<223> OTHER INFORMATION: Description of Artificial Sequence: TrX-105H

<400> SEQUENCE: 60

Gln Thr Ile Gln Pro Gly Thr Gly Tyr Asn Asn Gly Tyr Phe Tyr Ser

```
                1               5                   10                  15
Tyr Trp Asn Asp Gly His Gly Gly Val Thr Tyr Thr Asn Gly Pro Gly
                20                  25                  30

Gly Gln Phe Ser Val Asn Trp Ser Asn Ser Gly Asn Phe Val Gly Gly
            35                  40                  45

Lys Gly Trp Gln Pro Gly Thr Lys Asn Lys Val Ile Asn Phe Ser Gly
        50                  55                  60

Ser Tyr Asn Pro Asn Gly Asn Ser Tyr Leu Ser Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys His Gly Glu Val Thr Ser Asp Gly
            100                 105                 110

Ser Val Tyr Asp Ile Tyr Arg Thr Gln Arg Val Asn Gln Pro Ser Ile
            115                 120                 125

Ile Gly Thr Ala Thr Phe Tyr Gln Tyr Trp Ser Val Arg Arg Asn His
        130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 61
<211> LENGTH: 190
<212> TYPE: PRT
<213> ORGANISM: Artificial Sequence
<220> FEATURE:
<223> OTHER INFORMATION: Description of Artificial Sequence: TrX-HML

<400> SEQUENCE: 61

Gln Thr Ile Gln Pro Gly Thr Gly Tyr His Asn Gly Tyr Phe Tyr Ser
1               5                   10                  15

Tyr Trp Asn Asp Gly His Gly Gly Val Thr Met Thr Leu Gly Pro Gly
                20                  25                  30

Gly Gln Phe Ser Val Asn Trp Ser Asn Ser Gly Asn Phe Val Gly Gly
            35                  40                  45

Lys Gly Trp Gln Pro Gly Thr Lys Asn Lys Val Ile Asn Phe Ser Gly
        50                  55                  60

Ser Tyr Asn Pro Asn Gly Asn Ser Tyr Leu Ser Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
            115                 120                 125

Ile Gly Thr Ala Thr Phe Tyr Gln Tyr Trp Ser Val Arg Arg Asn His
        130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
```

-continued

```
                180                 185                 190

<210> SEQ ID NO 62
<211> LENGTH: 190
<212> TYPE: PRT
<213> ORGANISM: Artificial Sequence
<220> FEATURE:
<223> OTHER INFORMATION: Description of Artificial Sequence: TrX-HML-75A

<400> SEQUENCE: 62

Gln Thr Ile Gln Pro Gly Thr Gly Tyr His Asn Gly Tyr Phe Tyr Ser
  1               5                  10                  15

Tyr Trp Asn Asp Gly His Gly Gly Val Thr Met Thr Leu Gly Pro Gly
             20                  25                  30

Gly Gln Phe Ser Val Asn Trp Ser Asn Ser Gly Asn Phe Val Gly Gly
         35                  40                  45

Lys Gly Trp Gln Pro Gly Thr Lys Asn Lys Val Ile Asn Phe Ser Gly
     50                  55                  60

Ser Tyr Asn Pro Asn Gly Asn Ser Tyr Leu Ala Val Tyr Gly Trp Ser
 65                  70                  75                  80

Arg Asn Pro Leu Ile Glu Tyr Tyr Ile Val Glu Asn Phe Gly Thr Tyr
                 85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
        115                 120                 125

Ile Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 63
<211> LENGTH: 190
<212> TYPE: PRT
<213> ORGANISM: Artificial Sequence
<220> FEATURE:
<223> OTHER INFORMATION: Description of Artificial Sequence:
      TrX-HML-75A-105H

<400> SEQUENCE: 63

Gln Thr Ile Gln Pro Gly Thr Gly Tyr His Asn Gly Tyr Phe Tyr Ser
  1               5                  10                  15

Tyr Trp Asn Asp Gly His Gly Gly Val Thr Met Thr Leu Gly Pro Gly
             20                  25                  30

Gly Gln Phe Ser Val Asn Trp Ser Asn Ser Gly Asn Phe Val Gly Gly
         35                  40                  45

Lys Gly Trp Gln Pro Gly Thr Lys Asn Lys Val Ile Asn Phe Ser Gly
     50                  55                  60

Ser Tyr Asn Pro Asn Gly Asn Ser Tyr Leu Ala Val Tyr Gly Trp Ser
 65                  70                  75                  80

Arg Asn Pro Leu Ile Glu Tyr Tyr Ile Val Glu Asn Phe Gly Thr Tyr
                 85                  90                  95

Asn Pro Ser Thr Gly Ala Thr Lys His Gly Glu Val Thr Ser Asp Gly
            100                 105                 110
```

```
Ser Val Tyr Asp Ile Tyr Arg Thr Gln Arg Val Asn Gln Pro Ser Ile
            115                 120                 125

Ile Gly Thr Ala Thr Phe Tyr Gln Tyr Trp Ser Val Arg Arg Asn His
        130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 64
<211> LENGTH: 190
<212> TYPE: PRT
<213> ORGANISM: Artificial Sequence
<220> FEATURE:
<223> OTHER INFORMATION: Description of Artificial Sequence:
      TrX-HML-75A-105R

<400> SEQUENCE: 64

Gln Thr Ile Gln Pro Gly Thr Gly Tyr His Asn Gly Tyr Phe Tyr Ser
 1               5                  10                  15

Tyr Trp Asn Asp Gly His Gly Gly Val Thr Met Thr Leu Gly Pro Gly
            20                  25                  30

Gly Gln Phe Ser Val Asn Trp Ser Asn Ser Gly Asn Phe Val Gly Gly
        35                  40                  45

Lys Gly Trp Gln Pro Gly Thr Lys Asn Lys Val Ile Asn Phe Ser Gly
    50                  55                  60

Ser Tyr Asn Pro Asn Gly Asn Ser Tyr Leu Ala Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Arg Gly Glu Val Thr Ser Asp Gly
            100                 105                 110

Ser Val Tyr Asp Ile Tyr Arg Thr Gln Arg Val Asn Gln Pro Ser Ile
            115                 120                 125

Ile Gly Thr Ala Thr Phe Tyr Gln Tyr Trp Ser Val Arg Arg Asn His
        130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 65
<211> LENGTH: 190
<212> TYPE: PRT
<213> ORGANISM: Artificial Sequence
<220> FEATURE:
<223> OTHER INFORMATION: Description of Artificial Sequence:
      TrX-HML-75C-105R

<400> SEQUENCE: 65

Gln Thr Ile Gln Pro Gly Thr Gly Tyr His Asn Gly Tyr Phe Tyr Ser
 1               5                  10                  15

Tyr Trp Asn Asp Gly His Gly Gly Val Thr Met Thr Leu Gly Pro Gly
            20                  25                  30
```

Gly Gln Phe Ser Val Asn Trp Ser Asn Ser Gly Asn Phe Val Gly Gly
                35                  40                  45

Lys Gly Trp Gln Pro Gly Thr Lys Asn Lys Val Ile Asn Phe Ser Gly
     50                  55                  60

Ser Tyr Asn Pro Asn Gly Asn Ser Tyr Leu Cys Val Tyr Gly Trp Ser
 65                  70                  75                  80

Arg Asn Pro Leu Ile Glu Tyr Tyr Ile Val Glu Asn Phe Gly Thr Tyr
                 85                  90                  95

Asn Pro Ser Thr Gly Ala Thr Lys Arg Gly Glu Val Thr Ser Asp Gly
             100                 105                 110

Ser Val Tyr Asp Ile Tyr Arg Thr Gln Arg Val Asn Gln Pro Ser Ile
             115                 120                 125

Ile Gly Thr Ala Thr Phe Tyr Gln Tyr Trp Ser Val Arg Arg Asn His
             130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
                180                 185                 190

<210> SEQ ID NO 66
<211> LENGTH: 190
<212> TYPE: PRT
<213> ORGANISM: Artificial Sequence
<220> FEATURE:
<223> OTHER INFORMATION: Description of Artificial Sequence:
      TrX-HML-75G-105R

<400> SEQUENCE: 66

Gln Thr Ile Gln Pro Gly Thr Gly Tyr His Asn Gly Tyr Phe Tyr Ser
 1               5                  10                  15

Tyr Trp Asn Asp Gly His Gly Gly Val Thr Met Thr Leu Gly Pro Gly
                 20                  25                  30

Gly Gln Phe Ser Val Asn Trp Ser Asn Ser Gly Asn Phe Val Gly Gly
                35                  40                  45

Lys Gly Trp Gln Pro Gly Thr Lys Asn Lys Val Ile Asn Phe Ser Gly
     50                  55                  60

Ser Tyr Asn Pro Asn Gly Asn Ser Tyr Leu Gly Val Tyr Gly Trp Ser
 65                  70                  75                  80

Arg Asn Pro Leu Ile Glu Tyr Tyr Ile Val Glu Asn Phe Gly Thr Tyr
                 85                  90                  95

Asn Pro Ser Thr Gly Ala Thr Lys Arg Gly Glu Val Thr Ser Asp Gly
             100                 105                 110

Ser Val Tyr Asp Ile Tyr Arg Thr Gln Arg Val Asn Gln Pro Ser Ile
             115                 120                 125

Ile Gly Thr Ala Thr Phe Tyr Gln Tyr Trp Ser Val Arg Arg Asn His
             130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
                180                 185                 190

<210> SEQ ID NO 67
<211> LENGTH: 190
<212> TYPE: PRT
<213> ORGANISM: Artificial Sequence
<220> FEATURE:
<223> OTHER INFORMATION: Description of Artificial Sequence:
    TrX-HML-75T-105R

<400> SEQUENCE: 67

Gln Thr Ile Gln Pro Gly Thr Gly Tyr His Asn Gly Tyr Phe Tyr Ser
1               5                   10                  15

Tyr Trp Asn Asp Gly His Gly Gly Val Thr Met Thr Leu Gly Pro Gly
                20                  25                  30

Gly Gln Phe Ser Val Asn Trp Ser Asn Ser Gly Asn Phe Val Gly Gly
            35                  40                  45

Lys Gly Trp Gln Pro Gly Thr Lys Asn Lys Val Ile Asn Phe Ser Gly
    50                  55                  60

Ser Tyr Asn Pro Asn Gly Asn Ser Tyr Leu Thr Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Arg Gly Glu Val Thr Ser Asp Gly
            100                 105                 110

Ser Val Tyr Asp Ile Tyr Arg Thr Gln Arg Val Asn Gln Pro Ser Ile
        115                 120                 125

Ile Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 68
<211> LENGTH: 190
<212> TYPE: PRT
<213> ORGANISM: Artificial Sequence
<220> FEATURE:
<223> OTHER INFORMATION: Description of Artificial Sequence:
    TrX-HML-GRAE

<400> SEQUENCE: 68

Gln Thr Ile Gln Pro Gly Thr Gly Tyr His Asn Gly Tyr Phe Tyr Ser
1               5                   10                  15

Tyr Trp Asn Asp Gly His Gly Gly Val Thr Met Thr Leu Gly Pro Gly
                20                  25                  30

Gly Gln Phe Ser Val Asn Trp Ser Asn Ser Gly Asn Phe Val Gly Gly
            35                  40                  45

Lys Gly Trp Gln Pro Gly Thr Lys Asn Lys Val Ile Asn Phe Ser Gly
    50                  55                  60

Ser Tyr Asn Pro Asn Gly Asn Ser Tyr Leu Gly Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Arg Gly Glu Val Thr Ser Asp Gly
            100                 105                 110

Ser Val Tyr Asp Ile Tyr Arg Thr Gln Arg Val Asn Ala Pro Ser Ile

```
              115                 120                 125

Glu Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 69
<211> LENGTH: 190
<212> TYPE: PRT
<213> ORGANISM: Artificial Sequence
<220> FEATURE:
<223> OTHER INFORMATION: Description of Artificial Sequence:
      TrX-HML-AHAE

<400> SEQUENCE: 69

Gln Thr Ile Gln Pro Gly Thr Gly Tyr His Asn Gly Tyr Phe Tyr Ser
  1               5                  10                  15

Tyr Trp Asn Asp Gly His Gly Gly Val Thr Met Thr Leu Gly Pro Gly
                 20                  25                  30

Gly Gln Phe Ser Val Asn Trp Ser Asn Ser Gly Asn Phe Val Gly Gly
             35                  40                  45

Lys Gly Trp Gln Pro Gly Thr Lys Asn Lys Val Ile Asn Phe Ser Gly
 50                  55                  60

Ser Tyr Asn Pro Asn Gly Asn Ser Tyr Leu Ala Val Tyr Gly Trp Ser
 65                  70                  75                  80

Arg Asn Pro Leu Ile Glu Tyr Tyr Ile Val Glu Asn Phe Gly Thr Tyr
                 85                  90                  95

Asn Pro Ser Thr Gly Ala Thr Lys His Gly Glu Val Thr Ser Asp Gly
            100                 105                 110

Ser Val Tyr Asp Ile Tyr Arg Thr Gln Arg Val Asn Ala Pro Ser Ile
        115                 120                 125

Glu Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 70
<211> LENGTH: 190
<212> TYPE: PRT
<213> ORGANISM: Artificial Sequence
<220> FEATURE:
<223> OTHER INFORMATION: Description of Artificial Sequence:
      TrX-HML-GHAE

<400> SEQUENCE: 70

Gln Thr Ile Gln Pro Gly Thr Gly Tyr His Asn Gly Tyr Phe Tyr Ser
  1               5                  10                  15

Tyr Trp Asn Asp Gly His Gly Gly Val Thr Met Thr Leu Gly Pro Gly
                 20                  25                  30

Gly Gln Phe Ser Val Asn Trp Ser Asn Ser Gly Asn Phe Val Gly Gly
```

-continued

```
                35                  40                  45
Lys Gly Trp Gln Pro Gly Thr Lys Asn Lys Val Ile Asn Phe Ser Gly
         50                  55                  60

Ser Tyr Asn Pro Asn Gly Asn Ser Tyr Leu Gly Val Tyr Gly Trp Ser
 65                  70                  75                  80

Arg Asn Pro Leu Ile Glu Tyr Tyr Ile Val Glu Asn Phe Gly Thr Tyr
                 85                  90                  95

Asn Pro Ser Thr Gly Ala Thr Lys His Gly Glu Val Thr Ser Asp Gly
                100                 105                 110

Ser Val Tyr Asp Ile Tyr Arg Thr Gln Arg Val Asn Ala Pro Ser Ile
            115                 120                 125

Glu Gly Thr Ala Thr Phe Tyr Gln Tyr Trp Ser Val Arg Arg Asn His
        130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 71
<211> LENGTH: 190
<212> TYPE: PRT
<213> ORGANISM: Artificial Sequence
<220> FEATURE:
<223> OTHER INFORMATION: Description of Artificial Sequence:
      TrX-HML-ARAE

<400> SEQUENCE: 71

Gln Thr Ile Gln Pro Gly Thr Gly Tyr His Asn Gly Tyr Phe Tyr Ser
 1               5                  10                  15

Tyr Trp Asn Asp Gly His Gly Gly Val Thr Met Thr Leu Gly Pro Gly
                20                  25                  30

Gly Gln Phe Ser Val Asn Trp Ser Asn Ser Gly Asn Phe Val Gly Gly
            35                  40                  45

Lys Gly Trp Gln Pro Gly Thr Lys Asn Lys Val Ile Asn Phe Ser Gly
         50                  55                  60

Ser Tyr Asn Pro Asn Gly Asn Ser Tyr Leu Ala Val Tyr Gly Trp Ser
 65                  70                  75                  80

Arg Asn Pro Leu Ile Glu Tyr Tyr Ile Val Glu Asn Phe Gly Thr Tyr
                 85                  90                  95

Asn Pro Ser Thr Gly Ala Thr Lys Arg Gly Glu Val Thr Ser Asp Gly
                100                 105                 110

Ser Val Tyr Asp Ile Tyr Arg Thr Gln Arg Val Asn Ala Pro Ser Ile
            115                 120                 125

Glu Gly Thr Ala Thr Phe Tyr Gln Tyr Trp Ser Val Arg Arg Asn His
        130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 72
<211> LENGTH: 190
```

<212> TYPE: PRT
<213> ORGANISM: Artificial Sequence
<220> FEATURE:
<223> OTHER INFORMATION: Description of Artificial Sequence:
    TrX-HML-GPRAE

<400> SEQUENCE: 72

```
Gln Thr Ile Gln Pro Gly Thr Gly Tyr His Asn Gly Tyr Phe Tyr Ser
 1               5                  10                  15

Tyr Trp Asn Asp Gly His Gly Gly Val Thr Met Thr Leu Gly Pro Gly
             20                  25                  30

Gly Gln Phe Ser Val Asn Trp Ser Asn Ser Gly Asn Phe Val Gly Gly
         35                  40                  45

Lys Gly Trp Gln Pro Gly Thr Lys Asn Lys Val Ile Asn Phe Ser Gly
     50                  55                  60

Ser Tyr Asn Pro Asn Gly Asn Ser Tyr Leu Gly Val Tyr Gly Trp Ser
 65                  70                  75                  80

Arg Asn Pro Leu Ile Glu Tyr Tyr Ile Val Glu Asn Phe Gly Thr Tyr
                 85                  90                  95

Asn Pro Ser Thr Gly Ala Thr Pro Arg Gly Glu Val Thr Ser Asp Gly
            100                 105                 110

Ser Val Tyr Asp Ile Tyr Arg Thr Gln Arg Val Asn Ala Pro Ser Ile
        115                 120                 125

Glu Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190
```

<210> SEQ ID NO 73
<211> LENGTH: 190
<212> TYPE: PRT
<213> ORGANISM: Artificial Sequence
<220> FEATURE:
<223> OTHER INFORMATION: Description of Artificial Sequence:
    TrX-HML-GPHAE

<400> SEQUENCE: 73

```
Gln Thr Ile Gln Pro Gly Thr Gly Tyr His Asn Gly Tyr Phe Tyr Ser
 1               5                  10                  15

Tyr Trp Asn Asp Gly His Gly Gly Val Thr Met Thr Leu Gly Pro Gly
             20                  25                  30

Gly Gln Phe Ser Val Asn Trp Ser Asn Ser Gly Asn Phe Val Gly Gly
         35                  40                  45

Lys Gly Trp Gln Pro Gly Thr Lys Asn Lys Val Ile Asn Phe Ser Gly
     50                  55                  60

Ser Tyr Asn Pro Asn Gly Asn Ser Tyr Leu Gly Val Tyr Gly Trp Ser
 65                  70                  75                  80

Arg Asn Pro Leu Ile Glu Tyr Tyr Ile Val Glu Asn Phe Gly Thr Tyr
                 85                  90                  95

Asn Pro Ser Thr Gly Ala Thr Pro His Gly Glu Val Thr Ser Asp Gly
            100                 105                 110

Ser Val Tyr Asp Ile Tyr Arg Thr Gln Arg Val Asn Ala Pro Ser Ile
        115                 120                 125
```

Glu Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                    165                 170                 175

Glu Gly Tyr Phe Ser Ser Gly Ser Ala Ser Ile Thr Val Ser
                180                 185                 190

<210> SEQ ID NO 74
<211> LENGTH: 190
<212> TYPE: PRT
<213> ORGANISM: Artificial Sequence
<220> FEATURE:
<223> OTHER INFORMATION: Description of Artificial Sequence:
      TrX-HML-AHAE-RR

<400> SEQUENCE: 74

Gln Thr Ile Gln Pro Gly Thr Gly Tyr His Asn Gly Tyr Phe Tyr Ser
  1               5                  10                  15

Tyr Trp Asn Asp Gly His Gly Gly Val Thr Met Thr Leu Gly Pro Gly
                 20                  25                  30

Gly Gln Phe Ser Val Asn Trp Ser Asn Ser Gly Asn Phe Val Gly Gly
             35                  40                  45

Lys Gly Trp Gln Pro Gly Thr Lys Asn Lys Val Ile Asn Phe Ser Gly
 50                  55                  60

Ser Tyr Asn Pro Asn Gly Asn Ser Tyr Leu Ala Val Tyr Gly Trp Ser
 65                  70                  75                  80

Arg Asn Pro Leu Ile Glu Tyr Tyr Ile Val Glu Asn Phe Gly Thr Tyr
                 85                  90                  95

Asn Pro Ser Thr Gly Ala Thr Lys His Gly Glu Val Thr Ser Asp Gly
                100                 105                 110

Ser Val Tyr Asp Ile Tyr Arg Thr Gln Arg Val Asn Ala Pro Ser Ile
            115                 120                 125

Glu Gly Thr Arg Thr Phe Arg Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                    165                 170                 175

Glu Gly Tyr Phe Ser Ser Gly Ser Ala Ser Ile Thr Val Ser
                180                 185                 190

<210> SEQ ID NO 75
<211> LENGTH: 190
<212> TYPE: PRT
<213> ORGANISM: Artificial Sequence
<220> FEATURE:
<223> OTHER INFORMATION: Description of Artificial Sequence:
      TrX-HML-AHAE-RRR

<400> SEQUENCE: 75

Gln Thr Ile Gln Pro Gly Thr Gly Tyr His Asn Gly Tyr Phe Tyr Ser
  1               5                  10                  15

Tyr Trp Asn Asp Gly His Gly Gly Val Thr Met Thr Leu Gly Pro Gly
                 20                  25                  30

Gly Gln Phe Ser Val Asn Trp Ser Asn Ser Gly Asn Phe Val Gly Gly
             35                  40                  45

```
Lys Gly Trp Gln Pro Gly Thr Lys Asn Lys Val Ile Asn Phe Ser Gly
         50                  55                  60

Ser Tyr Asn Pro Asn Gly Asn Ser Tyr Leu Ala Val Tyr Gly Trp Ser
 65                  70                  75                  80

Arg Asn Pro Leu Ile Glu Tyr Tyr Ile Val Glu Asn Phe Gly Thr Tyr
                     85                  90                  95

Asn Pro Ser Thr Gly Ala Thr Lys His Gly Glu Val Thr Ser Asp Gly
                100                 105                 110

Ser Val Tyr Asp Ile Tyr Arg Thr Gln Arg Val Asn Ala Pro Ser Ile
            115                 120                 125

Glu Gly Thr Arg Thr Phe Arg Gln Tyr Trp Ser Val Arg Arg Asn Arg
        130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
                180                 185                 190
```

<210> SEQ ID NO 76
<211> LENGTH: 190
<212> TYPE: PRT
<213> ORGANISM: Artificial Sequence
<220> FEATURE:
<223> OTHER INFORMATION: Description of Artificial Sequence:
      TrX-HML-AHAE-RRR-DRHH

<400> SEQUENCE: 76

```
Gln Thr Ile Gln Pro Gly Thr Gly Tyr His Asn Gly Tyr Phe Tyr Ser
 1               5                  10                  15

Tyr Trp Asn Asp Gly His Gly Val Thr Met Thr Leu Gly Pro Gly Gly
                 20                  25                  30

Gly Gln Phe Ser Val Asn Trp Ser Asn Ser Gly Asn Phe Val Gly Gly
             35                  40                  45

Lys Gly Trp Gln Pro Gly Thr Lys Asn Lys Val Ile Asn Phe Ser Gly
         50                  55                  60

Ser Tyr Asn Pro Asn Gly Asn Ser Tyr Leu Ala Val Tyr Gly Trp Ser
 65                  70                  75                  80

Arg Asn Pro Leu Ile Glu Tyr Tyr Ile Val Glu Asn Phe Gly Thr Tyr
                     85                  90                  95

Asn Pro Ser Thr Gly Ala Thr Lys His Gly Glu Val Thr Ser Asp Gly
                100                 105                 110

Ser Val Tyr Asp Ile Tyr Arg Thr Gln Arg Val Asn Ala Pro Ser Ile
            115                 120                 125

Glu Gly Thr Arg Thr Phe Arg Gln Tyr Trp Ser Val Arg Arg Asn Arg
        130                 135                 140

Arg Ser Ser Gly Ser Val Asn Thr Ala Asn His Phe Asp Ala Trp Ala
145                 150                 155                 160

Arg His Gly Leu His Leu Gly Thr Met Asp Tyr Gln Ile Val Ala Val
                165                 170                 175

Glu Gly Tyr Phe Ser Ser Gly Ser Ala Ser Ile Thr Val Ser
                180                 185                 190
```

<210> SEQ ID NO 77
<211> LENGTH: 190
<212> TYPE: PRT
<213> ORGANISM: Artificial Sequence
<220> FEATURE:
<223> OTHER INFORMATION: Description of Artificial Sequence:
      TrX-HML-AHA-RR-DRHH

<400> SEQUENCE: 77

```
Gln Thr Ile Gln Pro Gly Thr Gly Tyr His Asn Gly Tyr Phe Tyr Ser
 1               5                  10                  15

Tyr Trp Asn Asp Gly His Gly Gly Val Thr Met Thr Leu Gly Pro Gly
             20                  25                  30

Gly Gln Phe Ser Val Asn Trp Ser Asn Ser Gly Asn Phe Val Gly Gly
         35                  40                  45

Lys Gly Trp Gln Pro Gly Thr Lys Asn Lys Val Ile Asn Phe Ser Gly
     50                  55                  60

Ser Tyr Asn Pro Asn Gly Asn Ser Tyr Leu Ala Val Tyr Gly Trp Ser
 65                  70                  75                  80

Arg Asn Pro Leu Ile Glu Tyr Tyr Ile Val Glu Asn Phe Gly Thr Tyr
                 85                  90                  95

Asn Pro Ser Thr Gly Ala Thr Lys His Gly Glu Val Thr Ser Asp Gly
            100                 105                 110

Ser Val Tyr Asp Ile Tyr Arg Thr Gln Arg Val Asn Ala Pro Ser Ile
        115                 120                 125

Ile Gly Thr Ala Thr Phe Arg Gln Tyr Trp Ser Val Arg Arg Asn Arg
    130                 135                 140

Arg Ser Ser Gly Ser Val Asn Thr Ala Asn His Phe Asp Ala Trp Ala
145                 150                 155                 160

Arg His Gly Leu His Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190
```

<210> SEQ ID NO 78
<211> LENGTH: 190
<212> TYPE: PRT
<213> ORGANISM: Artificial Sequence
<220> FEATURE:
<223> OTHER INFORMATION: Description of Artificial Sequence:
      TrX-HML-AHAE-RR-DRHH

<400> SEQUENCE: 78

```
Gln Thr Ile Gln Pro Gly Thr Gly Tyr His Asn Gly Tyr Phe Tyr Ser
 1               5                  10                  15

Tyr Trp Asn Asp Gly His Gly Gly Val Thr Met Thr Leu Gly Pro Gly
             20                  25                  30

Gly Gln Phe Ser Val Asn Trp Ser Asn Ser Gly Asn Phe Val Gly Gly
         35                  40                  45

Lys Gly Trp Gln Pro Gly Thr Lys Asn Lys Val Ile Asn Phe Ser Gly
     50                  55                  60

Ser Tyr Asn Pro Asn Gly Asn Ser Tyr Leu Ala Val Tyr Gly Trp Ser
 65                  70                  75                  80

Arg Asn Pro Leu Ile Glu Tyr Tyr Ile Val Glu Asn Phe Gly Thr Tyr
                 85                  90                  95

Asn Pro Ser Thr Gly Ala Thr Lys His Gly Glu Val Thr Ser Asp Gly
            100                 105                 110

Ser Val Tyr Asp Ile Tyr Arg Thr Gln Arg Val Asn Ala Pro Ser Ile
        115                 120                 125

Glu Gly Thr Ala Thr Phe Arg Gln Tyr Trp Ser Val Arg Arg Asn Arg
    130                 135                 140
```

```
Arg Ser Ser Gly Ser Val Asn Thr Ala Asn His Phe Asp Ala Trp Ala
145                 150                 155                 160

Arg His Gly Leu His Leu Gly Thr Met Asp Tyr Gln Ile Val Ala Val
                165                 170                 175

Glu Gly Tyr Phe Ser Ser Gly Ser Ala Ser Ile Thr Val Ser
            180             185                 190
```